（12）United States Patent
Arimitsu et al.

(10) Patent No.: US 10,695,087 B2
(45) Date of Patent: Jun. 30, 2020

(54) PLACEMENT MANIPULATOR AND ATTACHMENT FOR POSITIONING A PUNCTURE INSTRUMENT

(71) Applicants: Canon USA, Inc., Melville, NY (US); The Brigham and Women's Hospital Inc., Boston, MA (US)

(72) Inventors: Yasumichi Arimitsu, Yokohama (JP); Kosuke Fujimoto, Kawasaki (JP); Brian Ninni, Somerville, MA (US); Nobuhiko Hata, Newton, MA (US); Kemal Tuncali, Newton, MA (US)

(73) Assignees: Canon U.S.A., Inc., Melville, NY (US); The Brigham and Women's Hospital Inc., Boston, MA (US)

(*) Notice: Subject to any disclaimer, the term of this patent is extended or adjusted under 35 U.S.C. 154(b) by 370 days.

(21) Appl. No.: 15/787,536

(22) Filed: Oct. 18, 2017

(65) Prior Publication Data
US 2018/0103979 A1 Apr. 19, 2018

Related U.S. Application Data

(60) Provisional application No. 62/410,123, filed on Oct. 19, 2016.

(51) Int. Cl.
*A61B 17/34* (2006.01)
*G01R 33/28* (2006.01)
(Continued)

(52) U.S. Cl.
CPC ...... *A61B 17/3403* (2013.01); *A61B 10/0233* (2013.01); *A61B 90/11* (2016.02);
(Continued)

(58) Field of Classification Search
CPC ........ A61B 17/3403; A61B 2017/3405; A61B 2017/3407; A61B 2017/3409; A61B 90/11
See application file for complete search history.

(56) References Cited

U.S. PATENT DOCUMENTS 4,841,967 A 6/1989 Chang et al.
4,883,053 A 11/1989 Simon
(Continued)

FOREIGN PATENT DOCUMENTS

CA 2784988 A1 2/2013
EP 2561821 A1 2/2013
(Continued)

OTHER PUBLICATIONS

Liu, S., et al, "Automatic Multiple-Needle Surgical Planning of Robotic-Assisted Microwave Coagulation in Large Liver Tumor Therapy", PLoS One, Mar. 16, 2016, vol. 11, No. 3.
(Continued)

*Primary Examiner* — Ashley L Fishback
(74) *Attorney, Agent, or Firm* — Canon U.S.A., Inc., IP Division

(57) ABSTRACT

An apparatus (51) includes a needle placement manipulator (1) and an attachment (52) for the manipulator. The manipulator includes a needle holder and a rotary mechanism. The rotary mechanism (3, 4) has a remote center of motion (RCM: 11) and is configured to position a needle holder (5) such that the axis of the needle holder traces a conical region of coverage (108), the conical region of coverage having the apex thereof at the RCM and the base thereof in a direction towards a subject of needle placement (14). The attachment supports the guide mechanism and is configured to be mounted onto the subject of needle placement. The attachment includes a guide portion (183c) configured to change an inclination of the rotary mechanism with respect to the
(Continued)

subject of needle placement such that the axis of the needle holder intersects an insertion target (14) located outside of the conical region of coverage.

35 Claims, 34 Drawing Sheets

(51) Int. Cl.
*A61B 90/11* (2016.01)
*A61B 10/02* (2006.01)
*A61B 90/00* (2016.01)

(52) U.S. Cl.
CPC ......... *G01R 33/286* (2013.01); *G01R 33/287* (2013.01); *A61B 2017/3407* (2013.01); *A61B 2090/374* (2016.02)

(56) References Cited

U.S. PATENT DOCUMENTS

| | | |
|---|---|---|
| 5,196,019 A | 3/1993 | Davis et al. |
| 5,201,742 A | 4/1993 | Hasson |
| 5,280,427 A | 1/1994 | Magnusson et al. |
| 5,427,099 A | 6/1995 | Adams |
| 5,682,892 A | 11/1997 | Selder et al. |
| 5,957,934 A | 9/1999 | Rapoport |
| 6,079,681 A | 6/2000 | Stern et al. |
| 6,119,032 A | 9/2000 | Martin et al. |
| 6,185,445 B1 | 2/2001 | Knuttel |
| 6,676,669 B2 | 1/2004 | Charles et al. |
| 6,975,896 B2 | 12/2005 | Ehnholm et al. |
| 7,083,608 B2 | 8/2006 | Tomita et al. |
| 7,187,104 B2 | 3/2007 | Yamamoto et al. |
| 7,379,769 B2 | 5/2008 | Piron et al. |
| 7,636,596 B2 | 12/2009 | Solar |
| 7,824,417 B2 | 11/2010 | Magnusson et al. |
| 7,837,627 B1 | 11/2010 | Pruter |
| 8,241,301 B2 | 8/2012 | Zhang et al. |
| 8,308,740 B2 | 11/2012 | Tolley et al. |
| 2001/0000940 A1 | 5/2001 | Maruyama |
| 2002/0019641 A1 | 2/2002 | Truwit |
| 2003/0107299 A1 | 6/2003 | Fujimoto |
| 2004/0064148 A1 | 4/2004 | Daum et al. |
| 2004/0167543 A1 | 8/2004 | Mazzocchi |
| 2004/0260312 A1 | 12/2004 | Magnusson |
| 2005/0216026 A1 | 9/2005 | Culbert |
| 2005/0261581 A1 | 11/2005 | Hughes et al. |
| 2006/0149147 A1 | 7/2006 | Yanof |
| 2006/0229641 A1 | 10/2006 | Gupta et al. |
| 2007/0276407 A1 | 11/2007 | Vogele |
| 2008/0004481 A1 | 1/2008 | Bax |
| 2008/0161829 A1 | 7/2008 | Kang |
| 2008/0167663 A1 | 7/2008 | De Mathelin et al. |
| 2008/0200798 A1 | 8/2008 | Eklund et al. |
| 2009/0079431 A1 | 3/2009 | Piferi et al. |
| 2009/0234369 A1 | 9/2009 | Bax et al. |
| 2010/0010505 A1 | 1/2010 | Herlihy et al. |
| 2010/0082040 A1 | 4/2010 | Sahni |
| 2011/0190787 A1 | 8/2011 | Sahni |
| 2011/0251624 A1 | 10/2011 | Yi et al. |
| 2012/0022368 A1 | 1/2012 | Brabrand et al. |
| 2013/0069651 A1 | 3/2013 | Luminani |
| 2013/0282022 A1 | 10/2013 | Yousef |
| 2013/0345718 A1 | 12/2013 | Crawford |
| 2014/0018822 A1 | 1/2014 | Main |
| 2014/0052154 A1 | 2/2014 | Griffiths et al. |
| 2014/0121675 A1 | 5/2014 | Bax et al. |
| 2014/0128881 A1 | 5/2014 | Tyc et al. |
| 2014/0128883 A1 | 5/2014 | Piron et al. |
| 2014/0200445 A1 | 7/2014 | Boezaart |
| 2014/0275978 A1 | 9/2014 | Fujimoto et al. |
| 2014/0275979 A1 | 9/2014 | Fujimoto et al. |
| 2014/0336670 A1 | 11/2014 | Brabrand et al. |
| 2014/0350572 A1 | 11/2014 | Elhawary et al. |
| 2015/0238266 A1 | 8/2015 | Fujimoto et al. |
| 2016/0074063 A1 | 3/2016 | Arimitsu et al. |
| 2017/0014200 A1 | 1/2017 | Onuma et al. |
| 2017/0030557 A1 | 2/2017 | Chen et al. |
| 2017/0071626 A1 | 3/2017 | Onuma et al. |

FOREIGN PATENT DOCUMENTS

| | | |
|---|---|---|
| JP | 2004320846 A | 11/2004 |
| JP | 2005083961 A | 3/2005 |
| JP | 2008237971 A | 10/2008 |
| WO | 2012178109 A1 | 12/2012 |
| WO | 2013084107 A2 | 6/2013 |
| WO | 2014152685 A1 | 9/2014 |
| WO | 2017/132505 A1 | 8/2017 |

OTHER PUBLICATIONS

Bukai, E., "Design of a novel needle steering manipulator for minimally invasive guided breast biopsy", Robotics and Mechanics, Aug. 2016, University of Twente.

Masamune, K., et al, "Development of an MRI-Compatible Needle Insertion Manipulator of Stereotactic Neurosurgery", Journal of Image Guided Surgery, Sep. 25, 1995, 1:242-248; retrieved Oct. 2, 2017.

Fischer, G. S.,et al. "MRI Guided Needle Insertion—Comparison of Four Technique", In Annual Scientific Conference of the Society of Interventional Radiology, 2006. (Abstract only).

Koethe, Y., et al., "Accuracy and efficacy of percutaneous biopsy and ablation using robotic assistance under computed tomography guidance: a phantom study" Eur Radiol., 2013.

Maxio Brochure: Planning and Targeting for CT guided Procedures by Perfint.

Palmer, K., et al, "Development and evaluation of optical needle depth sensor for percutaneous diagnosis and therapies", Medical Imaging, Proc of SPIE, 2014, vol. 9036.

Perfint, Inc Maxio Robot—Features http://www.perfinthealthcare.com/MaxioFeatures.asp Accessed Sep. 11, 2015.

Song, S., et al., "Biopsy Needle Artifact Localization in MRI-guided Robotic Transrectal Prostate Intervention," IEEE Transactions on Biomedical Engineering, Jul. 2012, vol. 59, No. 7.

Song, S.E., et al., "Design Evaluation of a Double Ring RCM Mechanism for Robotic Needle Guidance in MRI-guided Liver Interventions", International Conference on Intelligent Robots and Systems, Nov. 3-7, 2013, Tokyo, Japan.

Hata, H., et al.,"MRI-Compatible Manipulator With Remote-Center-of-Motion Control", J Magn Reson Imaging, May 2008, pp. 1130, vol. 27, No. 5; http://www.ncbi.nlm.nih.gov/pmc/articles/PMC2815332/.

FIG. 3
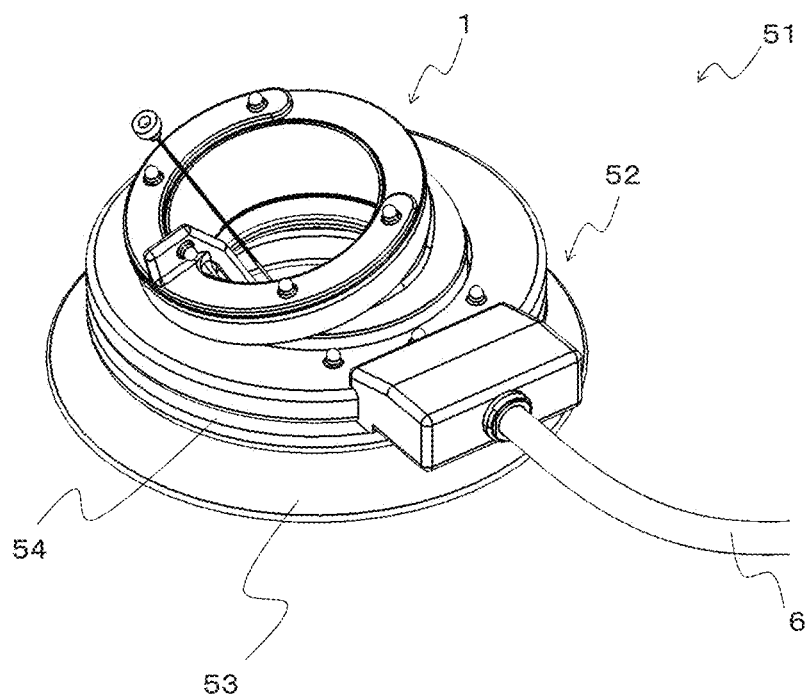
FIG. 4A
FIG. 4B
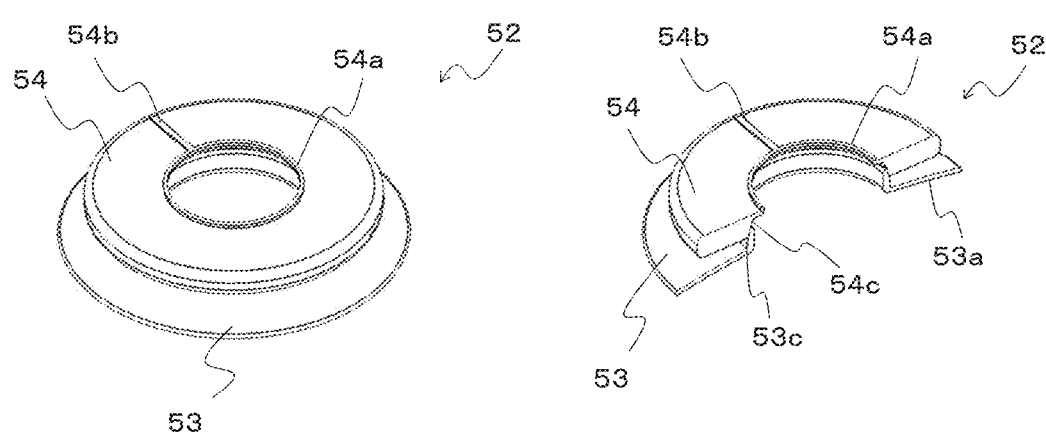

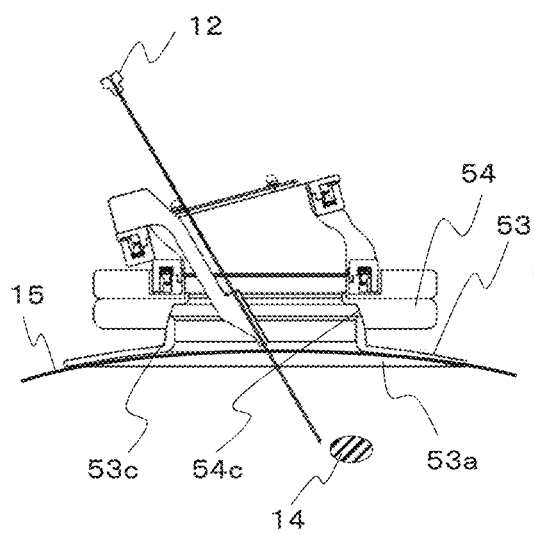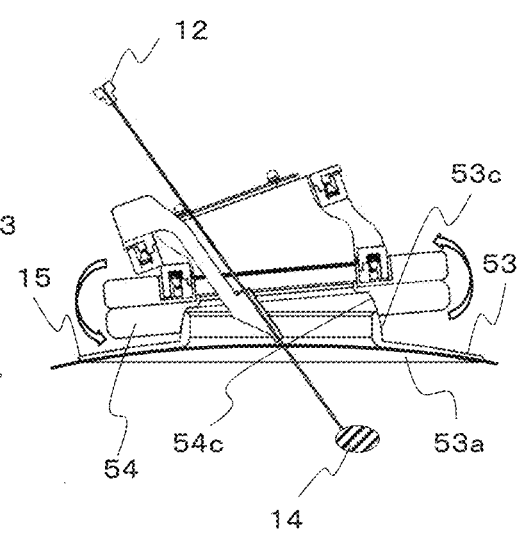

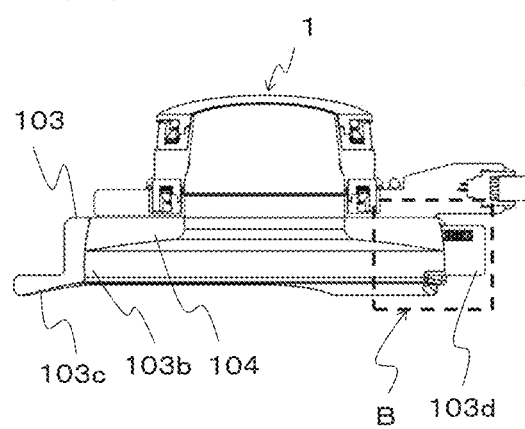
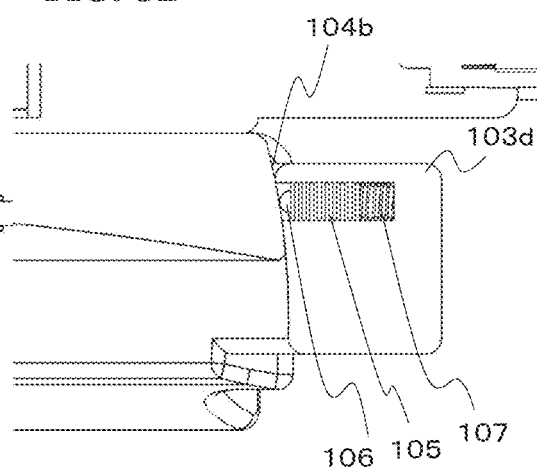
FIG. 8A  FIG. 8B
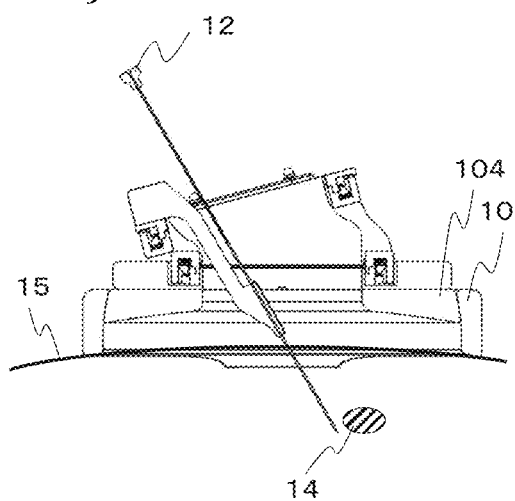
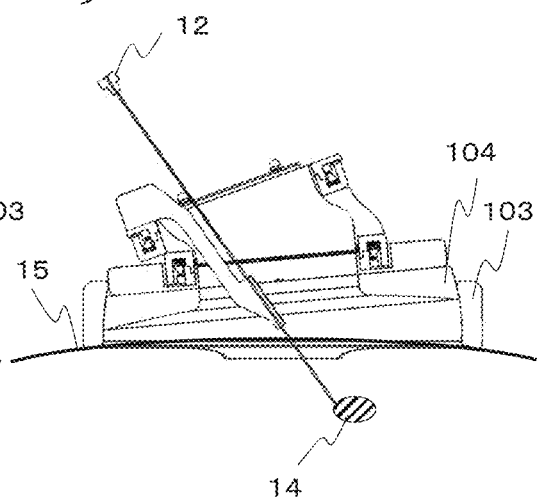
FIG. 9A  FIG. 9B

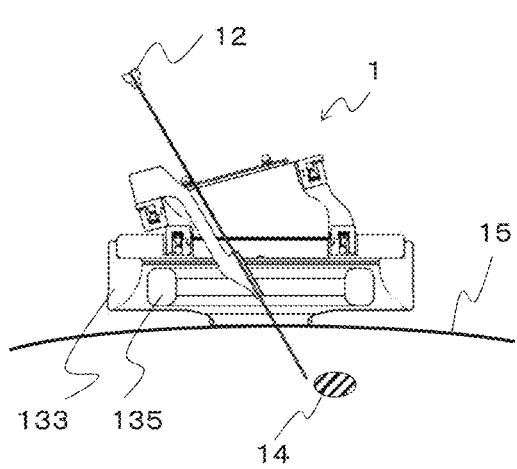
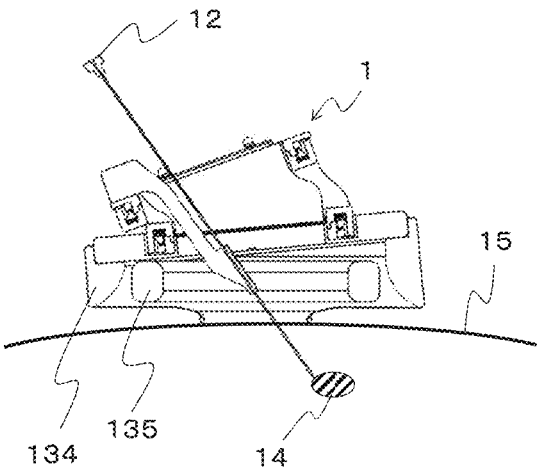
FIG. 18A
FIG. 18B

FIG. 23A
FIG. 23B
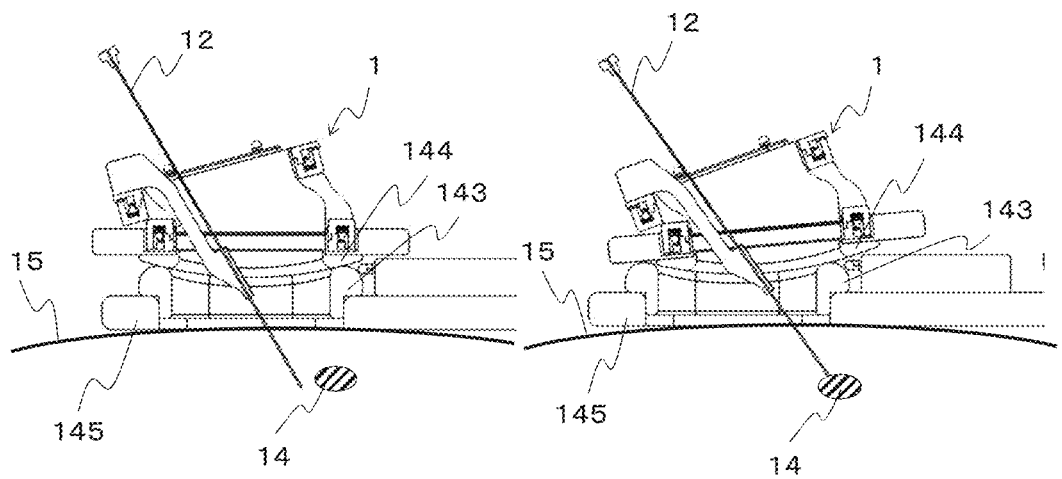
FIG. 24
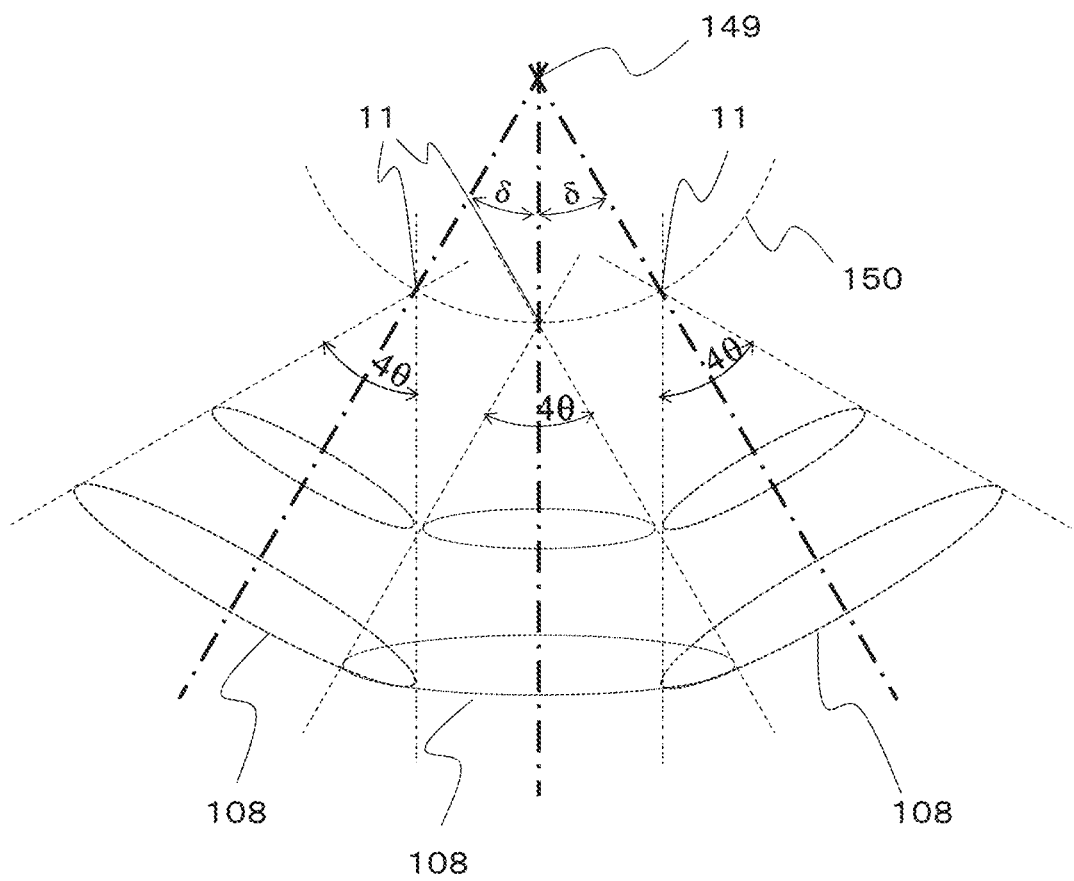

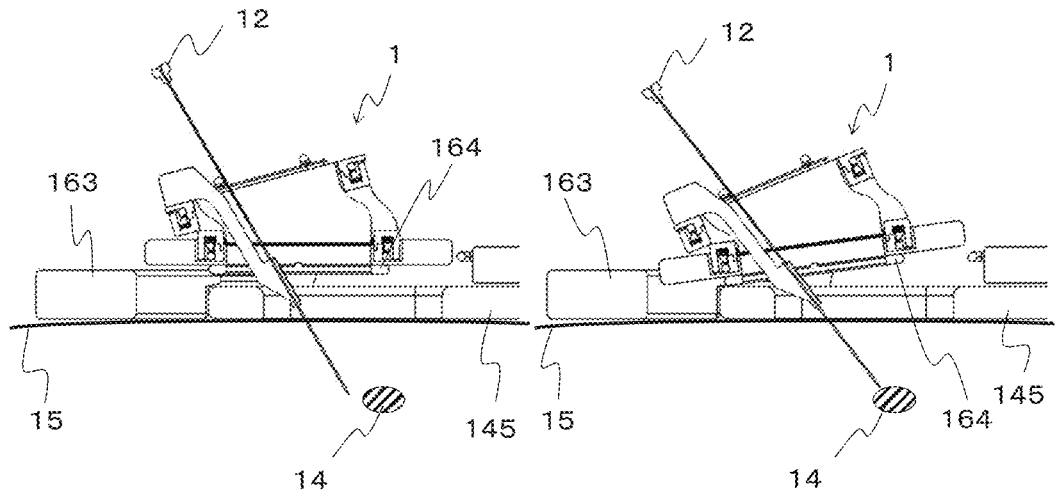
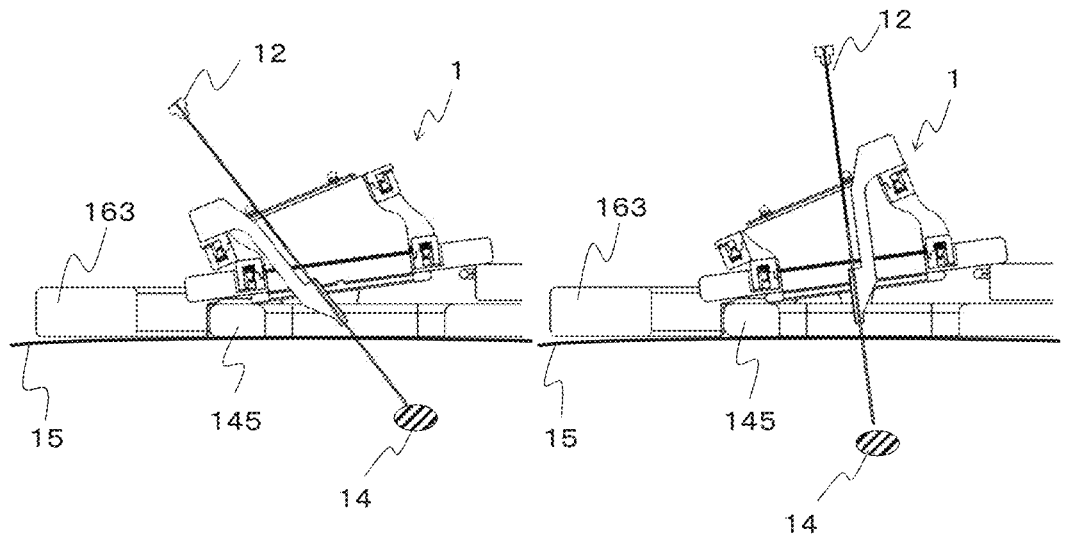
FIG. 34A  FIG. 34B  FIG. 34C  FIG. 34D

FIG. 35A
FIG. 35B
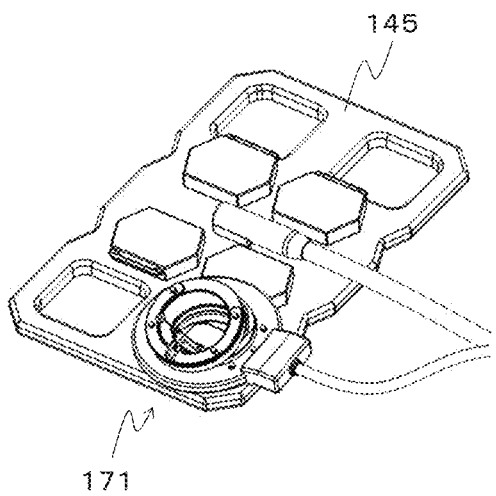
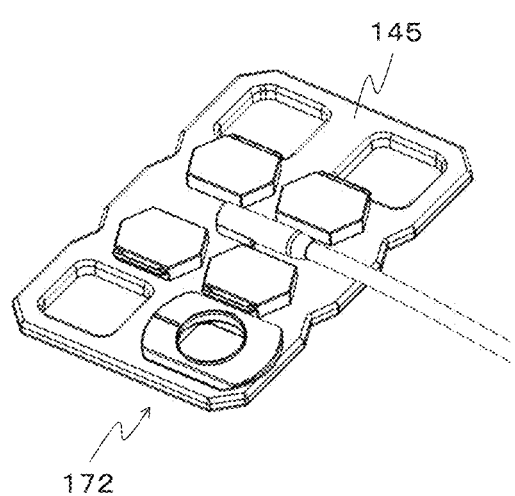

FIG. 38
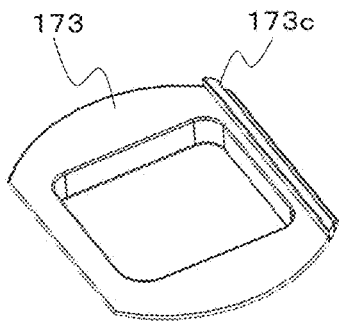
FIG. 39A
FIG. 39B
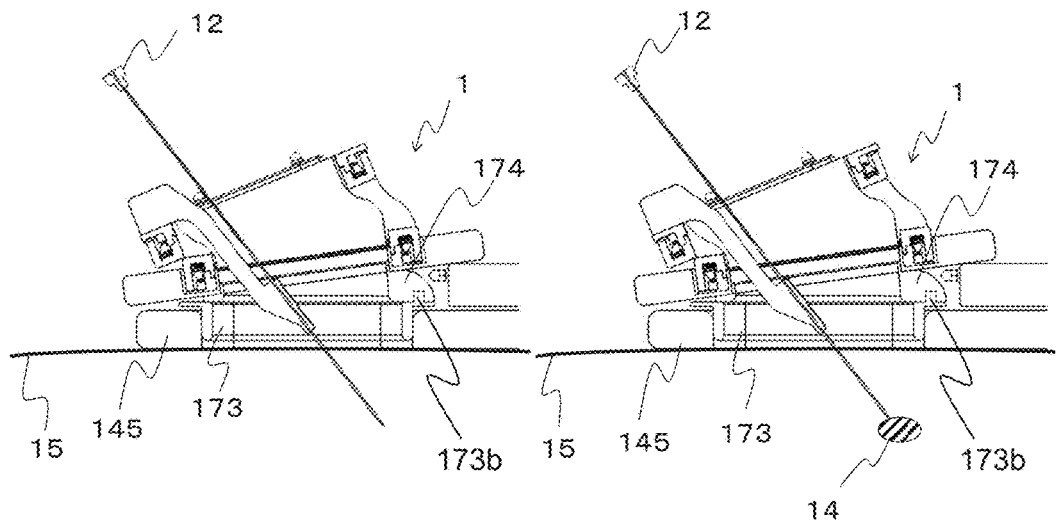
FIG. 40A
FIG. 40B
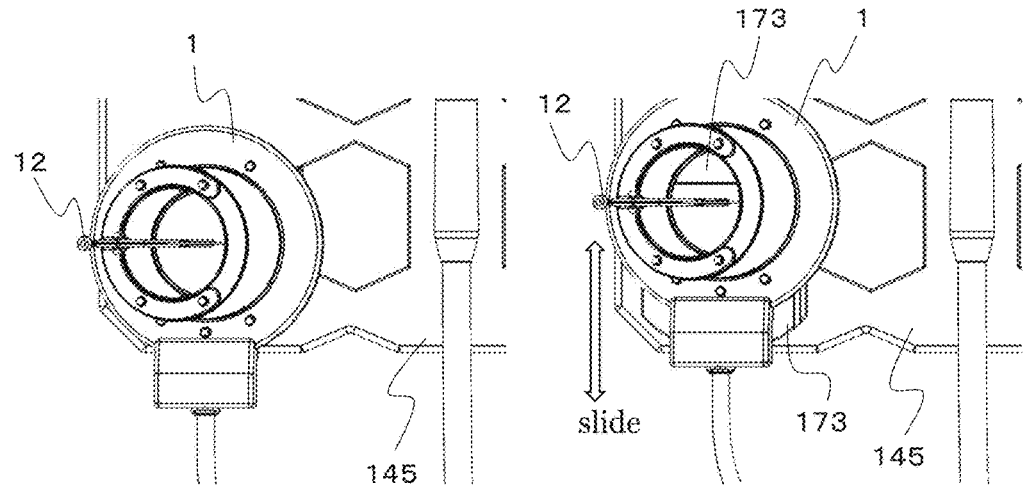

PLACEMENT MANIPULATOR AND ATTACHMENT FOR POSITIONING A PUNCTURE INSTRUMENT

CROSS-REFERENCE TO RELATED APPLICATIONS

The present application claims priority from U.S. provisional patent application No. 62/410,123 filed Oct. 19, 2016, the disclosure of which is hereby incorporated by reference herein in its entirety.

BACKGROUND OF THE INVENTION

Field of the Invention

The present disclosure generally relates to medical devices, and in particular it relates to a placement manipulator for holding and positioning a puncture instrument in minimally invasive puncture therapy and to an attachment for adjusting and holding the posture of the needle placement manipulator.

Description of Related Art

Medical devices for in-vivo diagnostic testing, therapy treatment and surgery of patients are well known. Typical procedures for minimally invasive therapy include a percutaneous puncture therapy in which various instruments such as needles and/or catheters are carefully guided into an affected area of a patient. Examples of puncture therapy include ablation, which is a treatment performed by burning tumor or cancer cells with radiation waves, and cryotherapy in which tumor and cancerous cells are frozen with a refrigerant, cooling gas, or the like. In addition, puncture biopsy is widely performed as part of pathological diagnosis based on tissue collection. Another example is percutaneous microwave coagulation (MC) therapy, which is a minimally invasive surgery, used in malignant liver tumor treatments. In the MC technique, to destroy an entire malignant liver tumor, tumor size and accessibility of the lesion are factors to be considered. For example, for a small liver tumor, microwave coagulation (MC) can be performed with only a single needle, whereas to cover irregular and large tumors, a series of single-needles is required to apply multiple overlapping MC treatment. The multiple-needle surgical planning requires a needle collision-free reachable workspace, which is a set of needle insertion trajectories that reach the target with no collision between the needle and obstacles. See, for example, Liu, et al., "Automatic Multiple-Needle Surgical Planning of Robotic-Assisted Microwave Coagulation in Large Liver Tumor Therapy", PLoS ONE 11(3): e0149482, Mar. 16, 2016.

To accurately position the needle to a target, such as a tumor, in such puncture therapy, medical images acquired using a medical imaging modality, such as an X-ray computed tomography (CT) scanner or a magnetic resonance imaging (MRI) scanner, are used to visualize the position and trajectory of the needle in the body. In such puncture therapy using such visualization modality, it is difficult to reach target tissue by one puncture, and medical image acquisition is performed a plurality of times to perform planning based on the acquired images to reach the target tissue while correcting the puncture path little by little in a stepwise manner. For that reason, to reduce the surgery time and burden on the patient, development of a needle placement manipulator for positioning the needle to a target tissue with few path correction times has been proposed. In particular, a body-mount needle placement manipulator that is to be directly mounted on the body surface of a patient has been proposed.

U.S. Patent Application Publication No. 2014/0275978 discloses an example of the body-mount needle placement manipulator which includes a pair of rotary guides mounted at a fixed angle with respect to each other for determining the direction of the needle on the basis of a remote center of motion (RCM) of the rotary guides.

U.S. Patent Application Publication No. 2014/0275978 discloses a method for disposing, on a patient's body, a needle placement manipulator and a radio-frequency (RF) coil without interference with each other. The method employs a single-loop RF coil, which is one kind of surface coil, as the RF coil and uses a first attachment including a base surface in contact with the patients' body and a disposition portion on which the RF coil is disposed and a second attachment connected to a base body of the manipulator. In this manner, the manipulator and the single-loop RF coil can be disposed without interference with each other. However, the range of coverage for reaching a needle insertion target on the patient tends to be limited.

To increase the positioning range (range of coverage) using the needle placement manipulator with the method disclosed in U.S. Patent Application Publication No. 2014/0275978, it is necessary to increase the mount angle of the second rotation guide with respect to the first rotation guide. To increase the mount angle of the second rotation guide with respect to the first rotation guide, it is necessary to reduce the external dimensions of the second rotation guide or to dispose the second rotation guide farther away from the first rotation guide in order to prevent interference between the rotation guides. When the external dimensions of the second rotation guide are reduced, the opening of the second rotation guide in which a needle holder is disposed is reduced in size. This can make it difficult for the needle to access a skin in the vicinity of the puncture point through the opening and can cause interference between the needle holder and the second rotation guide. When the second rotation guide is disposed farther away from the first rotation guide, the height of the needle placement manipulator increases as the mount angle of the second rotation guide with respect to the first rotation guide increases, which increases the size of the manipulator, and therefore can cause interference between the needle placement manipulator and the bore of the MRI or X-ray CT scanner.

For the above reasons, it is not easy to increase the coverage of the body-mount needle placement manipulator disclosed in U.S. Patent Application Publication No. 2014/0275978. In addition, in U.S. Patent Application Publication No. 2014/0275978, if the target tissue is not within the coverage of the needle placement manipulator after the second attachment is disposed on the patient's body, a repetition of an attachment operation, such as repositioning the first attachment and the RF coil on the patient's body from the beginning, and again mounting the needle manipulator becomes necessary. The reoperation can increase a burden on the patient due to an extended operation time and can increase safety risks because, for example, the sterilized needle placement manipulator may come into contact with non-sterilized objects, such as the RF coil.

SUMMARY OF THE INVENTION

In view of the above, the present disclosure provides a needle placement manipulator having an increased coverage and an attachment of the needle placement manipulator capable of adjusting the coverage of the needle placement manipulator even if a needle insertion target (tissue target) results to be out of coverage of the needle placement manipulator after the needle placement manipulator is placed on the patient's body.

According to one embodiment, the present disclosure provides an attachment including a needle holder, a guide mechanism, an engaging unit, and a mount surface, as well as a needle placement manipulator. The guide mechanism is configured to hold a needle along an insertion axis. The guide mechanism is configured to position the insertion axis in a predetermined direction relative to a target tissue. The engaging unit is configured to support and fix an apparatus main body that supports the guide mechanism. The mount surface is configured to be placed on a subject of needle placement. The attachment includes an inclined surface configured to change the apparatus main body to a predetermined posture with respect to the mount surface and an adjusting unit configured to change an inclination angle or a bearing of the inclined surface. The apparatus main body and the attachment each include a restraining unit configured to restrain a relative position of each other. The needle placement manipulator is configured such that the apparatus main body is fixed to the attachment with the engaging unit.

According to another embodiment, the present disclosure provides an apparatus, comprising: a needle holder (5) having an axis (5a) and configured to hold a needle (12) aligned relative to a subject of needle placement (15); a rotary mechanism (3, 4) having a remote center of motion (RCM: 11), the rotary mechanism (3, 4) configured to position the needle holder (5) such that the axis of the needle holder traces a conical region of coverage, the conical region of coverage having the apex thereof at the RCM and the base thereof in a direction towards the subject of needle placement (14); a base body (2) configured to be rigidly fixed to the guide mechanism (3, 4); and an attachment (52, 183)) that supports the base body and configured to be mounted onto the subject of needle placement. The attachment (183) comprises: a fitting portion (183a) configured to engage with the base body, and a guide portion (183c) configured to change an inclination of the rotary mechanism with respect to the subject of needle placement, wherein the guide portion changes the inclination of the rotary mechanism such that the axis of the needle holder intersects an insertion target located outside of the conical region of coverage.

According to the various embodiments of the present disclosure, even if it is found that the target tissue is outside of the coverage of a needle placement manipulator after the needle placement manipulator is placed on a patient's body, the coverage can be corrected by adjustment using the attachment so that the target issue falls within the coverage.

Further features of the present invention will become apparent from the following description of exemplary embodiments with reference to the attached drawings.

BRIEF DESCRIPTION OF THE DRAWINGS

FIG. 3 is a schematic perspective view of a needle placement manipulator according to the first embodiment.

FIG. 4A is a schematic perspective view of an attachment according to the first embodiment.

FIG. 4B is a schematic perspective view of a cross section of the attachment.

FIGS. 5A and 5B are schematic cross-sectional views of the needle placement manipulator illustrating puncture using the needle placement manipulator.

FIG. 8A is a cross-sectional view of the needle placement manipulator.

FIG. 8B is an enlarged view of a dashed-line region B in FIG. 8A.

FIGS. 9A and 9B are schematic cross-sectional views of the needle placement manipulator illustrating simulated puncture.

FIG. 18A is a schematic cross-sectional view of the first needle placement manipulator illustrating simulated puncture.

FIG. 18B is a schematic cross-sectional view of the second needle placement manipulator illustrating simulated puncture.

FIGS. 23A and 23B are schematic cross-sectional views of the needle placement manipulator illustrating simulated puncture.

FIG. 24 is a diagram illustrating the coverage of the needle placement manipulator.

FIGS. 34A, 34B, 34C, and 34D are schematic cross-sectional views of the needle placement manipulator illustrating simulated puncture.

FIG. 35A is a schematic perspective view of a needle placement manipulator according to a seventh embodiment disposed on the phased array coil.

FIG. 35B is a schematic perspective view of the needle placement manipulator disposed on the phased array coil.

FIG. 38 is a schematic perspective view of a fixed portion of the seventh embodiment.

FIGS. 39A and 39B are schematic cross-sectional views of the needle placement manipulator illustrating simulated puncture.

FIGS. 40A and 40B are schematic plan views of the needle placement manipulator illustrating simulated puncture.

DESCRIPTION OF THE EMBODIMENTS

The present disclosure will be described hereinbelow with reference to the attached drawings. It is to be understood that the present disclosure is not limited to the various embodiments described. Needle placement manipulators and attachments therefor resulting from any combination of the various embodiments are also within the scope of the present disclosure.

First Embodiment

Figure 1A:
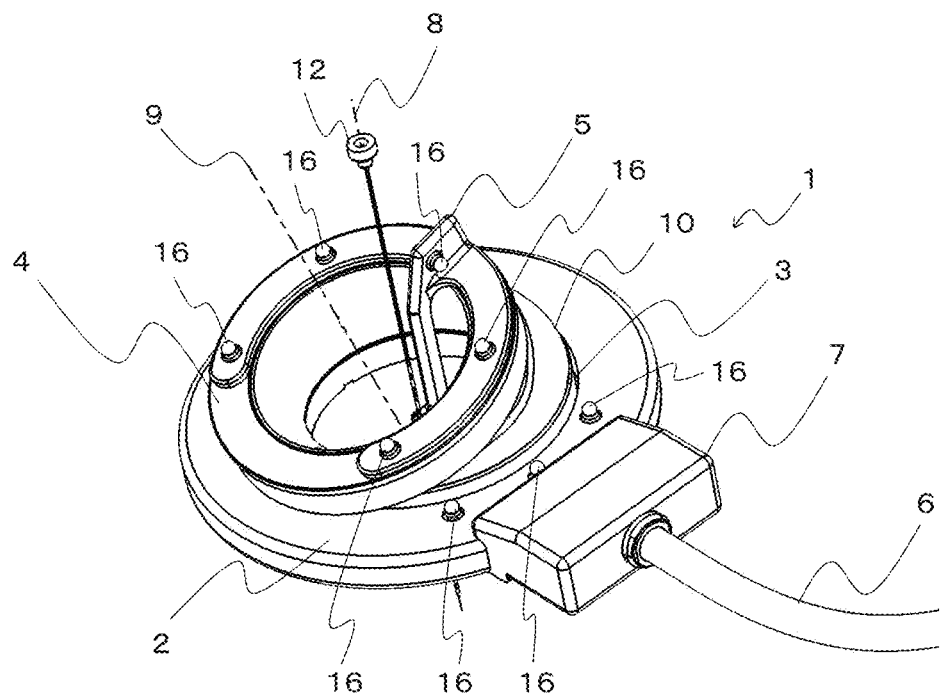
FIGS. 1A, 1B, and 1C are schematic perspective views of an apparatus main body according to a first embodiment of the present disclosure.
Figure 1B:
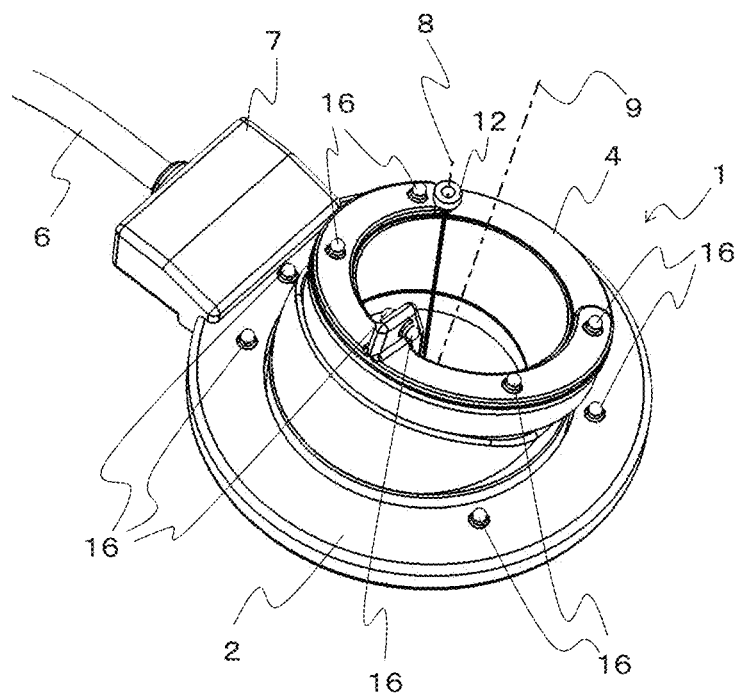
Figure 1C:
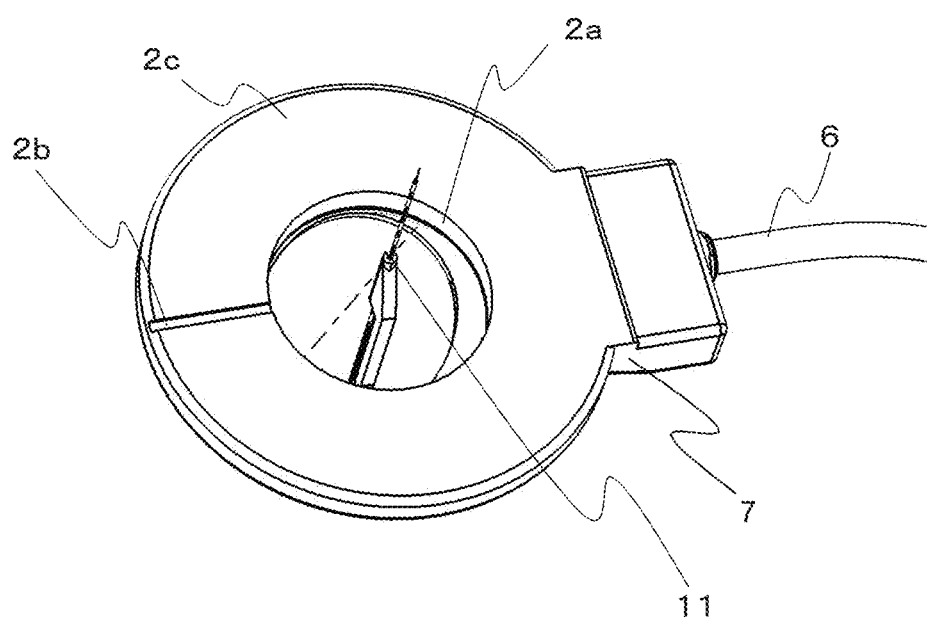

Referring to FIGS. 1A and 1C to FIGS. 11A and 11B, a first embodiment of the present disclosure will be described. FIGS. 1A to 1C are schematic perspective views of an apparatus main body 1, which is part of a needle placement manipulator viewed from different angles, according to the first embodiment. The apparatus main body 1 is a remote center of motion (RCM) mechanism having two degrees of freedom in rotation. In the present embodiment, an X-ray computed tomography (CT) scanner is used to visualize the inside of a patient's body, medical devices, medical-device guide devices, etc. First, the structure of the apparatus main body 1 will be described. A first rotation guide 3 that is rotatable about an axis 8 is mounted on a base body 2 of the apparatus main body 1. A rigid cover 10 is mounted on the first rotation guide 3. A second rotation guide 4 is mounted onto the rigid cover 10. A needle holder 5, for guiding a needle 12 along an insertion axis 5a and holding the needle 12, is mounted on the second rotation guide 4. As shown in FIGS. 1A, 1B, 2A and 2B, an element described as mounted onto another element means that such elements are rigidly connected. The term "rigidly connected" is intended to mean that the connection results in there being no relative motion between the connected elements except for minor tolerances.

FIG. 1C shows a bottom view of base body 2 of the apparatus main body 1. The base body 2 is a ring shaped structure configured to support on its upper surface the first rotation guide 3. On the base body 2, a cylindrical fitting portion 2a is formed as cylindrical opening substantially concentric with an axial center thereof. A bottom surface 2c of the base body 2 is provided with a groove 2b. The cylindrical fitting portion 2a serves to engage the apparatus main body 1 onto an attachment.

The second rotation guide 4 is a mechanism rotatable about an axis 9. The axis 9 and the second rotation guide 4 including the needle holder 5 can be rotated about the axis 8 by the first rotation guide 3. The axis 8 and the axis 9 are designed to cross each other and form an angle θ. The angle θ is set to satisfy the condition of 0°<θ<90°, preferably, θ=15° to 20°, for example. The first and second rotation guides 3 and 4 each include a driving unit that causes rotational displacement and a detecting unit for detecting the rotational displacement. Rotational displacement between the first and second rotary guides 3 and 4 may also be determined by tracking markers 16. Tracking markers 16 are fiducial markers which can be mounted on two or more of the base body 2, the first rotation guide 3, and the second rotation guide 4. The tracking markers can be designed to be visible under magnetic resonance imaging and/or computerized tomographic imaging, or visible other imaging modality. A mix of different tracking markers may be used for providing visibility under plural imaging modalities. The tracking markers may be set along the radius the rotation guides and/or base body 2, at predetermined angles, e.g., at 0 degrees, 120 degrees and 240 degrees of radially marked surface on the top surface of the base body 2 and rotation guides 3 and/or 4.

An electrical component box 7 includes not-shown elements, such as a circuit board including a power supply unit that supplies power to the driving units and the detecting units, and a signal processing unit for processing signals coming from the detecting units. The electrical component box 7 also provides communication interface (electronic connections) for one or more of the driving units and the detecting units so that commands can be received from an external device, such as a computer. The electrical component box 7 may also include programmable logic for use with a programmable logic devices (PDL) or application specific integrated circuit (ASIC) devices used for controlling needle positioning with the driving units. The electrical component box 7A is connected to non-illustrated control unit (e.g. a computer) that controls the electronic components included in the electrical component box 7.

Figure 2A:
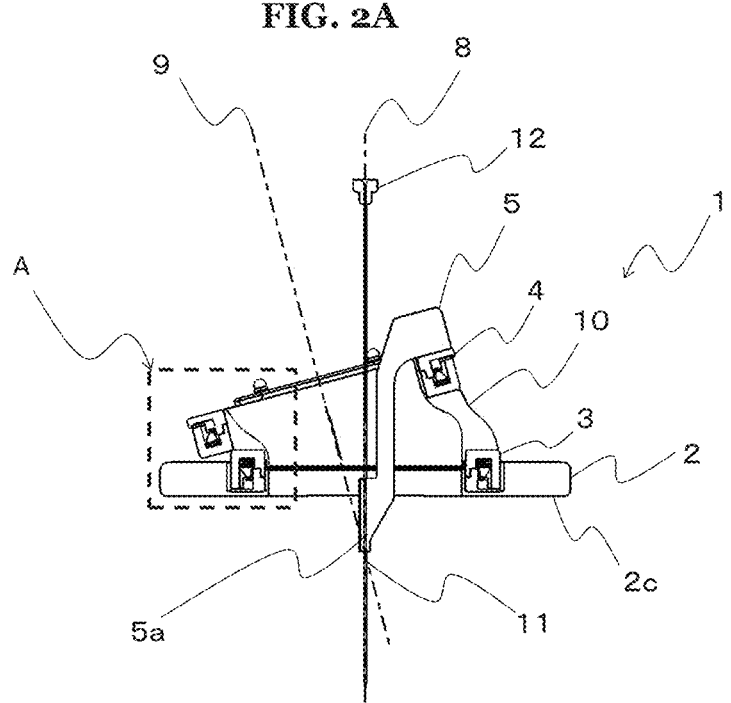
FIG. 2A is a schematic cross-sectional view of the apparatus main body.
Figure 2B:
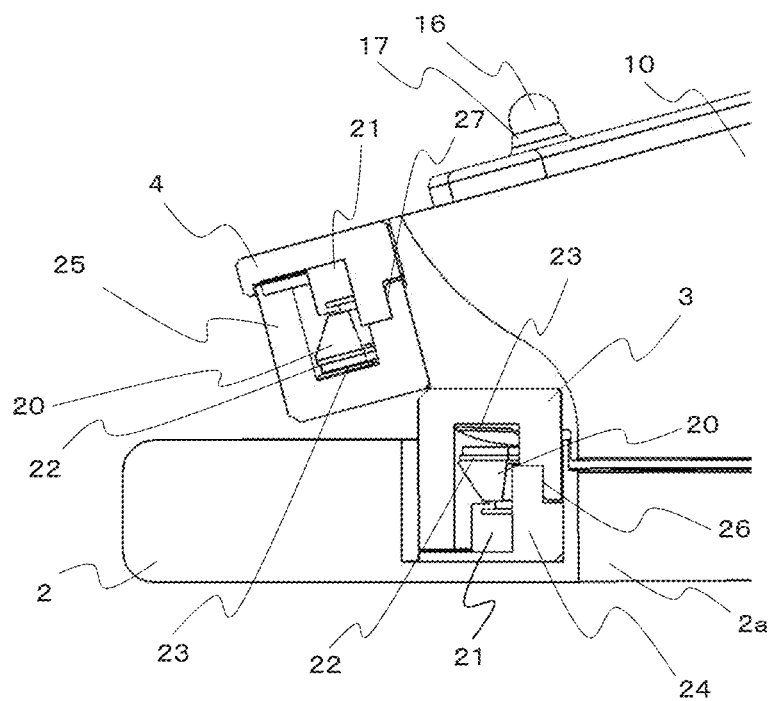
FIG. 2B is an enlarged view of a dashed-line region A in FIG. 2A.

FIG. 2A is a schematic cross-sectional view of the apparatus main body 1 taken along a sectional plane including the axes 8 and 9 in FIG. 1A or 1B. FIG. 2B is an enlarged view of a dashed-line region A shown in FIG. 2A. In FIG. 2A, the bottom surface 2c of the base body 2 is a flat surface. The first rotary guide 3 and the second rotary guide 3 are mounted at a predetermined angle with respect to each other, such that the axes 8 and 9 intersect at a point referred herein as the remote center of motion (RCM) 11. When the needle 12 is inserted along the insertion axis 5a of the needle holder 5, the needle 12 passes through the remote center of motion (RCM) 11 regardless of the rotational displacement of the first rotation guide 3 with respect to the second rotation guide 4.

Referring next to FIG. 2B, the driving unit and the detecting unit disposed in each of the first and second rotation guides 3 and 4 will be described. The present embodiment includes a piezoelectric actuator as the driving unit and an optical encoder as the detecting unit disposed in each of the first and second rotation guides 3 and 4. Referring to FIG. 2B, a first support member 24 is fixed to the base body 2. The first rotation guide 3 can rotate smoothly about the axis 8 with a bearing 26 mounted on the first support member 24. The first rotation guide 3 and a second support member 25 are fixed to the cover 10. The second rotation guide 4 can rotate smoothly about the axis 9 with a bearing 27 mounted on the second support member 25.

Next, the configuration of the piezoelectric actuator will be described. An elastic member 20 is attached to the each of the first rotation guide 3 and the second support member 25, with the directions of rotation about the axes 8 and 9 restrained. An electromechanical energy transducer 22 is firmly fixed to each elastic member 20 with an adhesive (not shown). The elastic member 20 and the electromechanical energy transducer 22 are pushed against a movable object 21 fixed to the first support member 24 or the second rotation guide 4 by a pressure unit 23 provided in the first rotation guide 3 or the second support member 25. With this configuration, the elastic member 20 and the movable object 21 can be frictionally driven relative to each other in the direction of rotation by applying a voltage with a predetermined frequency band to the electromechanical energy transducer 22 to vibrate the elastic member 20 in an out-of-plane direction.

The first rotation guide 3 includes an optical encoder (not shown), which is one component of the detecting unit, and the first support member 24 includes an optical scale (not shown), which is one component of the detecting unit, at a radial position opposed thereto. Likewise, the second support member 25 includes an (not shown) optical encoder, which is one component of the detecting unit, and the second rotation guide 4 includes an optical scale (not shown), which is one component of the detecting unit, at a radial position opposed thereto. This configuration allows detection of displacement in rotational angles of the first and second rotation guides 3 and 4 about the axes 8 and 9, respectively.

A material of the driving units will be described. The first and second support members 24 and 25 and the first and second rotation guides 3 and 4 may be formed of metal, such as an aluminum alloy, rigid plastic, such as polyether ether ketone (PEEK), or ceramic, whose X-ray absorption coefficients are relatively low. Materials having low X-ray absorption coefficients are preferable because the imaging of the support member's external dimension accuracy directly influences the accuracy of the arrival position of the medical instrument with respect to the object target of needle placement (e.g., a tumor). The elastic members 20 may be made of metal, such as an aluminum alloy, or fine ceramic, such as alumina, silicon nitride, or partially stabilized zirconia (PSZ), whose X-ray absorption coefficients are also relatively low. The electromechanical energy transducers 22 may be formed of piezoelectric ceramic, such as lead zirconate titanate or barium titanate. The material of the movable objects 21 may be selected to have stable sliding characteristic and abrasion-resistant characteristic with respect to the elastic member 20, for example, a magnesium-based aluminum alloy whose surface is made rigid by alumite treatment or nitriding treatment and a fiber-reinforced resin, such as polyether ether ketone (PEEK) containing carbon fibers or the like. The pressure units 23 may be formed of non-magnetic metal, such as phosphor bronze, or high-toughness ceramic, such as partially stabilized zirconia (PSZ).

The apparatus main body 1 includes a plurality of markers 16 (fiduciary markers) each fixed to a pedestal 17 to detect the position and posture of the apparatus main body 1 in a CT bore. In the present embodiment, as shown in FIGS. 1A and 1B, five markers on the base body 2, four markers on the second rotation guide 4, and two markers on the side of the needle holder 5, eleven in total, are disposed to allow detection of the posture of the apparatus main body 1, the posture of the second rotation guide 4, and the position of the needle holder 5. The material of the fiducial markers will depend on the modality in which the needle placement manipulator will be used. For installation of the apparatus main body 1 in a CT scanner, the markers 16 may be formed of gypsum, resin, ceramic, an aluminum alloy, or another material with a CT value of about 1,000.

Referring to FIG. 3 to FIGS. 5A and 5B and FIGS. 10A to 10C, the configuration of a needle placement manipulator 51 for determining the direction of the needle 12 in the apparatus main body 1 relative to the target portion and a workflow for puncture with the needle 12 will be described. FIG. 3 is a schematic perspective view of the needle placement manipulator 51 of the present embodiment. FIG. 4A is a schematic perspective view of an attachment 52, and FIG. 4B is a schematic perspective view of a cross section of the attachment 52. In the present embodiment, FIG. 3 shows the attachment 52 combined with the apparatus main body 1 to form the needle placement manipulator 51. In the drawings, the attachment 52 includes a fixed portion 53 and a movable portion 54. The fixed portion 53 and the movable portion 54 respectively include spherical guides 53$c$ and 54$c$ so that the movable portion 54 can change in posture relative to the fixed portion 53 along the spherical guide 53$c$. The center of spherical surfaces including the spherical guides 53$c$ and 54$c$ may coincide with the remote center of motion (RCM) 11.

The fixed portion 53 includes a mount portion with a mount surface. The bottom of the mount portion includes a curved mount surface 53$a$ which allows stable mounting of the attachment 52 onto a patient by following the shape of the body surface of the patient. The movable portion 54 has a ridge key 54$b$. A groove 2$b$ (shown in FIG. 1C) formed in the bottom of the apparatus main body 1 is shaped to be fitted with the ridge key 54$b$. The cylindrical fitting portion 2$a$ (FIG. 1C) provided in base body 2 of the apparatus main body 1 is fitted to an axial fitting portion 54$a$ of the attachment 52, so that the position and posture of the apparatus main body 1 relative to the attachment 52 can be fixed.

A method for changing the posture of the movable portion 54 with respect to the fixed portion 53 will be described. The movable portion 54 can be changed in posture relative to the fixed portion 53 along the spherical guides 53$c$ and 54$c$ about the remote center of motion (RCM) it After the posture of the movable portion 54 is changed, the movable portion 54 can be fixed relative to the fixed portion 53 using an electromechanical actuator unit 103$d$ or a mechanical knurled knob 116, which may be referred herein as a fixing unit, and will be described later in more detail. To prevent the movable portion 54 from being disengaged from the fixed portion 53, such as when the needle placement manipulator is used upwards (in a position opposite to the direction of gravity), the attachment 52 may have a spring, a wire, a magnet, or the like as appropriate to urge the movable portion 54 against the fixed portion 53.

FIGS. 5A and 5B illustrate a simulated puncture of a needle 12 to a target tissue 14 using the needle placement manipulator 51 disposed on a patient's skin 15. In this case, the remote center of motion (RCM) 11 may be set on the skin 15, and the puncture point may not move regardless of the displacement of the first and second rotation guides 3 and 4 with respect to each other. FIG. 5A illustrates a state in which the intended target tissue 14 is out of coverage, so that the tip of needle 12 cannot be brought to the target tissue 14 even if the first and second rotation guides 3 and 4 are rotated to a maximum inclination. However, by changing the posture of the movable portion 54 using the attachment 52 of the present disclosure, the target tissue 14 can be brought within the coverage, so that the needle 12 can be brought to the target tissue 14, as illustrated in FIG. 5B. Whether the target tissue 14 is within the coverage of the apparatus main body 1 is determined using the following procedure, and the needle 12 is directed to the target tissue 14. First, the posture of the movable portion 54 is determined and fixed at an initial step of mounting the needle placement manipulator 51 onto the body of a patient. Subsequently, whether the coverage of the apparatus main body 1 includes the target tissue 14 is determined through calculation based on a CT image using the fiducial markers 16 provided on the apparatus main body 1. If it is determined that the target tissue 14 is within the coverage, planning for bringing the needle 12 to the target tissue 14 is executed to displace the first and second rotation guides 3 and 4 to predetermined angles, thereby directing the needle 12 to the direction of the target tissue 14. If it is determined that the target tissue 14 is not within the coverage, the movable portion 54 of the attachment 52 is operated to expand the coverage of the needle placement manipulator 51.

Figure 10A:
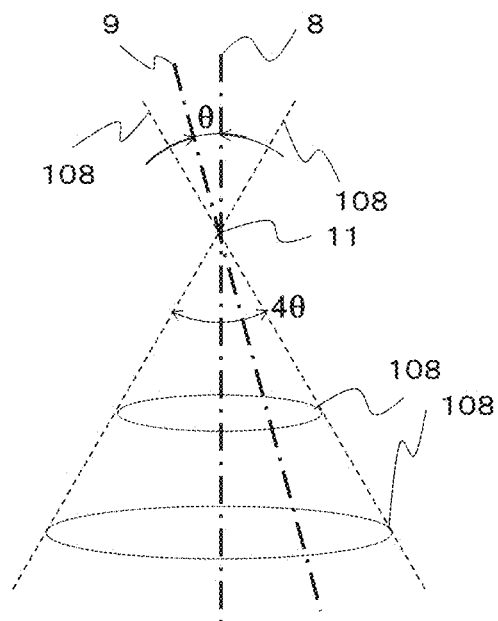
FIGS. 10A, 10B, and 10C are diagrams illustrating the coverage of the needle placement manipulator.

The basis for expanding the coverage of the needle placement manipulator 51 using the attachment 52 of the present disclosure will be described with reference to FIGS. 10A to 10C. FIG. 10A illustrates the initial coverage of the needle placement manipulator 51 without the use of the attachment 52. The initial coverage, which determined by rotating the first and second rotation guides 3 and 4 individually in the circumferential direction, is a conical region 108 enclosed by a dashed-line region with an apical angle of 4θ and with the remote center of motion 11 as a vertex, where θ is an angle formed by the axes 8 and 9 of the first and second rotation guides 3 and 4, respectively. That is, FIG. 10A shows the axis 8 and axis 9 of the rotation guides (3, 4) intersect at the remote center of motion (RCM: 11), and the rotation guides (3, 4) rotate to position the needle holder (5) such that the axis of the needle holder (insertion axis 5$a$) traces a conical region of coverage, the conical region of coverage having the apex thereof at the RCM 11 and the base thereof in a direction towards the subject of needle placement (14).

Figure 10B:
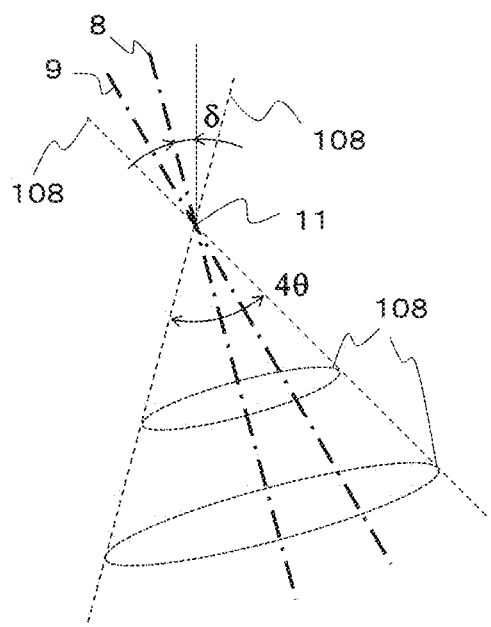
Figure 10C:
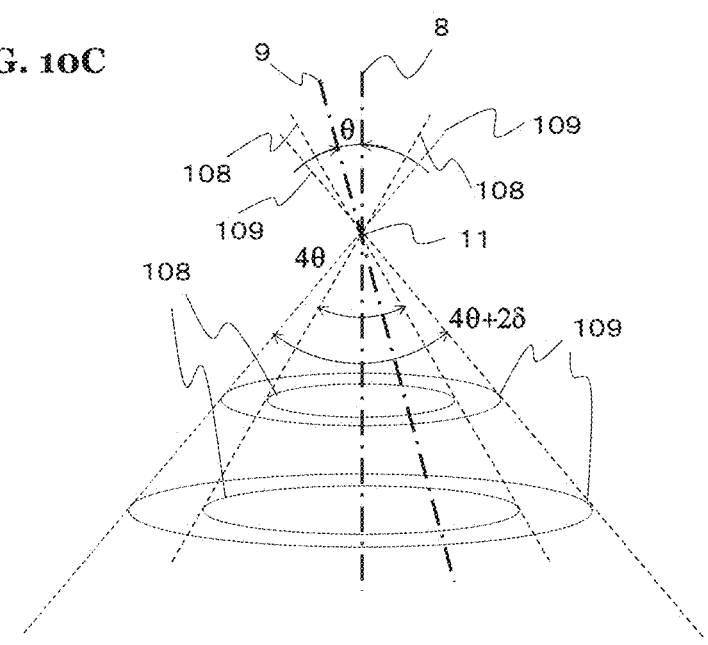

FIG. 10B illustrates a state in which the posture of the apparatus main body 1 is inclined (adjusted) by an angle δ using the attachment 52. In this state shown in FIG. 10B, the entire conical coverage 108 is inclined by the angle δ, as compared to the position shown in FIG. 10A. If the attachment 52 can incline the movable portion 54 by an angle δ across the entire circumferential region of the spherical guide 54$c$, the coverage of the needle placement manipulator 51 increases to a conical region 109 enclosed by the dashed line with an apical angle of 4θ+2δ and with the remote center of motion 11 as a vertex, as illustrated in FIG. 10C. As a result, the use of the attachment 52 effectively increases the coverage of the needle placement manipulator 51 to a conical range 4θ+2δ without changing the initial position of the apparatus main body 1 or the mount surface 53$a$ with respect to the patient, but rather by operating only the movable portion 54 along the spherical guide 53$c$, as illustrated by the arrows in FIG. 5B. Therefore, FIGS. 10B and 10C show how the guide portion (53$c$, 54$c$) changes the inclination of the rotary mechanism such that the axis of the needle holder intersects an insertion target (tissue 14) located outside of the initial conical region of coverage 108.

Figure 6:
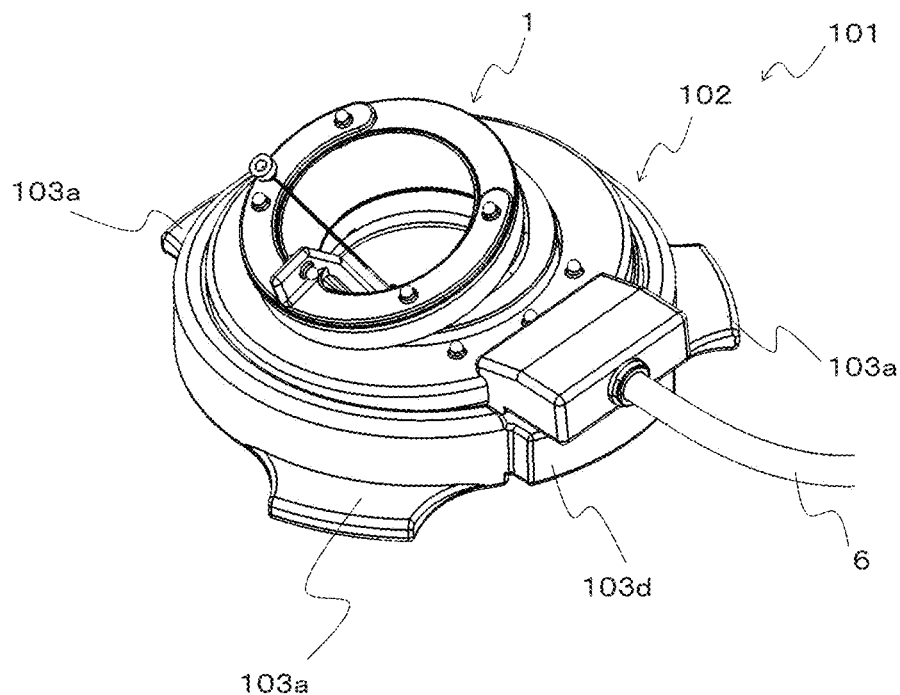
FIG. 6 is a schematic perspective view of a needle placement manipulator according to the first embodiment.
Figures 7A, 7B:
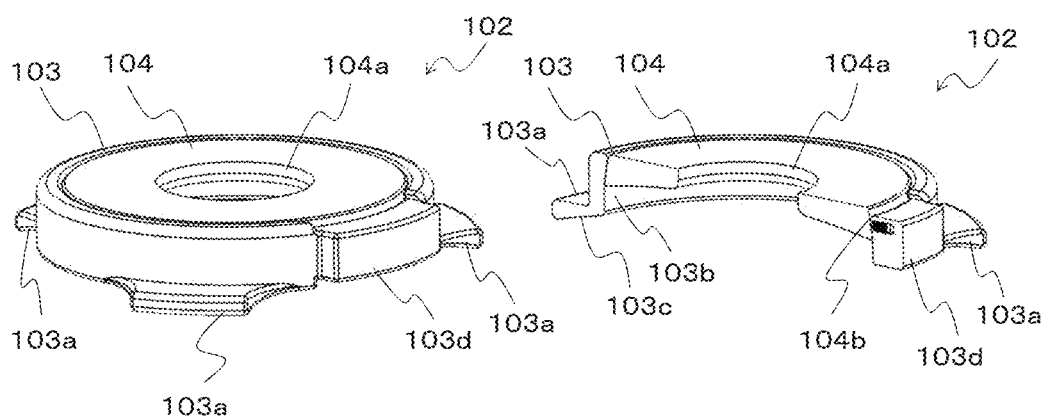
FIG. 7A is a schematic perspective view of an attachment according to the first embodiment.
FIG. 7B is a schematic perspective view of a cross section of the attachment.

The attachment 52 including the spherical guides 53$c$ and 54$c$ illustrated in FIG. 3 to FIGS. 5A and 5B is one exemplary illustration, which may be modified to have other configurations. The details of exemplary modifications will be described with reference to FIG. 6 to FIGS. 11A and 10. FIG. 6 is a schematic perspective view of a needle placement manipulator 101 including spherical guides of the present embodiment. FIG. 7A is a schematic perspective view of the attachment 102 excluding the apparatus main body 1, and FIG. 7B is a schematic perspective view of a cross section of the attachment 102. In FIG. 6, the attachment 102 is combined with the apparatus main body 1 to constitute the needle placement manipulator 101. In the drawings of FIGS. 7A and 7B, the attachment 102 includes a fixed portion 103 and a movable portion 104. The movable portion 104 includes a cylindrical fitting portion 104a configured to fit with the base body 2 of the apparatus main body 1. The fixed portion 103 includes an actuator unit 103d.

FIG. 8A is a cross-sectional view of the needle placement manipulator 101 taken along a cross section including the actuator unit 103d, and FIG. 8B is an enlarged view of a dashed-line region B. The fixed portion 103 includes a spherical guide 103b, and the movable portion 104 includes a spherical guide 104b. The movable portion 104 can change in posture along the spherical guide 103b relative to the fixed portion 103. In this case, the center of the spherical surfaces including the spherical guides 103b and 104b coincide with the remote center of motion (RCM) 11. The fixed portion 103 includes three mount portions 103a. The bottom of each mount portion 103a has a curved mount surface 103c (FIG. 8A) that follows the shape of the body surface of the patient to allow stable mounting. In the present embodiment, the bottom surface 2c of the base body 2 of the apparatus main body 1 can be fixed to the movable portion 104 to prevent the mutual interference between the apparatus main body 1 and the attachment 102 when the posture of the movable portion 104 is changed.

Next, a method for changing the posture of the movable portion 104 will be described with reference to FIGS. 8A and 8B. In the drawings, a layered piezoelectric element 105 is disposed in the actuator unit 103d. A hemispherical protrusion 106 is joined to an end of the layered piezoelectric element 105. The protrusion 106 is pushed against the spherical guide 104b by a compression coil spring 107 disposed in series with the layered piezoelectric element 105. When the layered piezoelectric element 105 is not energized, the posture of the movable portion 104 is fixed due to the friction between the protrusion 106 and the spherical guide 104b. When an alternating current voltage is applied to the layered piezoelectric element 105, the friction between the protrusion 106 and the spherical guide 104b is decreased to allow the movable portion 104 to be freely moved along the spherical guide 103b. Therefore, the actuator unit 103d effectively functions as brake (or a clutch) configured to brake (stop or inhibit) movement of the movable portion 104 relative to the fixed portion 103. The actuator unit 103d may also be referred to as a brake unit. To prevent the movable portion 104 from being detached from the fixed portion 103, for example, for example, when gravity acts on the attachment 102 vertically downward in the plane of the drawing, a spring, a wire, a magnet, or the like may be provided as appropriate to urge the movable portion 104 against the fixed portion 103.

FIGS. 9A and 9B illustrate simulated puncture of the target tissue 14 using the needle placement manipulator 101 placed on the patient's skin 15. In that case, the remote center of motion (RCM) 11 may be set on the skin 15, and the puncture point may not move regardless of the displacement (rotation) of the first and second rotation guides 3 and 4. FIG. 9A illustrates a state in which the intended target tissue 14 is out of coverage, so that the tip of needle 12 cannot be brought to the target tissue 14 even if the first and second rotation guides 103b and 104b are rotated. However, by changing the posture of the movable portion 104 using the attachment 102 of the present disclosure, the target tissue 14 can be brought within the coverage, so that the needle 12 can be brought to the target tissue 14, as illustrated in FIG. 9B. Whether the target tissue 14 is within the coverage of the apparatus main body 1 is determined using the following procedure, and the needle 12 is directed to the target tissue 14. After the posture of the movable portion 104 is determined, the actuator unit 103d is brought to a non-energized state to fix the movable portion 104. Subsequently, whether the coverage of the apparatus main body 1 includes the target tissue 14 is determined through calculation based on a CT image using the markers 16 provided on the apparatus main body 1, and if it is determined that the target tissue 14 is within the coverage, planning for bringing the needle 12 to the target tissue 14 is executed to displace the first and second rotation guides 3 and 4 to predetermined angles, thereby directing the needle 12 to the direction of the target tissue 14.

The manner of expanding the coverage of the needle placement manipulator 101 using the attachment 102 of the present disclosure will be described again with reference to FIGS. 10A to 10C. FIG. 10A illustrates the coverage of the needle placement manipulator 101. The coverage determined by rotating the first and second rotation guides 3 and 4 individually in the circumferential direction is a conical region 108 enclosed by a dashed-line region with an apical angle of 4θ and with the remote center of motion 11 as a vertex, where θ is an angle formed by the first and second rotation guides 3 and 4. FIG. 10B illustrates a state in which, when the posture of the apparatus main body 1 is inclined by an angle δ using the attachment 102, the conical coverage 108 is inclined by the angle δ. If the attachment 102 can incline the movable portion 104 by an angle δ across the entire circumferential region, the coverage of the needle placement manipulator 101 increases to a conical region 109 enclosed by the dashed line with an apical angle of 4θ+2δ and with the remote center of motion 11 as a vertex illustrated in FIG. 10C.

Figure 11A:
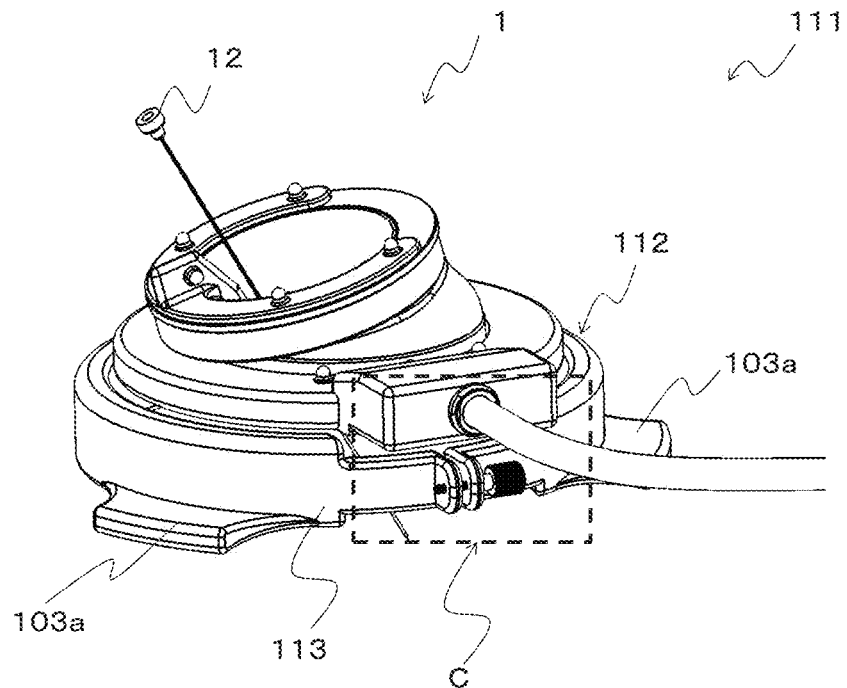
FIG. 11A is a schematic perspective view of a needle placement manipulator according to the first embodiment.
Figure 11B:
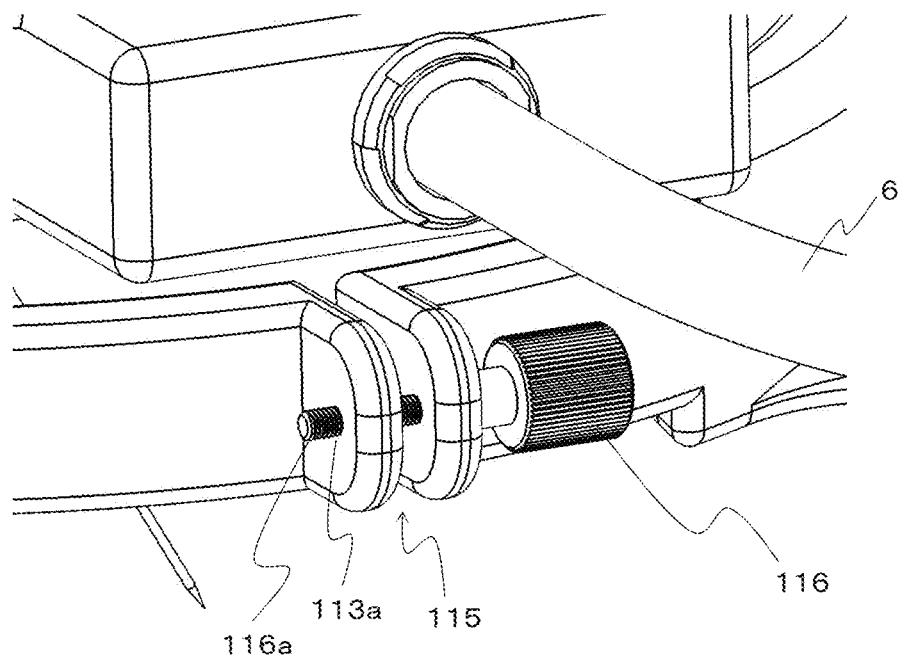
FIG. 11B is an enlarged view of a dashed-line region C in FIG. 11A.

Having described the configuration of the attachment 102 with the actuator unit 103d, the configuration illustrated in FIGS. 11A and 11B may be employed. FIG. 11A is a schematic perspective view of a needle placement manipulator 111, and FIG. 11B is an enlarged view of a dashed-line region C. Descriptions of components given the same reference signs will be omitted. In the drawings of FIGS. 11A and 11B, reference sign 112 denotes an attachment. In this case, the attachment 112 is combined with the apparatus main body 1 to constitute the needle placement manipulator 111. A fixed portion 113 of the attachment 112 has a clearance 115 at part in the circumferential direction and includes an internal thread 113a (internal threaded through hole) perpendicular to the clearance 115. The fixed portion 113 is configured such that the clearance 115 can be decreased by inserting an external thread 116a (a threaded stud) of a knurled knob 116 into the internal thread 113a. The knurled knob 116 provides a gripping surface for tightening or loosening the clearance 115. This configuration allows the posture of the movable portion 104 to be changed along the spherical guide by loosening the threads 113a and 116a and the posture of the movable portion 104 to be fixed by tightening the threads 113a and 116a. To prevent the movable portion 104 from being disengaged from the fixed portion 113, for example, when gravity acts on the attachment 112 vertically downward in the plane of the drawing, a spring, a wire, a magnet, or the like may be provided as appropriate to urge the movable portion 104 against the fixed portion 113.

In the present embodiment, even if it is found that the target tissue 14 is out of the coverage of the needle placement manipulator 111 after the needle placement manipulator 111 is placed on the body of the patient, the use of either the attachment 52, 102, or 112 combined with the apparatus main body 1 allows the coverage to be corrected by changing the posture of the movable portion 54 or 104. In other words, the posture of the needle placement manipulator 51, 101, or 111 can be changed so that the target tissue 14 falls within the necessary coverage. Changing the posture of the needle placement manipulator using the attachment described in the present embodiment eliminates the need to remove the attachment and the needle placement manipulator from the surface of the body of the patient when change in coverage is needed. This can omit troublesome treatment for maintaining the sterilized state of the attachment and the needle placement manipulator, leading to shorter operation time. The present embodiment enables not only to correct the coverage using the attachment so that the target tissue 14 falls within the coverage but also to change the posture using the attachment, with the target tissue included in the coverage, to prevent the interference between the bore of the imaging modality and the apparatus main body 1.

The present embodiment also has the effect of preventing the puncture point on the patient's skin set by planning from moving even if the posture is changed using the attachment by making the center of the spherical guides of the attachment and the remote center of motion to coincide at one point.

Although the present disclosure has been described as related to a needle placement manipulator whose apparatus main body has the remote center of motion (RCM) mechanism, it is to be understood that the apparatus main body need only include a guide for positioning the needle insertion axis and that the apparatus main body may have any configuration. It should also be understood that the workflow for determining whether the target tissue is within the coverage of the apparatus main body is given for mere illustration and that application of the present disclosure is not limited thereto.

Although the present embodiment has been described as applied to a configuration in which a piezoelectric actuator is used as the driving unit, and an optical encoder is used as the detecting unit, it is to be understood that the present disclosure is not limited thereto. Any other actuator and any other sensor may be respectively used as the driving unit and the detecting unit. The rotational displacement of the first and second rotation guides 3 and 5 may be manually adjusted without using an actuator and a sensor.

Although the present embodiment has been described using an example in which a layered piezoelectric element in the actuator unit is used to change the posture of the movable portion of the attachment, and the friction when changing the posture is reduced by applying an alternating voltage to the layered piezoelectric element to vibrate it, this is given for mere illustration. For example, by pushing an elastic member similar to the elastic member 20 against the spherical guide and applying an alternating voltage to the electromechanical energy transducer 22 firmly fixed to the elastic member to excite a standing wave on the contact surface of the elastic member, the same advantageous effect can be achieved. Furthermore, by increasing the number of elastic members for pressure, for example, by using three elastic members and generating a traveling wave on the contact surfaces of the elastic members, the movable portion of the attachment can be positioned at any posture along the spherical guide.

Although the present embodiment has been described using a CT scanner as a modality for visualization, the present disclosure is not limited thereto. For example, the present disclosure may be applied to the configuration of a nuclear magnetic resonance imaging (MRI) diagnostic apparatus. In this case, non-magnetic metal, resin, or ceramic may be used as a material of the needle placement manipulator and the attachment. In that case, a material of the markers may be a substance containing hydrogen atoms, such as an aqueous copper sulfate solution. In using the MRI, an RF coil for transmitting and receiving signals may be disposed below or in the vicinity of the attachment, as will be illustrated in the embodiments described below.

Although the present embodiment has been described as related to a configuration in which the center of the spherical guides coincides with the remote center of motion (RCM), the present disclosure is not limited to the configuration. The coverage correction range may be increased more without making the center of the spherical guides coincide with the remote center of motion (RCM), as illustrated in fourth and fifth embodiments described below.

Second Embodiment

Referring to FIGS. 7A and 7B and FIGS. 12 to 15B, a second embodiment of the present disclosure will be described. Where the same components as those of the above-described embodiment are given the same reference signs, detailed descriptions thereof will be omitted. In the present embodiment, an X-ray computed tomography (CT) scanner is used to visualize the inside of the body, medical devices, medical-device guide devices, etc.

Figure 12:
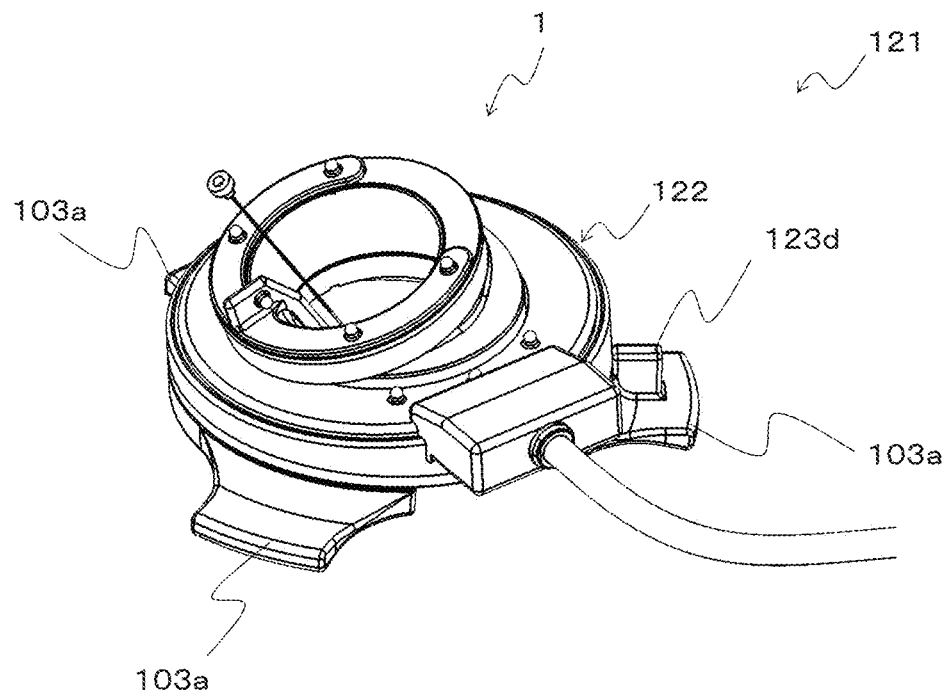
FIG. 12 is a schematic perspective view of a needle placement manipulator according to a second embodiment of the present disclosure.
Figure 13:
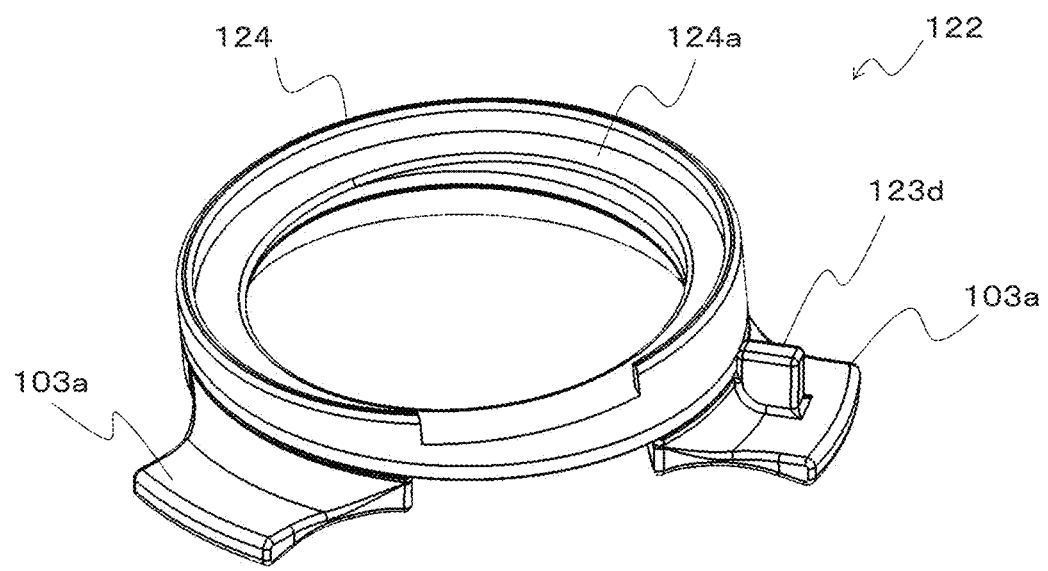
FIG. 13 is a schematic perspective view of an attachment according to the second embodiment.
Figure 14A:
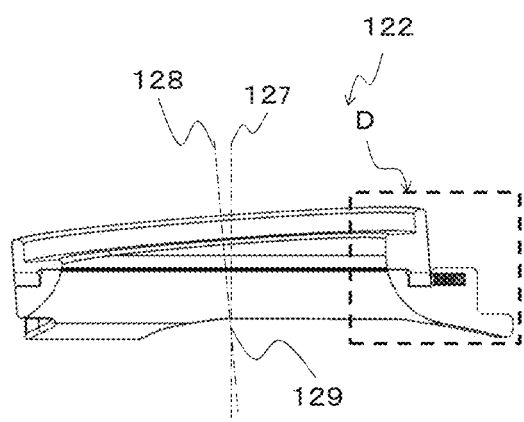
FIG. 14A is a schematic cross-sectional view of the attachment 122.
Figure 14B:
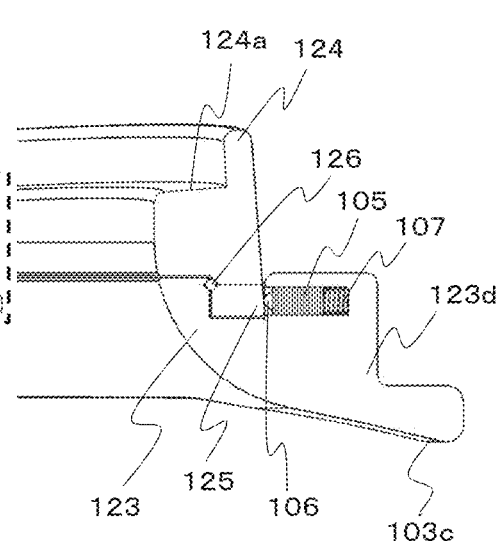
FIG. 14B is an enlarged view of a dashed-line region D in FIG. 14A.

FIG. 12 is a schematic perspective view of a needle placement manipulator 121 according to a second embodiment of the present disclosure. The configuration of the apparatus main body 1 of the needle placement manipulator 121 is the same as the configuration of the above-described first embodiment. In the present embodiment, an attachment 122 is combined with the apparatus main body 1 to constitute the needle placement manipulator 121. FIG. 13 is a schematic perspective view of the attachment 122 single body. FIG. 14A is a schematic cross-sectional view of the attachment 122 taken along a plane passing through an actuator unit 123d provided at the attachment 122. FIG. 14B is an enlarged view of a dashed-line region D in FIG. 14A. In the drawings, the attachment 122 includes a fixed portion 123 and a movable portion 124, as in the first embodiment, and the fixed portion 123 includes three mount portions 103a. The movable portion 124 is configured to rotate relative to the fixed portion 123 with a rotatable bearing arranged therebetween, as described below. Between the fixed portion 123 and the movable portion 124, a plurality of balls 126 are disposed in the circumferential direction along a groove to constitute a bearing by bonding a fastener member 125 to the movable portion 124 after the balls 126 are disposed in the groove. The use of the bearing allows the movable portion 124 and the fastener member 125 to smoothly rotate about a rotational axis 127 more than 360 degrees without wobbling movement. The movable portion 124 includes a ring-shaped holding portion 124a. By fitting the base body 2 of apparatus main body 1 on the holding portion 124a, the apparatus main body 1 can be fixed to the movable portion 124. The ring-shaped holding portion 124a is inclined (or is configured to be inclined) at a predetermined angle δ relative to the horizontal plane, and the central axis 128 of the holding portion 124a intersects the rotational axis 127 at an intersection point to form a remote center of motion (RCM) 129. The remote center of motion 129 of the attachment 122 may coincide with the remote center of motion 11 of the apparatus main body 1.

The fixed portion 123 includes an actuator unit 123d. In the actuator 123d, a hemispherical protrusion 106 is pushed against the side of the fastener member 125 by a piezoelectric element 105 and a compression coil spring 107. While the layered piezoelectric element 105 is not energized, the posture of the movable portion 124 is fixed due to the friction between the protrusion 106 and the fastener member 125. When an alternating current voltage is applied to the layered piezoelectric element 105, the friction between the protrusion 106 and the fastener member 125 is decreased to allow the movable portion 124 to be rotated about the rotational axis 127 via the bearing.

Figure 15A:
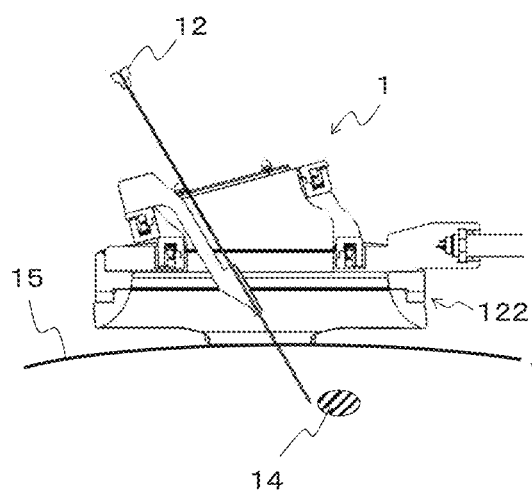
FIGS. 15A and 15B are schematic cross-sectional views of the needle placement manipulator illustrating simulated puncture.
Figure 15B:
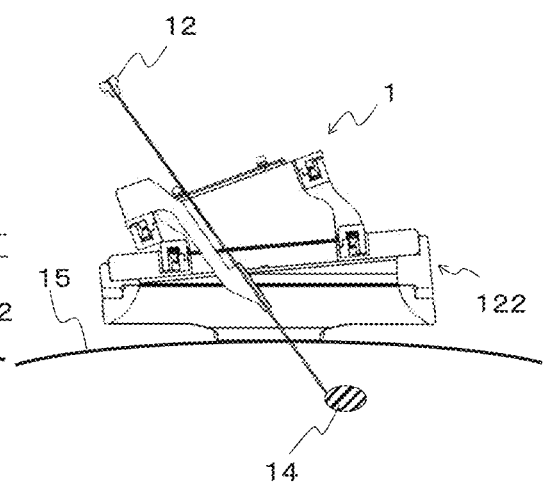

FIGS. 15A and 15B illustrate simulated puncture of the target tissue 14 using the needle placement manipulator 121 placed on the patient's skin 15. In this case, the remote center of motion (RCM) 11 may be set on the skin 15, and the remote center of motion (RCM) 129 may or may not coincide with RCM 11, but the puncture point may not move regardless of the displacement of the first and second rotation guides 3 and 4. FIG. 15A illustrates a state in which the intended target tissue 14 is out of coverage, so that the tip of needle 12 cannot be brought to the target tissue 14 even if the first and second rotation guides 103b and 104b are rotated to a maximum inclination. However, by changing the posture of the movable portion 124 using the attachment 122 of the present disclosure, the target tissue 14 can be brought within the coverage, so that the needle 12 can be brought to the target tissue 14, as illustrated in FIG. 15B. A method for determining whether the target tissue 14 is within the coverage of the apparatus main body 1 is the same as the method of the first embodiment, and a detailed description thereof will be omitted.

The coverage of the needle placement manipulator 121 can be expanded by using the attachment 122 of the present disclosure, as in the first embodiment. The use of the attachment 122 expands the coverage to the conical region 109 enclosed by the dashed line with the remote center of motion 11 as a vertex and with an apical angle 4θ+2δ, as illustrated in FIG. 10C.

In the present embodiment, even if it is found that the target tissue 14 is out of the coverage of the needle placement manipulator 121 after the needle placement manipulator 121 is placed on the body of the patient, the combined use of the attachment 122 and the apparatus main body 1 allows the coverage to be corrected by rotating the movable portion 124 to change the posture of the apparatus main body 1. In other words, the posture of the needle placement manipulator 121 can be changed so that the target tissue 14 falls within the coverage. Changing the posture of the needle placement manipulator 121 using the attachment 122 described in the present embodiment eliminates the need to remove the attachment 122 and the needle placement manipulator 121 from the surface of the body of the patient when change in coverage is needed. This allows the sterilized state of the attachment 122 and the needle placement manipulator 121 to be kept, leading to shorter operation time. The present embodiment enables not only to correct the coverage using the attachment 122 so that the target tissue 14 falls within the coverage but also to change the posture using the attachment 122 to prevent, for example, the interference between the bore and the apparatus main body 1.

The present embodiment also has the effect of preventing the puncture point on the patient's skin set by planning from moving even if the posture is changed using the attachment by making the center of the spherical guides of the attachment and the remote center of motion coincide.

Although the present disclosure has been described as related to a needle placement manipulator whose apparatus main body has the remote center of motion (RCM) mechanism, it is to be understood that the apparatus main body need only include a guide for positioning the needle insertion axis and that the apparatus main body may have any configuration.

It should also be understood that the workflow for determining whether the target tissue is within the coverage of the apparatus main body is given for mere illustration and that application of the present disclosure is not limited thereto.

Although the present embodiment has been described as applied to a configuration in which a piezoelectric actuator is used as the driving unit, and an optical encoder is used as the detecting unit, it is to be understood that the present disclosure is not limited thereto. Any other actuator and any other sensor may be respectively used as the driving unit and the detecting unit. The rotational displacement of the first and second rotation guides may be manually adjusted without using an actuator and a sensor.

Although the present embodiment has been described using an example in which a layered piezoelectric element in the actuator unit is used to change the posture of the movable portion of the attachment, and the friction when changing the posture is reduced by applying an alternating voltage to the layered piezoelectric element to vibrate it, this is given for mere illustration. For example, a unit similar to the piezoelectric actuator illustrated in FIG. 2B may be used to rotate the movable portion about the rotational axis 127.

Although the present embodiment has been described using a CT scanner as a modality for visualization, the present disclosure is not limited thereto. For example, the present disclosure may be applied to the configuration of a nuclear magnetic resonance imaging (MRI) diagnostic apparatus. In this case, non-magnetic metal, resin, or ceramic may be used as a material of the needle placement manipulator and the attachment. In that case, a material of the markers may be a substance containing hydrogen atoms, such as an aqueous copper sulfate solution. In using the MRI, an RF coil for transmitting and receiving signals may be disposed below or in the vicinity of the attachment, as will be illustrated in the embodiments described below.

Although the present embodiment has been described as related to a configuration in which the center of the spherical guides coincides with the remote center of motion (RCM), the present disclosure is not limited to the configuration. The coverage correction range may be increased more without making the center of the spherical guides coincide with the remote center of motion (RCM), as illustrated in fourth and fifth embodiments described below.

Third Embodiment

Referring to FIGS. 7A and 7B and FIGS. 16A to 18B, a third embodiment of the present disclosure will be described. The same components as those of the above-described embodiment are given the same reference signs, and detailed descriptions thereof will be omitted. In the present embodiment, a nuclear magnetic resonance imaging diagnostic apparatus (MRI) is used to visualize the inside of the body, medical devices, medical-device guide devices, etc.

In the present embodiment, an example in which two attachments 133 and 134, respectively illustrated in FIGS.

16A and 16B, are used will be described. The attachments 133 and 134 respectively include ring-shaped holding portions 133a and 134a. By inserting the apparatus main body 1 into the holding portions 133a and 134a, the apparatus main body 1 can be fixed to the attachments 133 and 134. The holding portion 133a is formed parallel to the horizontal plane, and the holding portion 134a is formed so as to be inclined at a predetermined angle δ with respect to the horizontal plane. That is, the holding portion 134a is formed so as to be slanted at a predetermined angle δ with respect to the horizontal plane of the attachment 134. The holding portions 133a and 134a may be formed so that the central axis of each pass through the remote center of motion (RCM) 11 of the apparatus main body 1.

Figure 16A:
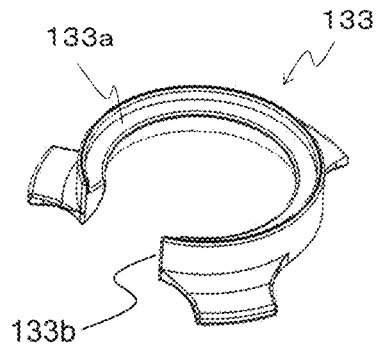
FIG. 16A is a schematic perspective view of a first attachment according to a third embodiment of the present disclosure.
Figure 16B:
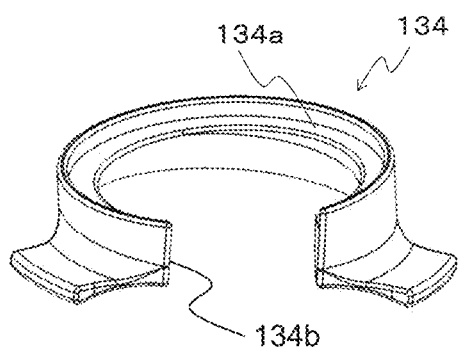
FIG. 16B is a schematic perspective view of a second attachment according to the third embodiment.
Figure 16C:
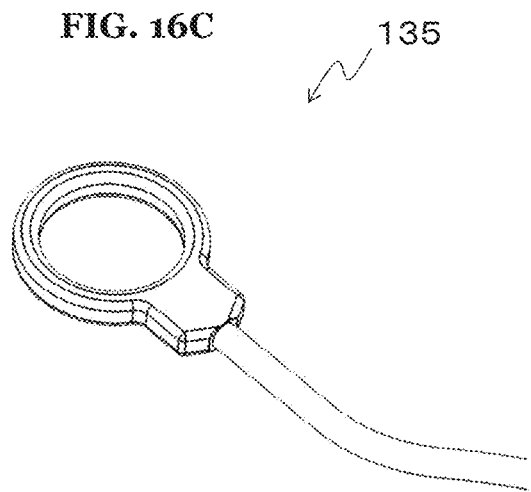
FIG. 16C is a schematic perspective view of a single loop coil.

In using an MRI modality, an RF coil for amplifying the signals is used to acquire clear images. FIG. 16C is a schematic perspective view of an exemplary single loop coil 135, which is a kind of RF coil. The single loop coil 135 is a kind of surface coil to be placed over the body surface of the object to be imaged. To accommodate the surface coil 135, the attachment 133 includes a notched opening 133b and the attachment 134 includes a notched opening 134b respectively.

Figure 17A:
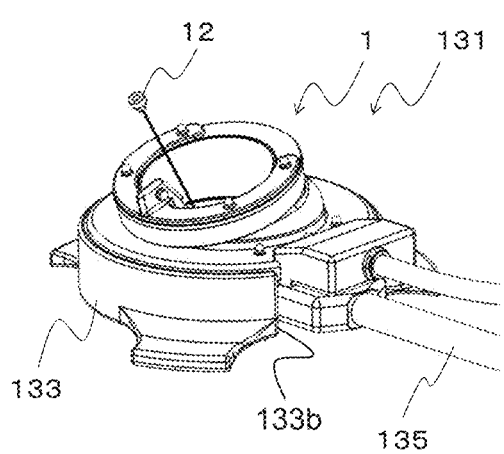
FIG. 17A is a schematic perspective view of a first needle placement manipulator of the third embodiment.
Figure 17B:
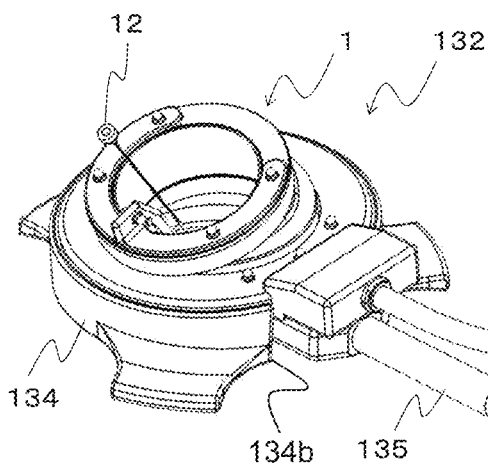
FIG. 17B is a schematic perspective view of a second needle placement manipulator of the third embodiment.

FIGS. 17A and 17B are schematic perspective views of needle placement manipulators 131 and 132 including the attachments 133 and 134, respectively, according to the third embodiment. The configuration of the apparatus main bodies 1 of the needle placement manipulators 131 and 132 are the same as the configuration of the above-described embodiments. In the present embodiment, the attachments 133 and 134 are each combined with the apparatus main body 1 to constitute the needle placement manipulators 131 and 132, respectively.

FIGS. 18A and 18B respectively illustrate simulated puncture of the target tissue 14 using the needle placement manipulators 131 and 132 and the attachments 133 and 134 placed on the patient's skin 15. In using the MRI for visualization, the single loop coil 135 is first positioned and fixed on the patient's skin 15 with tape or a belt to acquire a sharp image of the target site. After completion of the fixation of the single loop coil 135, the apparatus main body 1 is fixed on the body of the patient using the attachment 133, as illustrated in FIG. 18A. In this case, the remote center of motion (RCM) 11 of the main body 1 may be set on the skin 15, and the puncture point may not move regardless of displacement of the first and second rotation guides 3 and 4. However, in FIG. 18A, the intended target tissue 14 is not within coverage, so that the tip of needle 12 cannot be brought to the target tissue 14 even if the first and second rotation guides 3 and 4 are rotated. In that case, the needle placement manipulator 131 is removed, and the attachment 134 is newly placed on the single loop coil 135 fixed to the skin 15. Then, planning for bringing the needle 12 to the target tissue 14 is performed on the basis of the posture of the apparatus main body 1 detected using the markers 16, and when it is determined that the target tissue 14 is within the coverage, the first and second rotation guides 3 and 4 are displaced to predetermined positions to direct the needle 12 to the target tissue 14. In the present embodiment, by shifting from the attachment 133 to the attachment 134 to change the posture of the apparatus main body 1, the target tissue 14 can fall within the coverage, allowing the needle 12 to reach the target tissue 14, as illustrated in FIG. 18B. The coverage of the needle placement manipulator can be corrected using the attachment 134 of the present disclosure, as in the first embodiment, under the same principles illustrated in FIGS. 10A and 10B.

In the present embodiment, even if it is found that the target tissue 14 is out of the coverage of the needle placement manipulator 131 or 132 after the needle placement manipulator 131 or 132 is placed on the body of the patient, the combined use of the attachment 133 or 134 and the apparatus main body 1 allows the coverage to be corrected by replacing the attachment to correct the coverage without removing the RF coil. In other words, the posture of the needle placement manipulator can be changed so that the target tissue 14 falls within the coverage without removing the RF coil. Changing the posture of the needle placement manipulator using the attachment 133 or 134 described in the present embodiment eliminates the need to remove the RF coil from the surface of the body of the patient when change in coverage is needed. This prevents degradation of the quality of the MRI image due to movement of the RF coil and eliminates the need to position the RF coil again, leading to shorter operation time. The present embodiment enables not only to correct the coverage using the attachment 133 or 134 so that the target tissue 14 falls within the coverage but also to change the posture using the attachment 133 or 134 to prevent, for example, the interference between the bore and the apparatus main body 1.

The present embodiment allows the position and posture of the apparatus main body 1 to be determined without interference with the RF coil without adding significant design changes to the apparatus main body 1 by preparing attachments matching the apparatus main body 1 and various RF coils to set the remote center of motion (RCM) to an intended position.

The present embodiment also has the effect of preventing the puncture point on the patient's skin set by planning from moving even if the posture is changed by selecting an attachment so that the central axis of the mount portions of the attachment passes through the remote center of motion of the apparatus main body 1.

In addition, in the present embodiment, the attachment is formed as a single component, so that the attachment can be manufactured at low cost by, for example, injection molding of a resin material. The low-cost manufacture allows the attachment to be a disposal component, which makes it possible to omit preoperative sterilization work etc., contributing to improving surgical quality.

Although the present embodiment has been described as related to a needle placement manipulator whose apparatus main body has a remote center of motion (RCM) mechanism, it is to be understood that the apparatus main body has only to include a guide for positioning the insertion axis of the needle and that the apparatus main body may have any configuration.

It should also be understood that the workflow for determining whether the target tissue is within the coverage of the apparatus main body is given for mere illustration and that application of the present disclosure is not limited thereto.

In the present embodiment, an example in which the coverage is changed by changing the attachment has been described. However, the coverage may be changed using a single attachment, as in the embodiments described below.

Although the present embodiment has been described using an MRI as a modality for visualization, the present disclosure is not limited thereto. For example, the present disclosure may easily be applied to the configuration of a computed tomography (CT) scanner.

Although the present embodiment has a configuration in which the central axes of the holding portions 133a and 134a pass through the remote center of motion (RCM) 11 of the apparatus main body 1, the present disclosure is not limited thereto. The coverage correction range can also be increased without passing the central axes of the holding portions 133a and 134a through the remote center of motion (RCM) of the apparatus main body 1.

Fourth Embodiment

Referring to FIGS. 19 to 24, a fourth embodiment of the present disclosure will be described. The same components as those of the above-described embodiment are given the same reference signs, thus detailed descriptions thereof will be omitted. In the present embodiment, a nuclear magnetic resonance imaging diagnostic apparatus (MRI) is used to visualize the inside of the body, medical devices, medical-device guide devices, etc.

Figure 19:
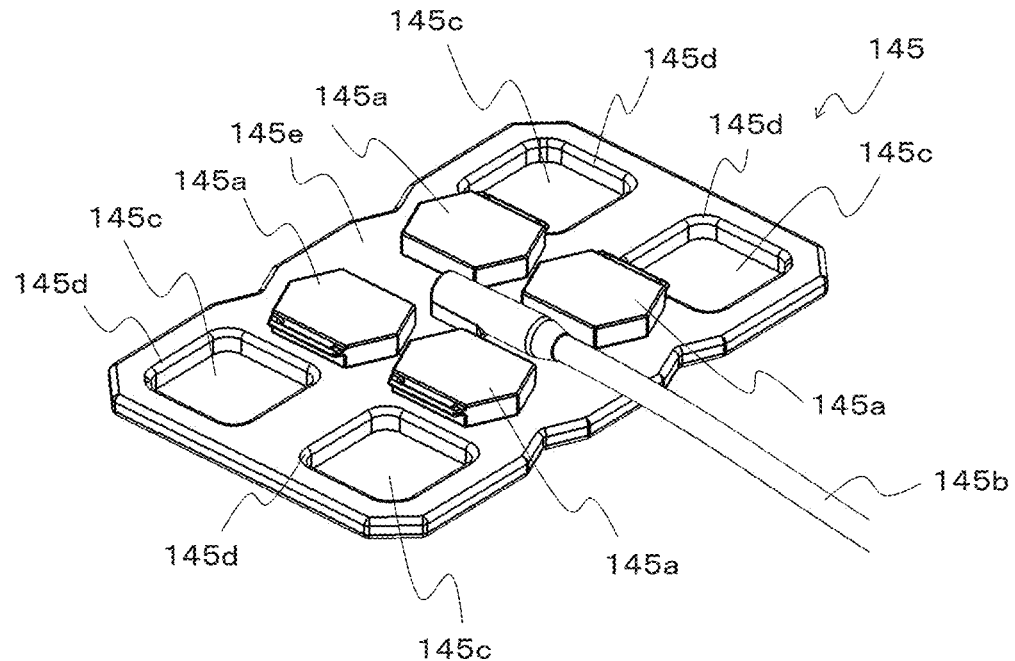
FIG. 19 is a schematic perspective view of a phased array coil according to a fourth embodiment of the present disclosure.
Figure 20:
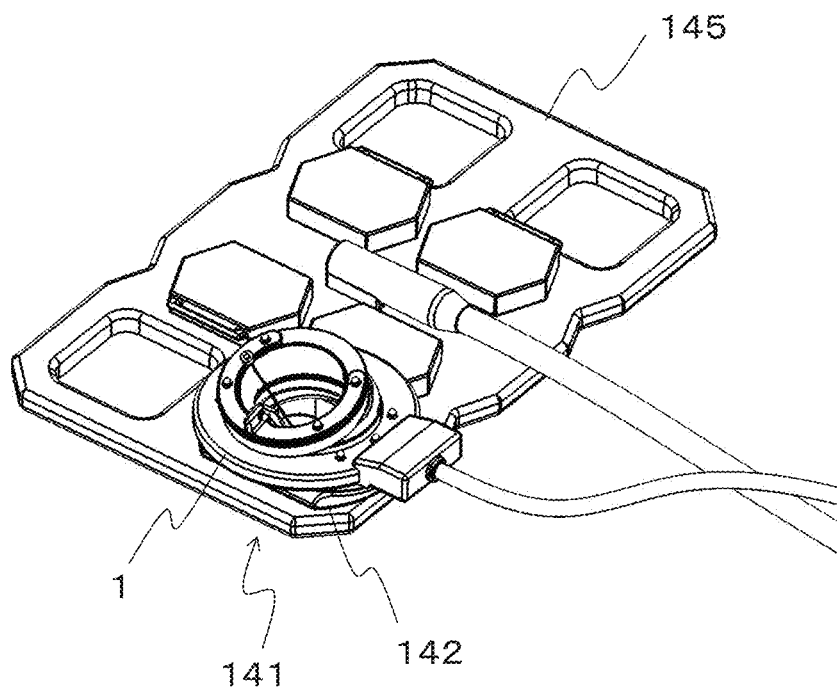
FIG. 20 is a schematic perspective view of a phased array coil disposed on the phased array coil.

In the present embodiment, an example in which a phased array coil 145 is used as an RF coil for amplifying the signals in order to obtain a clearer image in using MRI will be described. It is known that a phased array coil can improve the signal-to-noise ratio (SNR) of MR images by combining a plurality of small coils to increase the number of channels, as compared with the surface coil described in the third embodiment. FIG. 19 is a schematic perspective view of the phased array coil 145. The phased array coil 145 has four openings 145c, whose edges 145d are rectangular. The phased array coil 145 includes processing units 145a that process RF signals and a cable 145b for signal transmission and reception. FIG. 20 is a schematic perspective view of the phased array coil 145 illustrating a state in which a needle placement manipulator 141 is disposed in the opening 145c. In the present embodiment, an attachment 142 is combined with the apparatus main body 1 to constitute the needle placement manipulator 141 configured or adapted to be attached to the phased array coil 145.

Figure 21A:
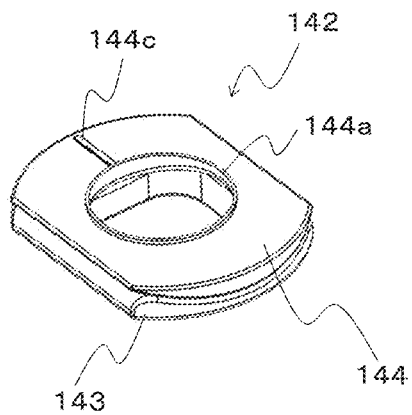
FIGS. 21A, 21B, and 21C are schematic perspective views of an attachment according to the fourth embodiment.
Figure 21B:
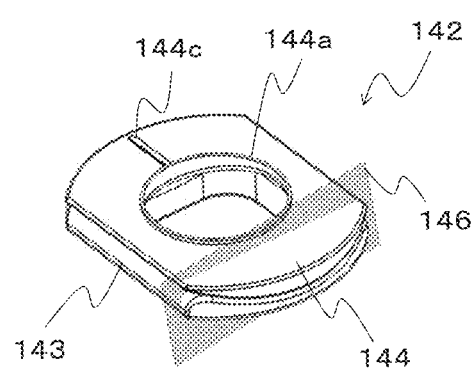
Figure 21C:
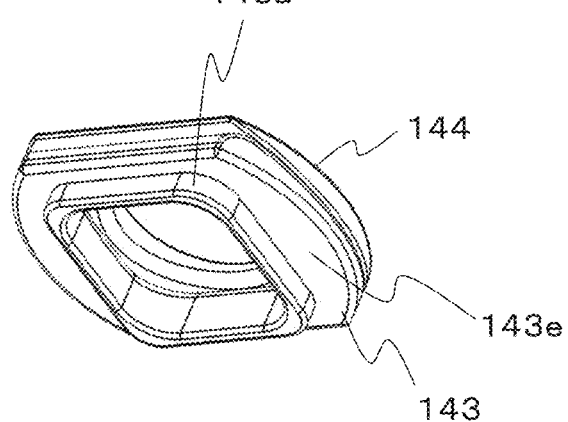

Referring to FIG. 19 and FIGS. 21A to 21C, the details of the attachment 142 will be described. FIGS. 21A and 21B are schematic perspective views of the attachment 142, as viewed from a direction in which the apparatus main body 1 is attached thereto. FIG. 21C is a schematic perspective view of the attachment 142, as viewed from the back (from a direction opposite to the direction in which the apparatus main body 1 is attached thereto). The attachment 142 includes a fixed portion 143 and a movable portion 144. As shown in FIG. 21C, the fixed portion 143 has a protruding portion 143a extending perpendicularly to a mount surface 143e. The attachment 142 can be positioned with respect to the phased array coil 145 by fitting the protruding portion 143a to the edge 145d. An adhesive material (e.g. tape) may be provided on the mount surface 143e of the fixed portion 143 so that the mount surface 143e can be temporarily bonded to a surface 145e of the phased array coil 145 during needle placement operation. The movable portion 144 has an axial fitting portion 144a (cylindrical fitting portion) and at least one ridge key 144c. The groove 2b provided on the bottom of the apparatus main body 1 is fitted to the ridge key 144c, and the hole-like (cylindrical) fitting portion 2a provided in base of the apparatus main body 1 is fitted to the axial fitting portion 144a of the movable portion 144, so that the apparatus main body 1 can be mounted to the attachment 142.

Figure 22A:
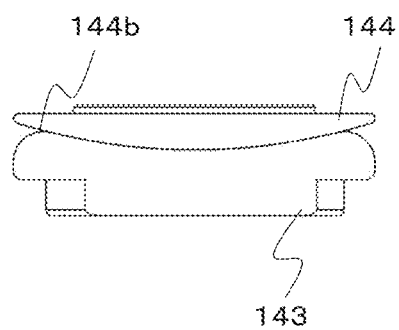
FIGS. 22A and 22B are schematic cross-sectional views of the attachment.
Figure 22B:
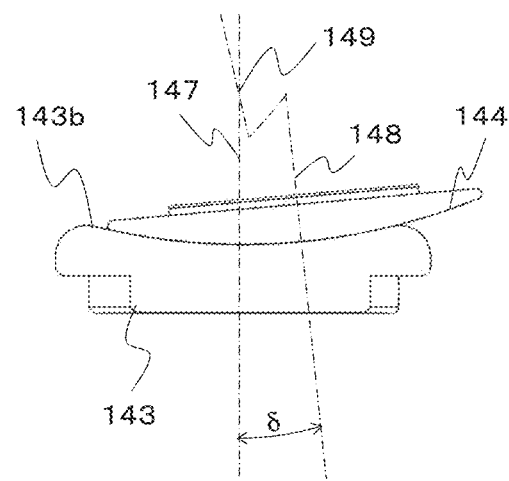

FIGS. 22A and 22B are schematic cross-sectional views of the attachment 142 taken along a plane 146 in FIG. 21B. The fixed portion 143 and the movable portion 144 respectively include cylindrical surfaces that serve as cylindrical guides 143b and 144b. In this manner, the cylindrical surface of movable portion 144 can slide along the cylindrical guide 143b of fixed portion 143. The center line 147 of the fixed portion 143 and the center line 148 of the movable portion 144 respectively correspond to central planes of the cylindrical guides 143b and 144b. When the cylindrical surface of movable portion 144 (cylindrical guide 144b) slides along the cylindrical guide 143b the center line 148 can be bidirectionally displaced by a predetermined angle δ with respect to the center line 147 centering on a central axis 149. The posture of the movable portion 144 may be fixed using a layered piezoelectric element or a knurled knob mechanism, as those described in the previous embodiments.

FIGS. 23A and 23B illustrate simulated puncture of the target tissue 14 using the needle placement manipulator 141 placed on the patient's skin 15. In using an MRI modality for visualization, the phased array coil 145 is first positioned and fixed on the patient's skin 15 with a tape or band to acquire a sharp image of a target site. After completion of the fixation of the phased array coil 145, the apparatus main body 1 is fixed on the body of the patient using the attachment 142. In a case as shown in FIG. 23A, the target tissue 14 is not within coverage, so that the tip of needle 12 cannot be brought to the target tissue 14 even if the first and second rotation guides 3 and 4 are rotated. In that case, for the apparatus main body 1 and the attachment 142, the movable portion 144 is slid along the cylindrical guide 143b to the position illustrated in FIG. 23B. Then, planning for bringing the needle 12 to the target tissue 14 is performed on the basis of the posture of the apparatus main body 1 detected using the markers 16, and when it is determined that the target tissue 14 is within the coverage, the first and second rotation guides 3 and 4 are displaced to predetermined positions to direct the needle 12 to the target tissue 14. In the present embodiment, by changing the posture of the apparatus main body 1 using the movable portion 144 of attachment 142, the target tissue 14 can fall within the coverage, as illustrated in FIG. 23B.

FIG. 24 illustrates the coverage of the needle placement manipulator 141 with the attachment 142 of the present embodiment. In the present embodiment, since the remote center of motion 11 of the apparatus main body and the central axis 149 of the cylindrical guide 144b are offset, the remote center of motion 11 moves along an arcuate path 150 (cylindrical locus) as the movable portion 144 moves two-directionally with respect to the fixed portion 143. Therefore, the conical coverage 108 also moves bidirectionally by an angle δ as the remote center of motion 11 moves. That is, the conical coverage 108 can be adjusted along a curved locus (arcuate path 150).

In the present embodiment, even if it is found that the target tissue 14 is out of coverage of the needle placement manipulator 141 after the needle placement manipulator 141 is placed on the body of the patient, the combined use of the attachment 142 and the apparatus main body 1 allows the coverage to be corrected without removing the RF coil by sliding the movable portion 144 of the attachment 142 along the cylindrical guide 143b. In other words, the posture of the needle placement manipulator 141 can be changed so that the target tissue 14 falls within the coverage. Changing the posture of the needle placement manipulator 141 using the attachment 142 described in the present embodiment eliminates the need to remove the RF coil from the surface of the body of the patient when change in coverage is needed. This prevents degradation of the quality of the MRI image due to movement of the RF coil and eliminates the need to position the RF coil again, leading to shorter operation time. The present embodiment enables not only to correct the coverage using the attachment 142 so that the target tissue 14 falls within the coverage but also to change the posture using the attachment 142 to prevent, for example, the interference between the bore of the imaging modality and the apparatus main body 1. In addition, the present embodiment can enable positioning the needle 12 to the same target tissue 14 from different directions which is effective in multiple-needle puncture planning.

In the present embodiment, the amount of movement of the coverage can be increased as compared with the above-described embodiments by offsetting (moving) the central axis 149 with respect to the remote center of motion 11. The present embodiment allows the position and posture of the apparatus main body 1 to be determined without interference with the RF coil without adding significant design changes to the apparatus main body 1 by preparing attachments matching the apparatus main body 1 and various RF coils to set the remote center of motion (RCM) to an intended position.

Although the present embodiment has been described as related to a needle placement manipulator whose apparatus main body has a remote center of motion (RCM) mechanism, it is to be understood that the apparatus main body has only to include a guide for positioning the insertion axis of the needle and that the apparatus main body may have any configuration. It should also be understood that the workflow for determining whether the target tissue is within the coverage of the apparatus main body is given for mere illustration and that application of the present disclosure is not limited thereto.

Although the present embodiment has been described using an MRI as a modality for visualization, the present disclosure is not limited thereto. For example, the present embodiment may easily be applied to the configuration of a computed tomography (CT) scanner or an ultrasound imaging modality.

Although the present embodiment is an example configuration in which the remote center of motion (RCM) 11 of the apparatus main body 1 does not come to the central axis of the guide, the present disclosure is not limited to the configuration. An attachment similar to those of the other embodiments may be used so that the remote center of motion (RCM) of the apparatus main body 1 is disposed on the central axis of the cylindrical guide. Although a method for changing the posture of the movable portion using a cylindrical guide has been described, a spherical guide may be used as in the above-described embodiments. Notably, in the case of using spherical guides (instead of cylindrical guides), the coverage of the needle placement manipulator 141 using the attachment 142 can be increased omni-directionally by an angle δ as the conical coverage 108 could move more than 360 degrees around the conical coverage 108 while being centered on the central axis 149.

Fifth Embodiment

Referring to FIGS. 25 to 30, a fifth embodiment of the present disclosure will be described. The same components as those of the above-described embodiments are given the same reference signs, and detailed descriptions thereof will be omitted. In the present embodiment, an X-ray computed tomography (CT) scanner is used to visualize the inside of the body, medical devices, medical-device guide devices, etc.

Figure 25:
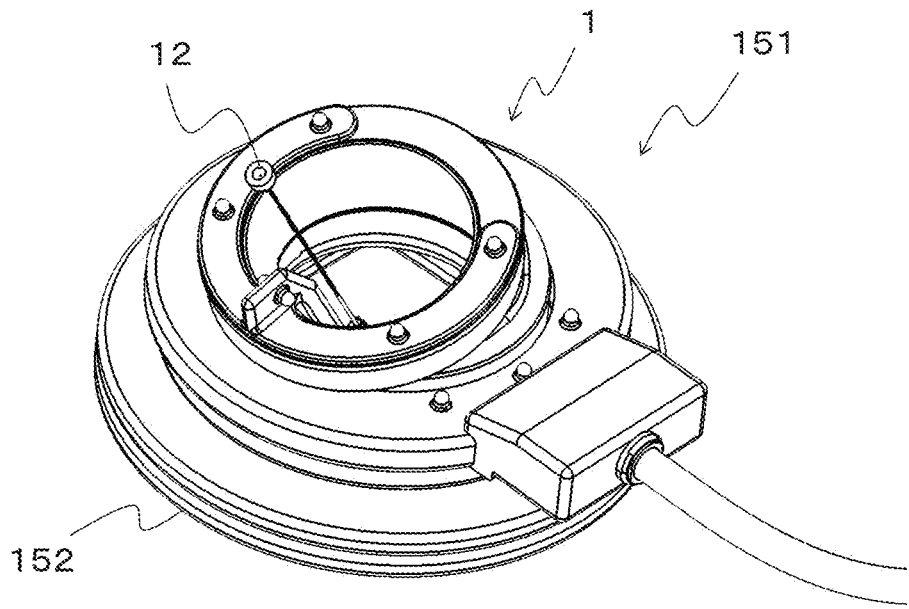
FIG. 25 is a schematic perspective view of a needle placement manipulator according to a fifth embodiment of the present disclosure.
Figure 26A:
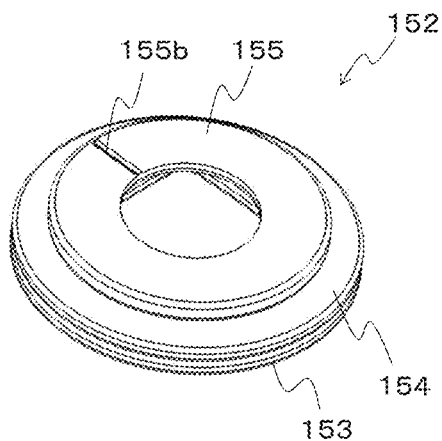
FIGS. 26A and 26B are schematic perspective views of an attachment of the fifth embodiment.
Figure 26B:
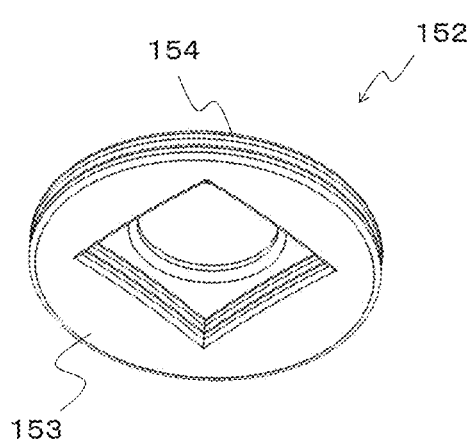

FIG. 25 is a schematic perspective view of a needle placement manipulator 151 of a fifth embodiment of the present disclosure. The configuration of the apparatus main body 1 of the needle placement manipulator 151 is the same as the configuration of the above-described embodiments. In the present embodiment, an attachment 152 is combined with the apparatus main body 1 to constitute the needle placement manipulator 151. FIGS. 26A and 26B are schematic perspective views of the attachment 152 as viewed from two different sides (top and bottom views). The attachment 152 includes three components, a fixed portion 153, a first movable portion 154, and a second movable portion 155. The second movable portion 155 includes a ridge key 155b on the top surface thereof. As in the above-described embodiments, the groove 2b provided on the bottom of the apparatus main body 1 is fitted to the ridge key 155b so that the apparatus main body 1 can be mounted and fixed to a predetermined position. The bottom of the fixed portion 153 has a curved mounting surface 153a with smooth spherical shape to keep a stable mount condition by conforming to the contour shape of a patient's body.

Figure 27A:
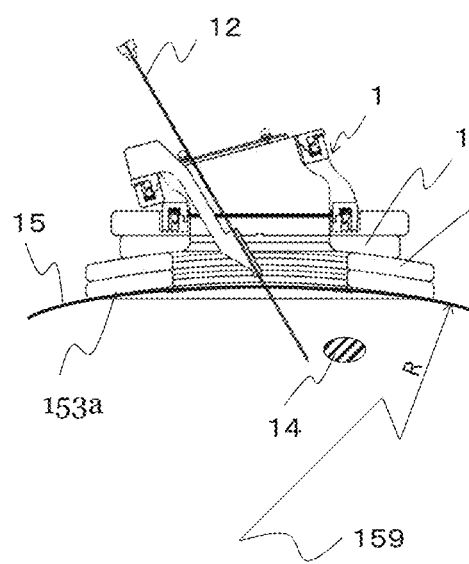
FIGS. 27A and 27B s are schematic cross-sectional views of the needle placement manipulator illustrating simulated puncture.
Figure 27B:
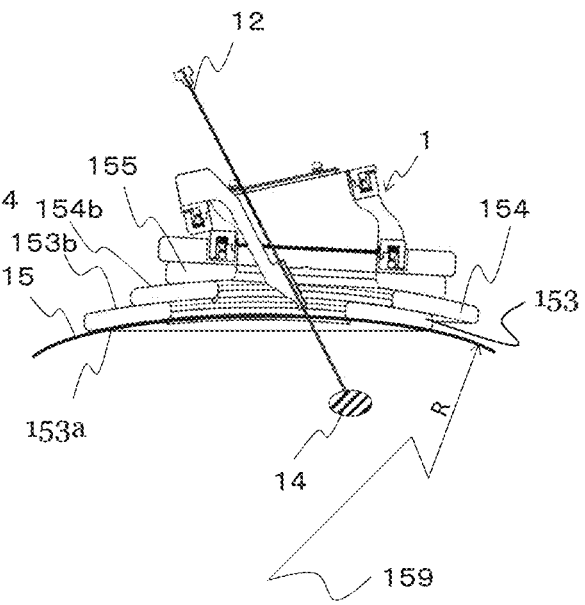
Figure 28A:
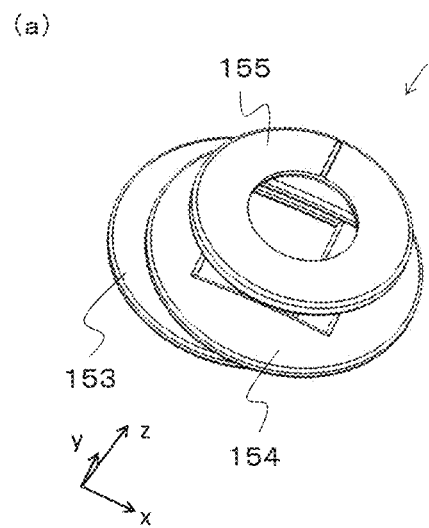
FIG. 28A is a schematic perspective view of the attachment.
Figure 28B:
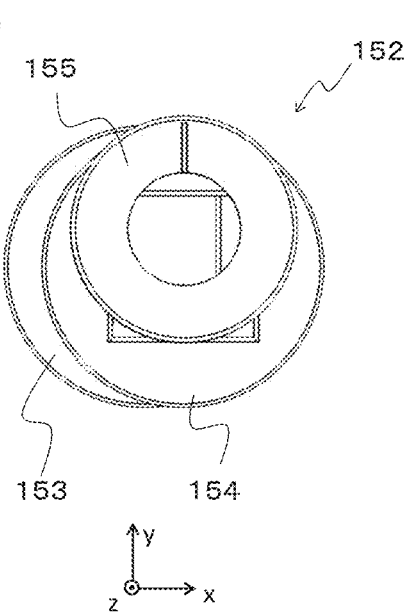
FIG. 28B is a schematic plan view of the attachment.

Next, referring to FIG. 27A to FIG. 30, the structure of attachment 152 and the functions of the first movable portion 154 and the second movable portion 155 will be described in detail. The axes of coordinates are common among the drawings. FIGS. 27A and 27B schematically illustrate a state of puncturing the target tissue 14 using the needle placement manipulator 151 placed on the patient's skin 15, in which the human skin 15 is approximately treated as a spherical surface having a radius R centered on a point 159. FIG. 28A is a schematic perspective view of the attachment 152, and FIG. 28B is a schematic plan view of the attachment 152 (observed in the direction in which the apparatus main body 1 is attached thereto).

In the drawings, the contact portion between the fixed portion 153 and the first movable portion 154 is provided with a guide 153b having a spherical shape centered on the point 159 and slidable about a spherical surface having an axis passing through the point 159 and parallel to the z-axis. The guide 153b is on a spherical surface having a radius (R+t), where t is the distance between the patient's surface skin 15 and the guide 153b. In the drawings, the contact portion between the first movable portion 154 and the second movable portion 155 is provided with a guide 154b having a spherical shape centered on the center 159 and slidable about a spherical surface having an axis passing through the center 159 and parallel to the z-axis. The guide 154b is on a spherical surface having a radius of (R+t+s), where s is the distance between the first guide 153b and the second guide 154b.

In FIGS. 27A and 27B, the remote center of motion (RCM) 11 of the apparatus main body 1 may be set on the skin 15 by setting (t+s) to an appropriate size. FIG. 27A illustrates a state in which the target tissue 14 is out of coverage, so that the tip of needle 12 cannot be brought to the target tissue 14 even if the first and second rotation guides 3 and 4 are rotated. However, the target tissue 14 can be put in the coverage by changing the posture of the first movable portion 154 using the attachment 152 of the present disclosure, allowing the needle 12 to reach the target tissue 14, as illustrated in FIG. 27B. A method for determining whether the target tissue 14 is within the coverage of the apparatus main body 1 is the same as the method of the first embodiment, and a detailed description thereof will be omitted. The first movable portion 154 and the second movable portion 155 can be moved manually or with any actuator, as described in the above embodiments. This also applies to fixation.

Figure 29A:
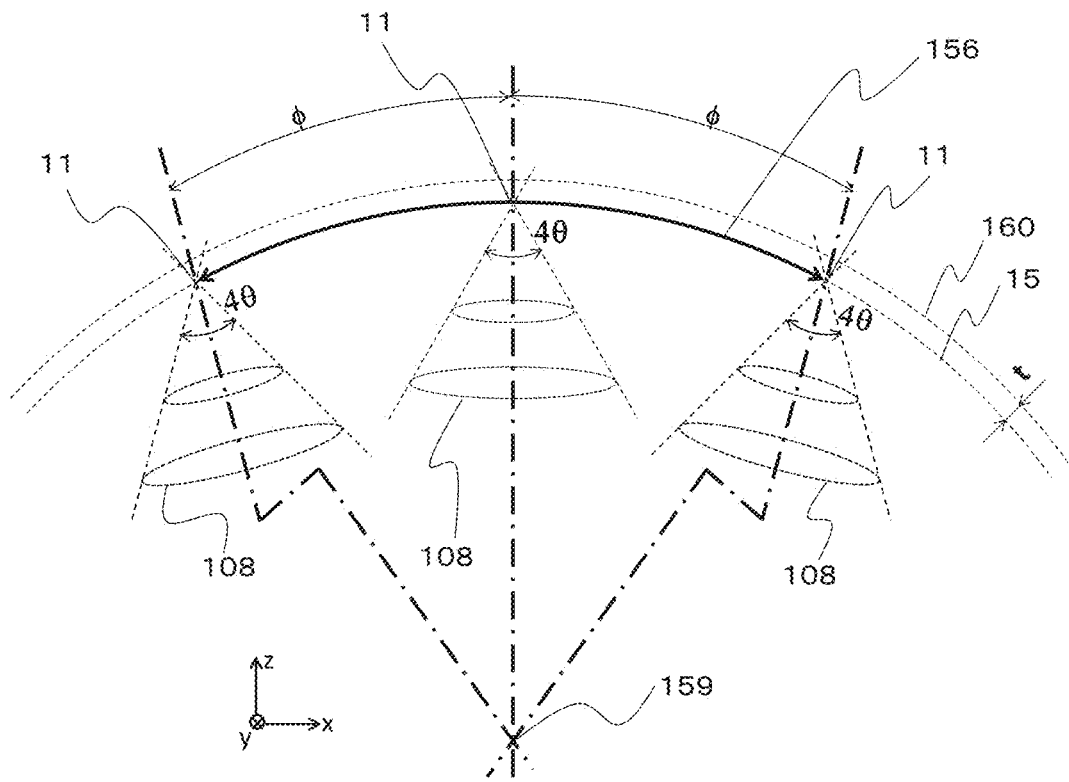
FIGS. 29A and 29B are diagrams illustrating the coverage of the needle placement manipulator.
Figure 29B:
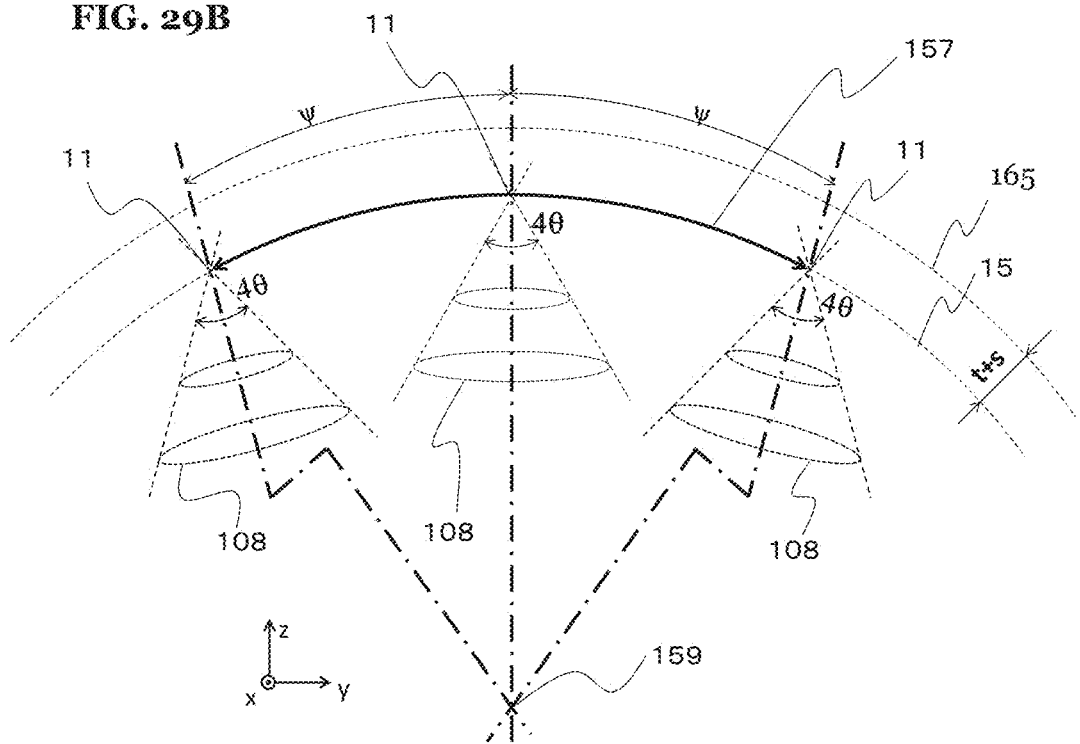
Figure 30:
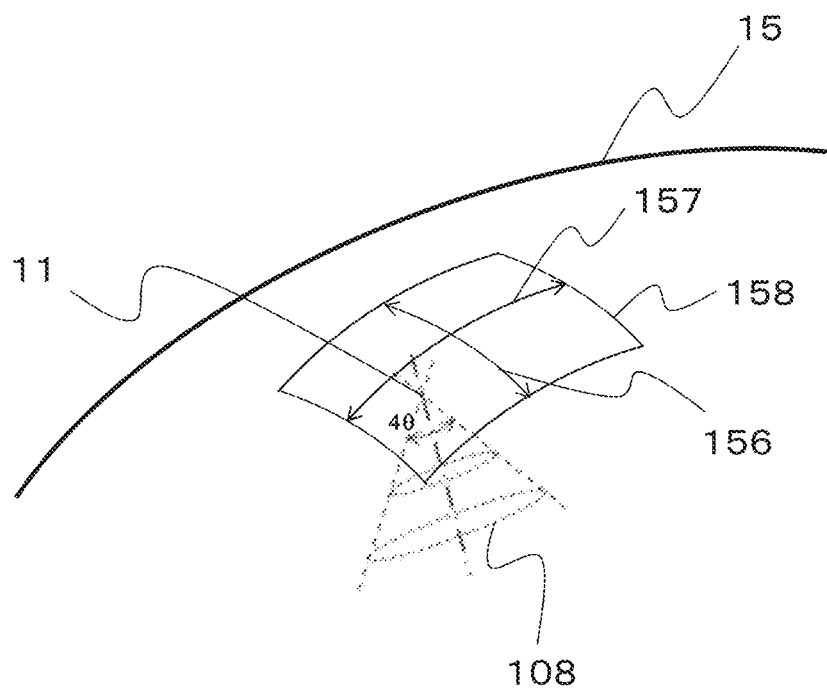
FIG. 30 is a diagram illustrating the coverage of the needle placement manipulator.

The coverage of the needle placement manipulator 151 of the present embodiment will be described. FIG. 29A is a diagram illustrating the effect of coverage expansion due to the movement of the first movable portion 154. In the drawing of FIG. 29A, the guide 153b slides bidirectionally by an angle ±4 on a spherical plane (spherical locus) 160 with a radius (R+t) centered on the point 159. As the remote center of motion 11 slides along an arcuate path in a range 156 on the skin 15, the conical coverage 108 with the remote center of motion 11 as a vertex and with an apical angle 4θ also moves along the arcuate path. FIG. 29B is a diagram illustrating the effect of coverage expansion due to the movement of the second movable portion 155. In the drawing, the guide 154b slides bidirectionally by an angle ±φ on a spherical plane (spherical locus) 165 with a radius of (R+t+s) centered on the point 159. Accordingly, as the remote center of motion 11 moves in a range 157 on the skin 15, the conical coverage 108 with the remote center of motion 11 as the vertex and with an apical angle 4θ also moves along an arcuate path with range 157. FIG. 30 illustrates the moving range of the conical coverage 108 based on the combined ranges described above. Since the first and second movable portions 154 and 155 respectively move along spherical loci 160 and 165 that are perpendicular to each other, the coverage 108 can be moved to any position within the region enclosed by a line 158 as the remote center of motion 11 slides in the ranges 156 and 157 on the skin 15.

In the present embodiment, even if it is found that the target tissue 14 is out of coverage of the needle placement manipulator 151 after the needle placement manipulator 151 is secured onto the body of the patient, the combined use of the attachment 152 and the apparatus main body 1 allows the coverage to be corrected by sliding the first and/or second movable portions 154 and 155 to change the posture of the apparatus main body 1. In other words, the posture of the needle placement manipulator 151 can be changed so that the target tissue 14 falls within the coverage. Since the remote center of motion 11 of the apparatus main body 1 can be moved to a position in the range 158 on the spherical plane, the coverage expansion range is larger than those in the previous embodiments. Changing the posture of the needle placement manipulator 151 using the attachment 152 described in the present embodiment eliminates the need to remove the attachment 152 and the needle placement manipulator 151 from the surface of the body of the patient when change in coverage is needed. This allows the sterilized state of the attachment 152 and the needle placement manipulator 151 to be kept, leading to improvement of the safety of surgery. The present embodiment enables not only to correct the coverage using the attachment 152 so that the target tissue 14 falls within the coverage but also to change the posture using the attachment 152 to prevent, for example, the interference between the bore of the imaging modality and the apparatus main body 1.

The present embodiment also has the effect of preventing the puncture point on the patient's skin set by planning from moving even if the posture is changed using the attachment by forming the guide of the attachment so that the remote center of motion 11 of the apparatus main body 1 moves on the skin 15. Moreover, present embodiment can have the effect of allowing the performance of more than one puncture operation within the range 158 without having to remove and reattach the manipulator.

Although the present disclosure has been described as related to a needle placement manipulator whose apparatus main body has the remote center of motion (RCM) mechanism, it is to be understood that the apparatus main body need only include a guide for positioning the needle insertion axis and that the apparatus main body may have any configuration.

It should also be understood that the workflow for determining whether the target tissue is within the coverage of the apparatus main body is given for mere illustration and that application of the present disclosure is not limited thereto.

Although the present embodiment has been described as applied to a configuration in which a piezoelectric actuator is used as the driving unit, and an optical encoder is used as the detecting unit, it is to be understood that the present disclosure is not limited thereto. Any other actuator and any other sensor may be respectively used as the driving unit and the detecting unit. The rotational displacement of the first and second rotation guides may be manually adjusted without using an actuator and a sensor.

In the present embodiment, the patient's skin 15 is approximated to a spherical plane, and the guides 153b and 154b are described as a spherical surface having the same center as the sphere of the skin 15. However, the present disclosure is not limited to the configuration. For example, the centers of the spheres that the skin 15, the guide 153b, and the guide 154b form may differ or the radii of the spheres may differ. Instead of the spherical guides, a guide having any curved shape that matches the specific shape of the patient's body may be produced to allow the needle placement manipulator to be more precisely placed. In addition, a cylindrical guide or a straight (planar) guide may be used instead of the spherical guides, which may reduce manufacturing costs.

In the present embodiment, the attachment includes two movable portions. However, the attachment may have one movable portion having a movable range of two degrees of freedom. A configuration that allows posture change with multiple degrees of freedom is also possible by using three or more movable portions.

Although the present embodiment has been described using a CT scanner as a modality for visualization, the present disclosure is not limited thereto. For example, the present disclosure may be applied to the configuration of a nuclear magnetic resonance imaging (MRI) diagnostic apparatus. In this case, non-magnetic metal, resin, or ceramic may be used as a material of the needle placement manipulator and the attachment. In that case, a material of the markers may be a substance containing hydrogen atoms, such as an aqueous copper sulfate solution. In using the MRI, an RF coil for transmitting and receiving signals may be disposed below or in the vicinity of the attachment, as will be illustrated in the embodiments described below.

Sixth Embodiment

Referring to FIGS. 31A to 34D, a sixth embodiment of the present disclosure will be described. The same components as those of the above-described embodiment are given the same reference signs, and detailed descriptions thereof will be omitted. In the present embodiment, a nuclear magnetic resonance imaging diagnostic apparatus (MRI) is used to visualize the inside of the body, medical devices, medical-device guide devices, etc.

Figure 31A:
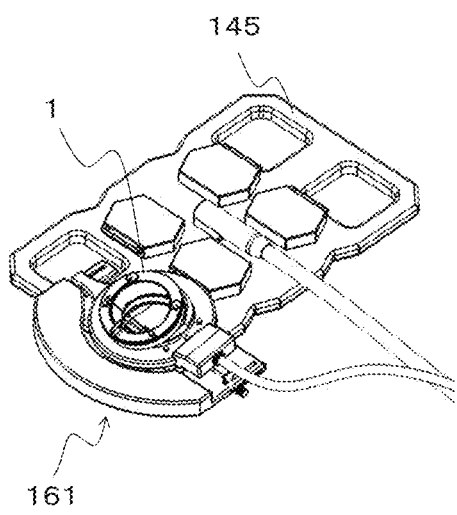
FIG. 31A is a schematic perspective view of a needle placement manipulator disposed on a phased array coil according to a sixth embodiment of the present disclosure.
Figure 31B:
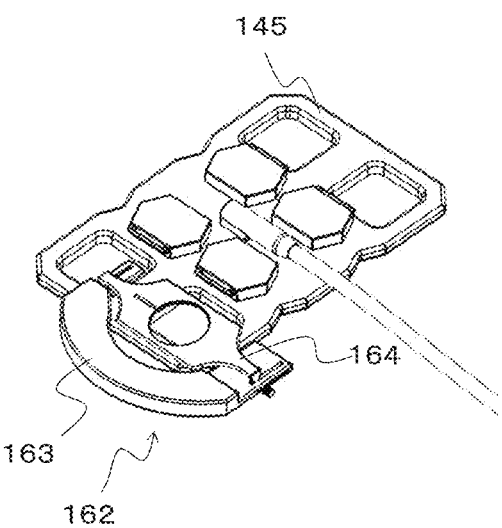
FIG. 31B is a schematic perspective view of the needle placement manipulator disposed on the phased array coil according to the sixth embodiment.

In the present embodiment, an example in which a phased array coil 145 is used as an RF coil in order to obtain a clearer image in using an MRI modality will be described. FIG. 31A is a schematic perspective view of a needle placement manipulator 161 disposed in an opening 145c of the phased array coil 145. In the present embodiment, an attachment 162 is combined with the apparatus main body 1 to constitute the needle placement manipulator 161.

Referring to FIGS. 31A to 33D, the details of the attachment 162 will be described. FIG. 32A is a schematic perspective view of the attachment 162, and FIG. 32B is a schematic perspective view of the attachment 162 as viewed from the back. FIGS. 32C and 32D are respective enlarged views of dashed-line regions E and F in FIG. 32A. The attachment 162 includes a fixed portion 163 and a movable portion 164. The fixed portion 163 has a recessed portion 163d on the back, so that the attachment 162 can be positioned and fixed to the phased array coil 145 by fitting the recessed portion 163d to the edge 145d.

Figure 32A:
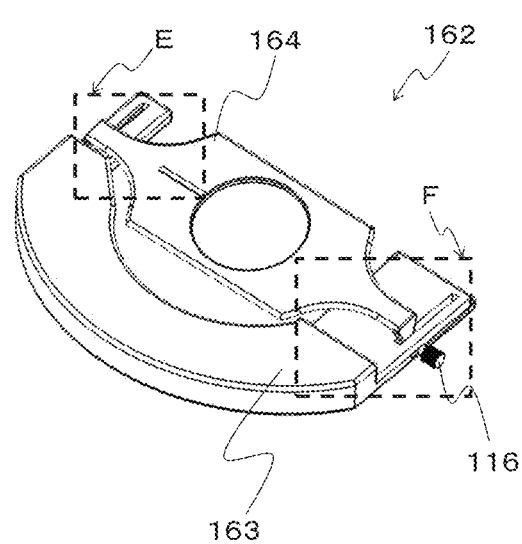
FIGS. 32A and 32B are schematic perspective views of the attachment.
Figure 32B:
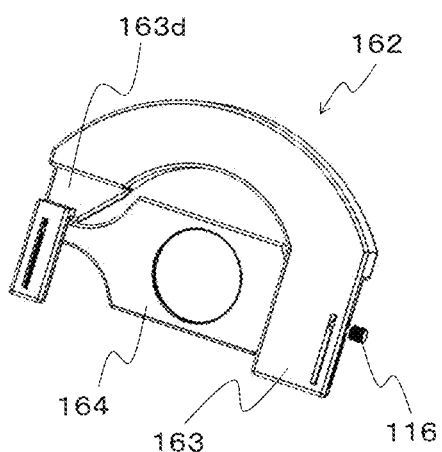
Figure 32C:
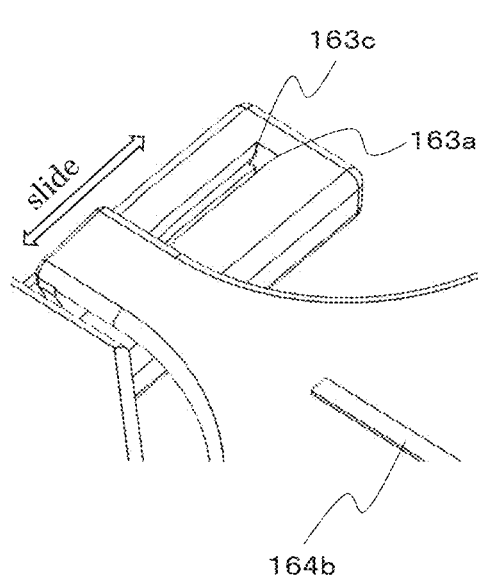
FIG. 32C is an enlarged view of a dashed-line regions E in FIG. 32A.
Figure 32D:
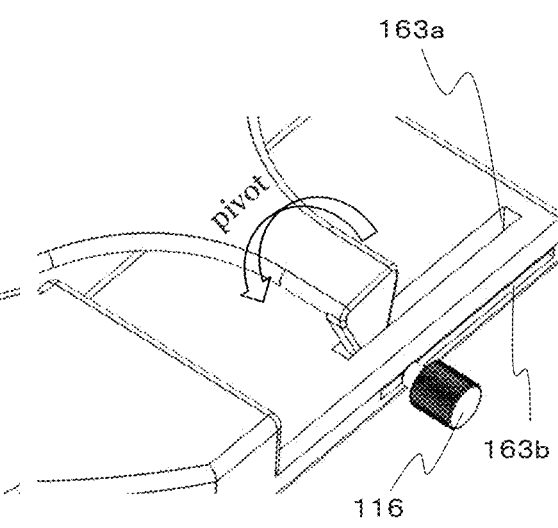
FIG. 32D is an enlarged view of a dashed-line regions F in FIG. 32A.
Figure 33A:
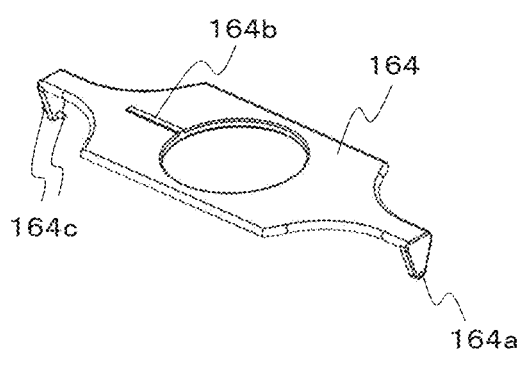
FIGS. 33A and 33B are schematic perspective views of a movable portion of the sixth embodiment.
Figure 33B:
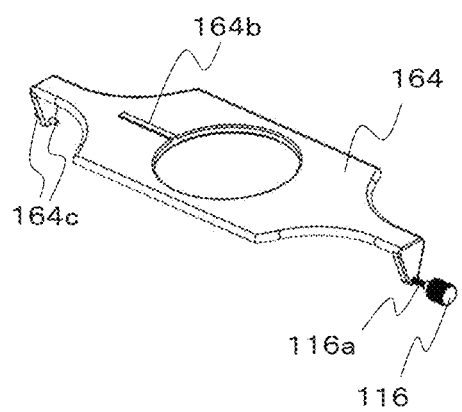

FIG. 33A is a schematic perspective view of the movable portion 164. The movable portion 164 has a ridge key 164b. The groove 2b provided on the bottom of the apparatus main body 1 is fitted to the ridge key 164b, so that the position and posture of the apparatus main body 1 relative to the attachment 162 can be fixed. As illustrated in FIG. 33B, the movable portion 164 has an internal thread 164a at one end, to which an external thread 116a of a knurled knob 116 can be attached. The movable portion 164 has a columnar slider 164c (in the shape of a cylindrical pin) at the other end. The needle placement manipulator 161 is configured such that the attachment 162 is formed so that the remote center of motion (RCM) 11 of the apparatus main body 1 is on a straight line connecting the center of the internal thread 164a and the center of the slider 164c. Referring to FIGS. 32C and 32D, the fixed portion 163 has a clearance 163a for sliding the movable portion 164, a clearance 163b for sliding the knurled knob 116, and a rail 163c for guiding the slider 164c. Thus, the attachment 162 has a mechanism in which the movable portion 164 can slide along the rail 163c and can rotate (pivot) about the straight line connecting the center of the internal thread 164a and the center of the slider 164c with two degrees of freedom; see "slide" and "pivot" arrows in FIGS. 32C and 32D, respectively. Therefore, the attachment 162 can change the position and posture of the apparatus main body 1 while the remote center of motion (RCM) 11 of the apparatus main body 1 is kept on the skin 15 or keeps the distance from the skin 15 constant by loosening the external thread 116a and the internal thread 164a, and can keep the position and posture by tightening the knurled knob 116 to lock the movable portion 164 at a desired position and posture.

FIGS. 34A to 34D illustrate simulated puncture of the target tissue 14 using the needle placement manipulator 161 placed on the patient's skin 15. In using the MRI modality for visualization, the phased array coil 145 is first positioned and fixed on the patient's skin 15 with a tape or band to acquire a sharp image of the target site. After completion of the fixation of the phased array coil 145, the apparatus main body 1 is fixed on the body of the patient using the attachment 162. In FIG. 34A, the target tissue 14 is not within coverage, so that the tip of needle 12 cannot be brought to the target tissue 14 even if the first and second rotation guides 3 and 4 are rotated. In that case, for the apparatus main body 1 and the attachment 162, the movable portion 164 is rotated (pivoted) about the central axis of the slider 164c, as illustrated in FIG. 34B. Then, planning for bringing the needle 12 to the target tissue 14 is performed on the basis of the posture of the apparatus main body 1 detected using the markers 16, and when it is determined that the target tissue 14 is within the coverage, the first and second rotation guides 3 and 4 are displaced to predetermined positions to direct the needle 12 to the target tissue 14. In the present embodiment, the coverage can be further expanded by sliding the movable portion 164 rightwards in the plane of the drawing along the rail 163c, as illustrated in FIGS. 34C and 34D. For example, by sliding the movable portion 164 along the rail 163c while keeping the posture illustrated in FIG. 34B, a new target tissue 14 can be put in the coverage, as illustrated in FIG. 34C. Furthermore, for example, by sliding the movable portion 164 along the rail 163c while keeping the posture illustrated in FIG. 34B, the target tissue 14 at the same position as in the FIG. 34B, as illustrated in FIG. 34D, can be positioned from different directions by rotating the first and second rotation guides 3 and 4.

In the present embodiment, by changing the posture of the apparatus main body 1 using the attachment 162, the target tissue 14 can fall within the coverage, and the needle 12 can be brought to the target issue 14, as illustrated in FIGS. 34B, 34C, and 34D. Furthermore, by increasing the degree of freedom of the movable portion 164, positioning to the target tissue 14 from different directions can be performed. This allows planning for the target tissue 14 excluding human tissue, such as bones, which should not be hurt by the needle 12, if included in the puncture path. In addition, positioning the needle 12 to the same target tissue 14 from different directions is also effective in multiple-needle puncture therapy for expanding a frozen region (ice ball) at the leading end of the needle 12 in freezing therapy or the like. In addition, the ability of positioning a needle to the same target tissue 14 from different directions can be effective in performing simultaneous percutaneous incisions with multiple needles.

In the present embodiment, therefore, even if it is found that the target tissue 14 is out of the coverage of the needle placement manipulator 161 after the needle placement manipulator 161 is placed on the body of the patient, the combined use of the attachment 162 and the apparatus main body 1 allows the coverage to be corrected without removing the RF coil by sliding or rotating the movable portion 164 of the attachment 162. In other words, the posture of the needle placement manipulator 161 can be changed so that the target tissue 14 falls within the coverage. Changing the posture of the needle placement manipulator 161 using the attachment 162 described in the present embodiment eliminates the need to remove the RF coil from the surface of the body of the patient when change in coverage is needed. This prevents degradation of the quality of the MRI image due to movement of the RF coil and eliminates the need to position the RF coil again, leading to shorter operation time. The present embodiment enables not only to correct the coverage using the attachment 162 so that the target tissue 14 falls within the coverage but also to change the posture using the attachment 162 to prevent, for example, the interference between the bore and the apparatus main body 1.

The present embodiment allows the position and posture of the apparatus main body 1 to be determined without interference with the RF coil without adding significant design changes to the apparatus main body 1 by preparing attachments matching the apparatus main body 1 and various RF coils to set the remote center of motion (RCM) to an intended position.

Although the present embodiment has been described as related to a needle placement manipulator whose apparatus main body has a remote center of motion (RCM) mechanism, it is to be understood that the apparatus main body has only to include a guide for positioning the insertion axis of the needle and that the apparatus main body may have any configuration.

It should also be understood that the workflow for determining whether the target tissue is within the coverage of the apparatus main body is given for mere illustration and that application of the present disclosure is not limited thereto.

Although the present embodiment has been described using an MRI as a modality for visualization, the present disclosure is not limited thereto. For example, the present discloser may easily be applied to the configuration of a computed tomography (CT) scanner.

In the present embodiment, the position and posture of the apparatus main body 1 can be changed while the remote center of motion (RCM) 11 of the apparatus main body 1 is kept on the skin 15 or keeps the distance from the skin 15 constant. However, the present disclosure is not limited to the configuration. It is also easy to configure so that the remote center of motion (RCM) 11 of the apparatus main body 1 does not come to the straight line connecting the center of the internal thread 164a and the center of the slider 164c, which is also within the scope of the present disclosure.

Seventh Embodiment

Referring to FIGS. 35A to 40B, a seventh embodiment of the present disclosure will be described. The same components as those of the above-described embodiment are given the same reference signs, and detailed descriptions thereof will be omitted. In the present embodiment, a nuclear magnetic resonance imaging diagnostic apparatus (MRI) is used to visualize the inside of the body, medical devices, medical-device guide devices, etc.

In the present embodiment, an example in which a phased array coil 145 is used as an RF coil in order to obtain a clearer image in using MRI, as in the fourth and sixth embodiments, will be described. FIG. 35A is a schematic perspective view of a needle placement manipulator 171 disposed in an opening 145c of the phased array coil 145. In the present embodiment, an attachment 172 is combined with the apparatus main body 1 to constitute the needle placement manipulator 171.

Referring to FIGS. 35A to 37B, the details of the attachment 172 will be described. FIGS. 36A and 36B are schematic perspective views of the attachment 172, and FIG. 36C is a schematic perspective view of the attachment 172 as viewed from the back. The attachment 172 includes a fixed portion 173 and a movable portion 174. The fixed portion 173 has a polygonal opening and a protruding portion 173a perpendicular to a mount surface 173e. The attachment 172 can be positioned and fixed to the phased array coil 145 by fitting the protruding portion 173a to the edge 145d of an opening 145a of the phased array coil 145. An adhesive binding material (e.g., tape) may be provided on the mount surface 173e so that the mount surface 173e can be temporality bonded to the surface 145e of the phased array coil 145. The movable portion 174 has an axial opening 174a (cylindrical opening) and a ridge key 174b. The groove 2b provided on the bottom of the base body 2 of the apparatus main body 1 is fitted to the ridge key 174b, and the hole-like (cylindrical) fitting portion 2a provided in the apparatus main body 1 is fit to an axial fitting portion 174a provided in the attachment 172, so that the position and posture of the apparatus main body 1 relative to the attachment 172 can be fixed.

Figure 36A:
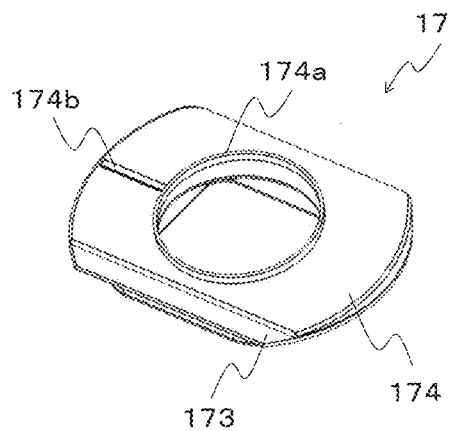
FIGS. 36A, 36B, and 36C are schematic perspective views of the attachment, according to a seventh embodiment.
Figure 36B:
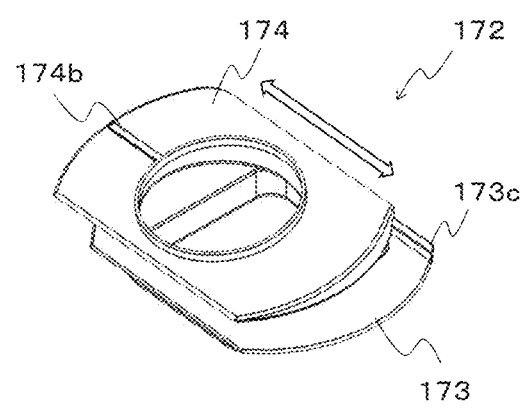
Figure 36C:
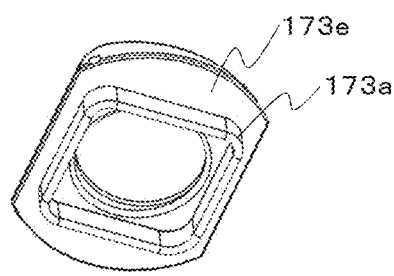
Figure 37A:
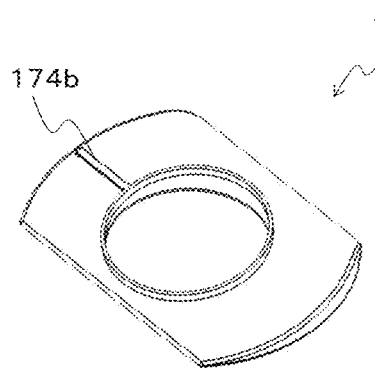
FIGS. 37A and 37B are schematic perspective views of a movable portion of the seventh embodiment.
Figure 37B:
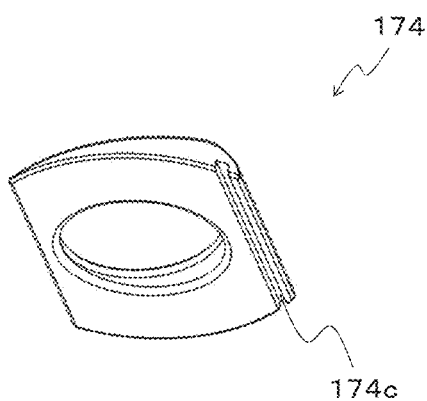

FIGS. 37A and 37B are schematic perspective views of the movable portion 174, and FIG. 38 is a schematic perspective view of the fixed portion 173. As illustrated in FIG. 37B and FIG. 38, linear guides 174c and 173c are respectively provided on the back of the movable portion 174 and on the upper surface of the fixed portion 173. The movable portion 174 can be linearly moved along the linear guide 173c, as illustrated in FIG. 36B. In the needle placement manipulator 171, the attachment 172 is configured such that, when the movable portion 174 is moved along the linear guide 173c, the remote center of motion (RCM) 11 of the apparatus main body 1 is kept on the skin 15 or keeps the distance from the skin 15 constant. The movable portion 174 may be moved manually or using an automated actuator. A fixing unit for fixing (locking) the position of the movable portion 174 with respect to the fixed portion 173 may be provided as appropriate. Applicable examples of a fixing unit include the above-described thread with a knurled knob, and the layered piezoelectric element with a compression coil spring, described in the first embodiment. However, locking can be implemented various other ways, including a sliding key, turn lock, or set screw.

FIGS. 39A and 39B illustrate simulated puncture to the target tissue 14 using the needle placement manipulator 171 disposed on a patient's skin 15. FIGS. 40A and 40B are schematic plan views of the needle placement manipulator 171 disposed on the phased array coil 145 viewed from directly above. FIG. 40B illustrates a state in which the movable portion 174 is slid linearly upward in the plane of the drawing from the position in FIG. 40A. FIGS. 39A and 39B are respective schematic cross-sectional views of FIGS. 40A and 40B taken along a plane passing through the needle 12.

In using the MRI for visualization, the phased array coil 145 is first positioned and fixed on the patient's skin 15 with tape or band to acquire a sharp image of the target site. After completion of the fixation of the phased array coil 145, the apparatus main body 1 is fixed on the body of the patient using the attachment 172. In FIG. 39A, the target tissue 14 is not within coverage, so that the tip of needle 12 cannot be brought to the target tissue 14 even if the first and second rotation guides 3 and 4 are rotated. In that case, for the apparatus main body 1 and the attachment 172, the movable portion 174 is linearly slid in an upward direction, as illustrated in FIG. 40B. Then, planning for bringing the needle 12 to the target tissue 14 is performed on the basis of the posture of the apparatus main body 1 detected using the markers 16, and when it is determined that the target tissue 14 is within the coverage, the first and second rotation guides 3 and 4 are displaced to predetermined positions to position the needle 12 toward the target tissue 14.

In the present embodiment, the target tissue 14 can be brought within the coverage by changing the position of the apparatus main body 1 along the linear guides 173c and 174c using the attachment 172, allowing the needle 12 to be brought to the target tissue 14, as illustrated in FIG. 39B. Even if the target tissue 14 is within the coverage of the needle placement manipulator 171 in the state of FIG. 39A, the configuration of the present embodiment allows planning for the target tissue 14 excluding human tissue, such as bones, which should not be hurt by the needle 12, if included in the puncture path. In addition, positioning the needle 12 to the same target tissue 14 from different directions is also effective in multiple-needle puncture therapy for expanding a frozen region (ice ball) at the leading end of the needle 12 in freezing therapy or the like.

In the present embodiment, even if it is found that the target tissue 14 is out of the coverage of the needle placement manipulator 171 after the needle placement manipulator 171 is placed on the body of the patient, the combined use of the attachment 172 and the apparatus main body 1 allows the coverage to be corrected without removing the RF coil by sliding the movable portion 174 of the attachment 172 along the linear guide 173c. In other words, the posture of the needle placement manipulator 171 can be changed so that the target tissue 14 falls within the coverage. Changing the posture of the needle placement manipulator 171 using the attachment 172 described in the present embodiment eliminates the need to remove the RF coil from the surface of the body of the patient when change in coverage is needed. This prevents degradation of the quality of the MRI image due to movement of the RF coil and eliminates the need to position the RF coil again, leading to shorter operation time. The present embodiment enables not only to correct the coverage using the attachment 172 so that the target tissue 14 falls within the coverage but also to change the posture using the attachment 172 to prevent, for example, the interference between the bore and the apparatus main body 1.

The present embodiment allows the position and posture of the apparatus main body 1 to be determined without interference with the RF coil without adding significant design changes to the apparatus main body 1 by preparing attachments matching the apparatus main body 1 and various RF coils to set the remote center of motion (RCM) to an intended position.

Although the present embodiment has been described as related to a needle placement manipulator whose apparatus main body has a remote center of motion (RCM) mechanism, it is to be understood that the apparatus main body has only to include a guide for positioning the insertion axis of the needle and that the apparatus main body may have any configuration.

It should also be understood that the workflow for determining whether the target tissue is within the coverage of the apparatus main body is given for mere illustration and that application of the present disclosure is not limited thereto.

Although the present embodiment has been described using an MRI as a modality for visualization, the present disclosure is not limited thereto. For example, the present discloser may easily be applied to the configuration of a computed tomography (CT) scanner.

In the present embodiment, the position and posture of the apparatus main body 1 can be changed while the remote center of motion (RCM) 11 of the apparatus main body 1 is kept on the skin 15 or keeps the distance from the skin 15 constant. However, the present disclosure is not limited to the configuration.

Eighth Embodiment

Instead of having a separate fixed portion and movable portion, the attachment can be implemented as a statically inclined adapter having a predetermined inclination. FIGS. 41A to 46 illustrate an eighth embodiment of the present disclosure. The same components as those of the above-described embodiment are given the same reference signs, and detailed descriptions thereof will be omitted. In the present embodiment, a nuclear magnetic resonance imaging (MRI) modality is used to visualize the inside of a patient's body, medical devices, medical-device guide devices, etc. The type of attachment implemented as a statically inclined adapter having a predetermined inclination can be used in scenarios where a specific angulation is often needed. For example, to reach a shallow target tissue which is obstructed from above, to prevent the manipulator from colliding with other medical equipment placed near the manipulator, or to revert the orientation of the manipulator to a perpendicular position if it cannot be mounted directly onto the patient in such position. This statically inclined adapter can be designed in a way where one or more statically inclined adapters can be stacked to achieve additional angulations. For example, the user can place an attachment having a predefined 30 degree inclination, and then, if necessary, place a +5 degrees or −5 degree wedge on top to get to a 25 or 35 degree inclination if the original 30 degrees is not sufficient to reach a target.

A statically inclined adapter can be rotated from its original position to adjust the location of the remote center of motion without changing the device footprint. Specifically, in the previously described embodiments, changing the orientation of the apparatus main body 1 with respect to the target tissue 14 is achieved by using one or more guides to slide the movable portion with respect to the fixed portion. This mechanical movement changes the overall needle manipulator's footprint. In contrast, by using an attachment having statically inclined surface, the devices' footprint does not change. The rotation can be achieved by rotating the entire assembly; that is, by rotating the attachment and the manipulator together, or by having the statically inclined adapter rotate within the base body 2 of the apparatus main body 1, either manually or electronically.

Figure 41A:
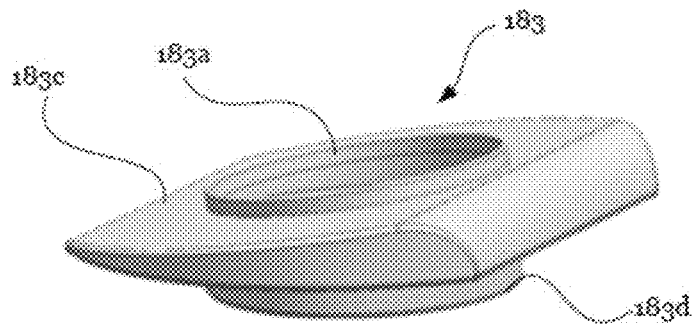
FIGS. 41A, 41B and 41C respectively illustrate perspective, top, and bottom views of a first example an attachment designed as a statically inclined adapter according to a seventh embodiment.
Figure 41B:
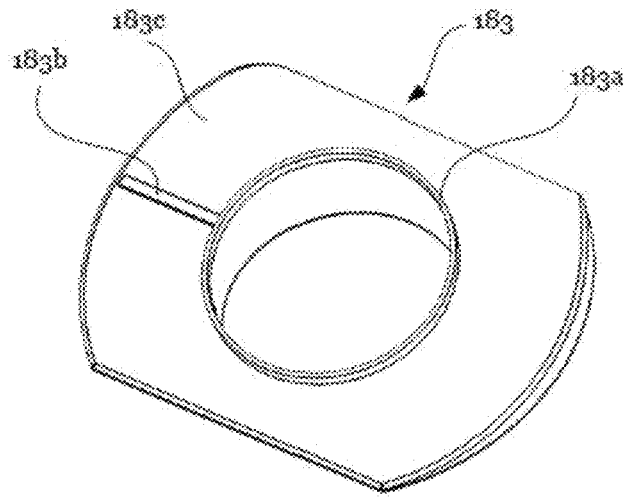
Figure 41C:
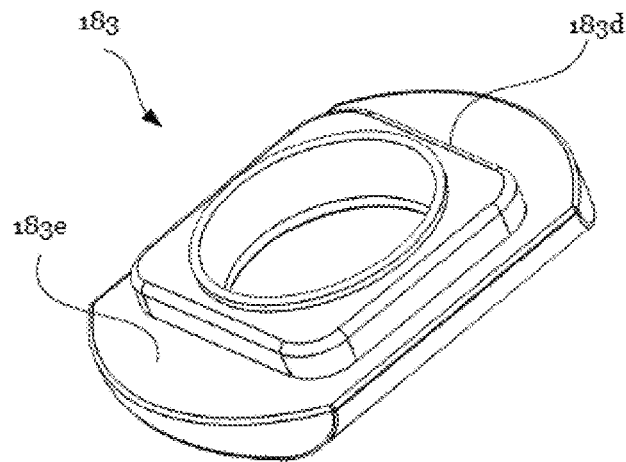

FIGS. 41A, 41B and 41C show a first example of an attachment 183 designed as a statically inclined adapter. FIGS. 42A-42E show a second example of an attachment 283 designed as a statically inclined adapter. FIGS. 43, 44A, 44B, 44C, and 45 illustrate functionality and exemplary applications of the attachments 183/283 designed as a wedge-shaped adapter for use in a needle placement manipulator. FIG. 41A is a perspective view and FIG. 41B is a top view of the attachment 183 showing a cylindrical opening 183a, a ridge key 183b, and an inclined surface 183c. FIG. 41C is a bottom view of the attachment 183 showing a protruding portion 183d and a mount surface 183e. The protruding portion 183d on the bottom of attachment 183 is configured so that the attachment 183 can be positioned and fixed to the phased array coil 145 (see FIG. 19) by fitting the protruding portion 183d to the edge 145d of an opening 145c of the phased array coil 145. An adhesive material may be provided on the mount surface 183e so that the mount surface 183e can be temporarily bonded to the surface 145e of the phased array coil 145. According to this embodiment, the inclined surface 183c of the attachment 183 is inclined with respect to the attachment surface 183e by a predetermined angle δ.

Figure 42A:
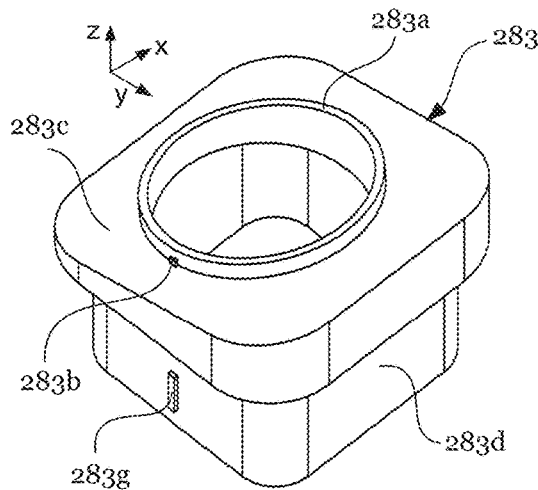
FIGS. 42A, 42B and 42C respectively illustrate perspective, top, and bottom views.
Figure 42B:
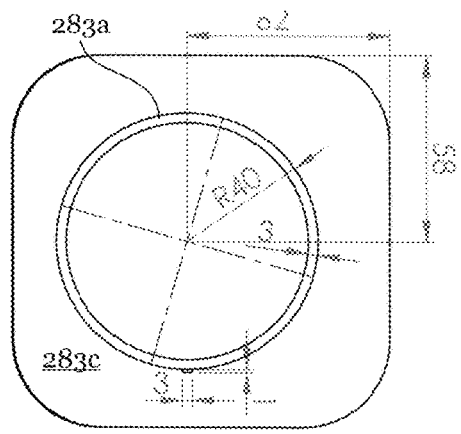
Figure 42C:
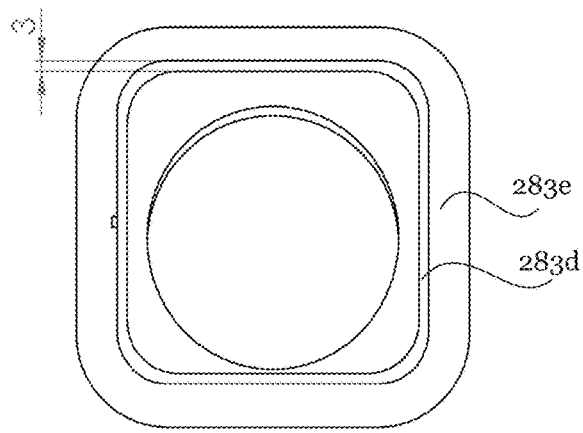

FIG. 42A is a perspective view and FIG. 42B is a top view of an attachment 283. FIG. 42A shows the attachment 283 includes an upper protruding portion having a cylindrical opening 283a, a wedge-shaped section having an inclined surface 283c, and a polygonal protruding portion 283d. FIG. 42C shows a bottom view of the attachment 283 showing the polygonal protruding portion 283d and a mount surface 283e. The polygonal protruding portion 283d on the bottom of attachment 283 is configured so that the attachment 283 can be positioned and fixed to the phased array coil 145 (see FIG. 19) by fitting the protruding portion 283d to the edge 145d of an opening 145c of the phased array coil 145. To secure the attachment 283 to the opening 145c, an adhesive material may be provided on the mount surface 283e so that the mount surface 283e can be temporarily bonded to the surface 145e of the phased array coil 145. Additionally, the polygonal protruding portion 283d is provided with a ridge key 283g to ensure the adapter is assembled in the correct orientation. Similarly, the upper protruding portion having a cylindrical opening 283a is configured so that the attachment 283 can be locked onto the base body 2 of the apparatus main body 1. To that end, the cylindrical opening 283a is provided with a pressurized protruding pin 283b. In this manner, the apparatus main body 1 of the needle placement manipulator is vertically locked with a removable pin/pinhole combination, so that the needle placement manipulator sits atop the inclined surface 283c and is aligned and rotationally locked with a key/keyway combination. It is understood that this alignment and locking can be implemented in various other ways, including a sliding key, turn lock, or set screw.

Figure 42D:
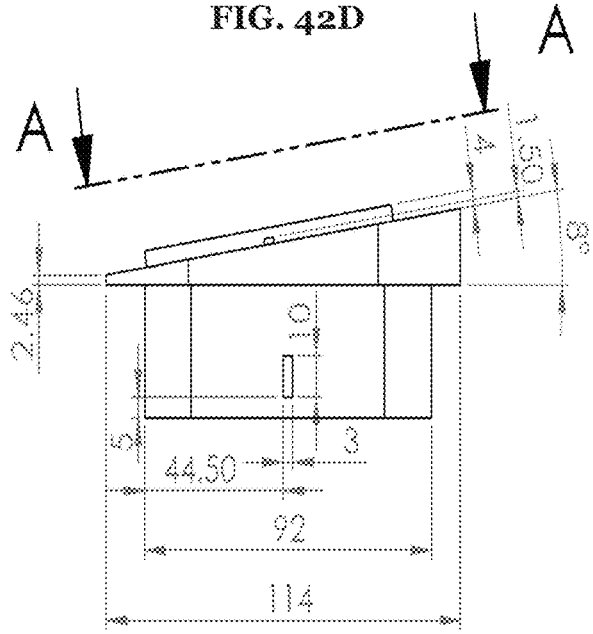
FIGS. 42D and 42E illustrate side views of a second example of an attachment designed as a statically inclined adapter according to the seventh embodiment.
Figure 42E:
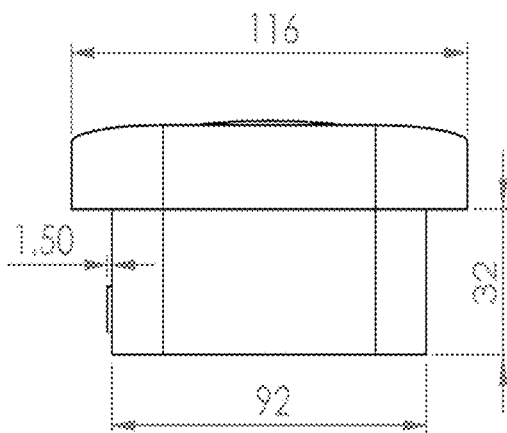

According to FIG. 42A, the inclined surface 283c of the attachment 283 is inclined with respect to the mount surface 283e by a predetermined angle δ. FIG. 42D shows an example where the inclined surface 283c is inclined with respect to the mount surface 283c by a predetermined angle δ of 8 degrees. However, if the predetermined angle δ is not adequate for a desired purpose, the predetermined angle δ can be adjusted, as mentioned above, by adding one or more wedges of, for example, +5 degrees or −5 degrees, on top of the attachment 183 to get to a desired degree of inclination. In this manner, as illustrated in FIG. 44C, the distance between the inclined surface 183c and the remote center of motion (RCM) 11 of the apparatus main body 1 can be adjusted to a predetermined distance from the patient's surface, such that the remote center of motion (RCM) 11 of the apparatus main body 1 can be located at or above the skin 15.

Figure 43:
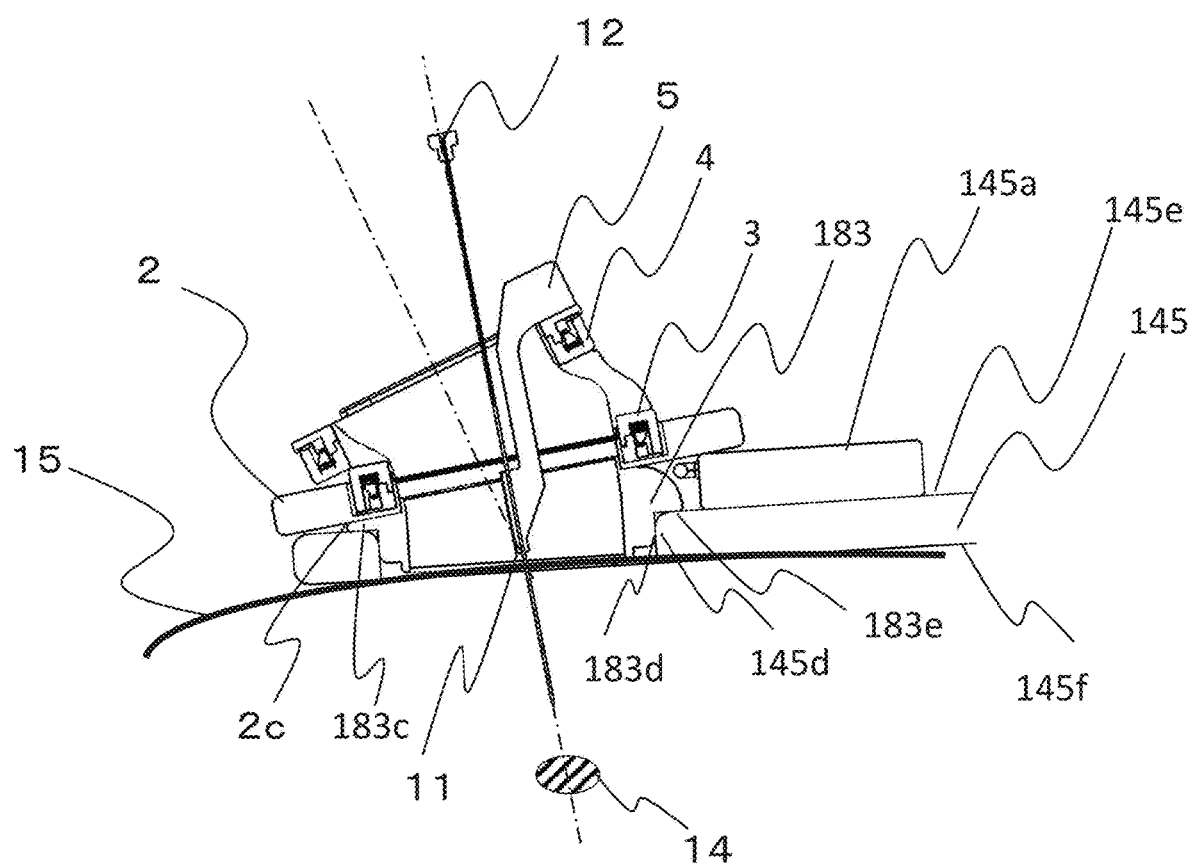
FIG. 43 illustrates exemplary functionality and application of the statically inclined adapter during a percutaneous puncture operation according to the seventh embodiment.

FIG. 43 illustrates an exemplary function of the attachment 183 during a percutaneous puncture operation to reach a target tissue 14 using a needle placement manipulator disposed on a patient's skin 15. As shown in FIG. 3, by changing the posture of the needle placement manipulator using the attachment 183 of the present embodiment, the coverage of the needle placement manipulator can be adjusted so that the needle 12 can be brought to the target tissue 14.

Specifically, in the case shown in FIG. 43, a doctor first decides the position of the phased array coil 145 suitable to capture an image of a region of interest, and secures the phased array coil 145 on the skin 15 of the patient by using, for example, a tape, a belt, or a band. Subsequently, the attachment 183 is placed on a surface 145e of the phased array coil 145 such that the mount surface 183e of the attachment 183 is in contact with the surface 145e of the phased array coil 145. At this time, the protruding portion 183d protruding from the mount surface 183e is fitted within the edge 145d of the coil opening 145c to adjust the position of the attachment 183 relative to the phased array coil 145. An adhesive material is preferably disposed on the mount surface 183e to temporarily fix the attachment 183 to the surface 145e. Subsequently, the doctor places the apparatus main body 1 on the inclined surface 183c of the attachment 183. The inclined surface 183c is inclined at an angle such that the signal processing members 145a (pre-amplifiers) of the phased array coil 145 are below the inclined surface 183c when the attachment 183 is attached to the phased array coil 145. This enables the doctor to place the apparatus main body 1 above the phased array coil 145 without the signal processing members 145a (pre-amplifiers) interfering with the apparatus main body 1. The angle of the inclined surface 183c is in a range of about 5 degrees to about 30 degrees from the perspective of stability of the apparatus main body 1 during placement. That is, the angle of the inclined surface can be tailored such that the center of gravity (or center of mass) of the apparatus main body 1 is substantially at equilibrium.

The position and posture of the apparatus main body 1 relative to the attachment 183 are maintained in a manner in which a ridge key 183b (protrusion) formed on the inclined surface 183c is fitted into a groove 2b formed in the bottom surface of the apparatus main body 1, and the protruding portion 183a formed on the attachment 183 is fitted into a cylindrical fitting portion 2a (hole) formed in the base body 2 of apparatus main body 1. The relationship between the groove 2b and the ridge key 183b may be interchanged. After the apparatus main body 1 has been secured, the first and second rotation guides 3 and 4 can be rotated such that the insertion axis 5a of the needle holder 5 is directed to the target tissue 14. Subsequently, a doctor performs a puncture at a depth required to reach the target tissue 14 by moving the needle 12 along the insertion axis 5a. In the event that the first and second rotation guides are rotated, but the insertion axis 5a of the needle holder 5 still does not reach the target portion 14, the operator (doctor) can use one or more additional wedged adapters until the angle necessary for the needle 12 to reach the target tissue is achieved.

According to the present embodiment, the inclined surface 183c of the attachment 183 is inclined at a predetermined angle δ with respect to the mount surface 183e, and the distance between the inclined surface 183c and the remote center of motion (RCM) 11 can be adjusted to a desired distance such that the remote center of motion (RCM) 11 of the apparatus main body 1 can be located at or above the skin 15. Specifically, in consideration of the deformation the contour shape of the patient's body or due to the rise of the apparatus main body 1 when the phased array coil 145 is rigidly attached to the patient's skin, the remote center of motion (RCM) 11 can be adjusted to be located at about zero (o) to 10 mm above the bottom surface 145f of the phased array coil 145. To that end, the attachment 183 having an inclined surface 183c can be arranged by using additional adaptive wedges having a thickness and inclination necessary to achieve the desired height and inclination.

Figure 44A:
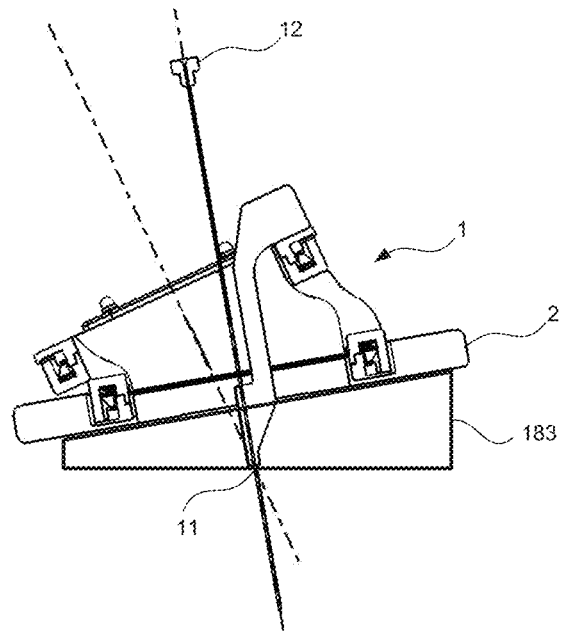
FIGS. 44A and 44B illustrate further exemplary functionality and applications of the attachment designed as a statically inclined adapter during a percutaneous puncture operations according to the seventh embodiment.
Figure 44B:
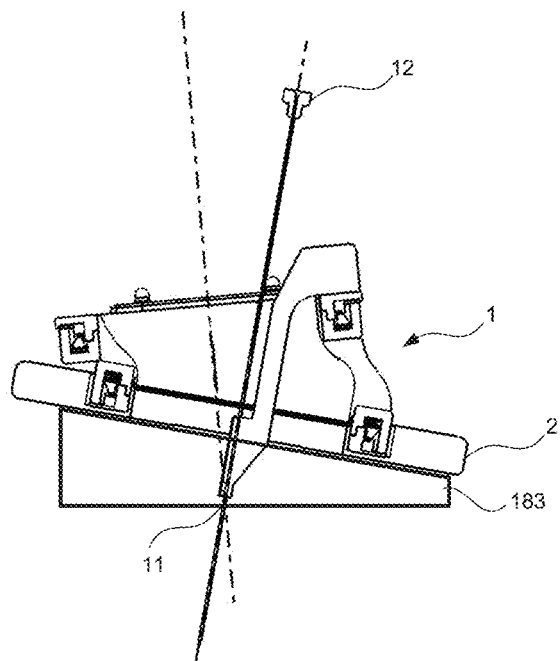
Figure 44C:
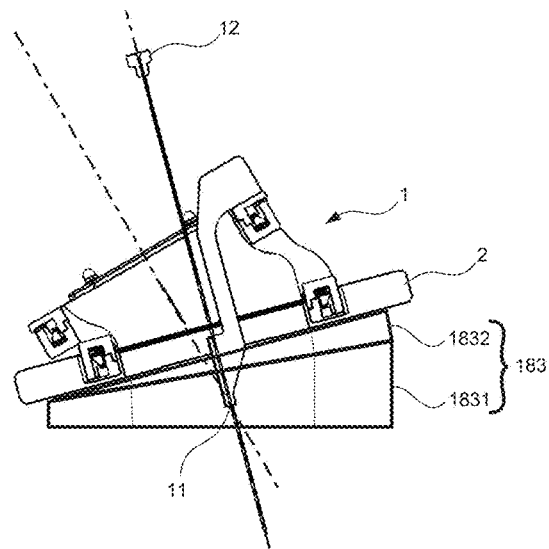
FIG. 44C illustrates an example an attachment designed as a statically inclined adapter for a needle placement manipulator where the attachment includes multiple wedge-shaped adapters stacked onto each other.

FIGS. 44A and 44B show a possible application of attachment 183 designed as a single piece wedge-shaped adapter. As shown in FIGS. 44A and 44B, an attachment 183 designed as a statically inclined adapter can be rotated from its original position to adjust the location of the remote center of motion 11 without changing the device footprint of the device. This rotation can be achieved by rotating the entire assembly, or by having the statically inclined adapter rotate within a base, either manually or electronically. An example of this application is shown in FIG. 44 where the apparatus main body 1 of the needle placement manipulator has been mounted onto an attachment 183 having a first wedge-shaped adapter 1831 and a second wedge-shaped adapter 1832. In FIG. 44, as compared to FIG. 43B, the use of multiple wedge-shaped adapters causes the remote center of motion 11 to be placed higher (more distant) with respect to the subject's body.

Advantageously, being that the attachment 183 is a single piece element, it can be manufactured with high precision and at a low cost, for example, by injection molding with a resin material or other materials compatible with the imaging modality to be used. The low-cost manufacture enables the attachment 183 to be a disposable component. A sterilization process and seal packaging after manufacture enables the attachment 183 to be maintained in a sterile state until the eventual use, thereby providing an improvement in safety for the patient.

Whether the target tissue 14 is within the coverage of the apparatus main body 1, when using the attachment 183, is determined using a similar procedure as that described in the previous embodiments. Initially, it is understood that the posture of the attachment 183 is determined and fixed by the operator (a doctor or imaging technician) in the process of attaching the needle placement manipulator onto the patient. Subsequently, whether the coverage of the apparatus main body 1 includes the target tissue 14 is determined through, for example, calculation based on images of fiducial markers 16 provided on the apparatus main body 1. Images of the markers 16 can be obtained by an X-ray CT scanner or an MRI imaging modality, as applicable. If it is determined that the target tissue 14 is within the conical coverage of the needle placement manipulator, planning for bringing the needle 12 to the target tissue 14 is executed to displace the first and second rotation guides 3 and 4 to predetermined angles, thereby directing the needle 12 in the direction of the target tissue 14. On the other hand, if it is determined that the target tissue 14 is not yet within the desired coverage, the coverage of the needle placement manipulator can be adjusted by placing one or more additional inclined adapters (wedges) above the attachment 183.

The basis for expanding the coverage of the needle placement manipulator using the attachment 183 of the present embodiment is similar to that shown and described with reference to FIGS. 10A to 10C. FIG. 10A illustrates the initial coverage of the needle placement manipulator without the use of the attachment 183. FIG. 10B illustrates a state in which the posture of the apparatus main body 1 is inclined (adjusted) by an angle δ using the inclined surface 183c of attachment 83. In this state shown in FIG. 10B, the entire conical coverage 108 is inclined by the angle δ, as compared to the position shown in FIG. 10A. If the attachment 183 is extracted from the opening 145c of the phased coil array 145 and rotated, the conical coverage 108 can be adjusted by an angle δ across the four sides of the opening 145c. Accordingly, the coverage of the needle placement manipulator is increased to a conical region 109 enclosed by the dashed line with an apical angle of 4θ+2δ and with the remote center of motion 11 as a vertex thereof, as illustrated in FIG. 10C.

In this embodiment, as shown in FIGS. 41A, 41B and 41C, a ridge key 183b on the inclined surface 183c of the single element attachment 183 aligns with a groove 2b (keyway) of the base body 2 to ensure the adapter is assembled in the correct orientation. In the case of using one or more additional wedge-shaped adapters, additional pairs of ridge key and groove combinations are to be used. In this manner, the needle placement manipulator sits atop the inclined surface of the wedge-shaped adapter using another ridge key/keyway pair for alignment. The inclined adapter can be designed at a fixed angle, for example of 8 degrees, to ensure the manipulator will avoid an amplifier circuit (signal processing member 145a) which sits adjacent to an edge 145d of an opening 145c on the phased coil array 145, as shown in FIG. 43.

The apparatus main body 1 and the attachments 183 suitable to various RF coils can be prepared without a major design change of the apparatus main body, so that the remote center of motion (RCM) can be located at the intended position, and the position and posture of the apparatus main body can be determined without interference with the RF coils.

According to the present embodiment, the needle positioning apparatus including the attachment can be placed on a patient after the RF coil is placed on the patient. And even if it is found out that the target tissue is not within the coverage of a needle placement manipulator after the needle placement manipulator is placed, the coverage can be corrected so that the target issue falls within the coverage by adjustment using the attachment 183. For this reason, it is possible to remove something that can interfere with the RF coil from the skin during a process of searching the position at which the RF coil is to be placed in a workflow of a puncture surgery.

According to the embodiment, an example of using the attachment 183 with a phased-array coil as the RF coil is described. In other cases, however, the attachment 183 can also be used with a single loop coil 135 (shown in FIG. 16C), which is another kind of surface RF coil that can be placed on a patient's skin 15.

As contemplated in this embodiment (see FIGS. 41A and 42A), the attachment 183 or attachment 283 can be designed as a single element wedge-shaped adapter having an inclined surface with a predetermined angle of inclination. This design can be extremely useful and advantageous due to the lack of moving parts, and more importantly it can be made disposable. However, due to the flexibility of the phased array coil, the single element wedge-shaped adapter may not be applicable in all situations. Therefore, ensure that the attachment 183 is properly combined with the RF coil, a base or a setting portion on which the RF coil is set may be used.

Figure 45:
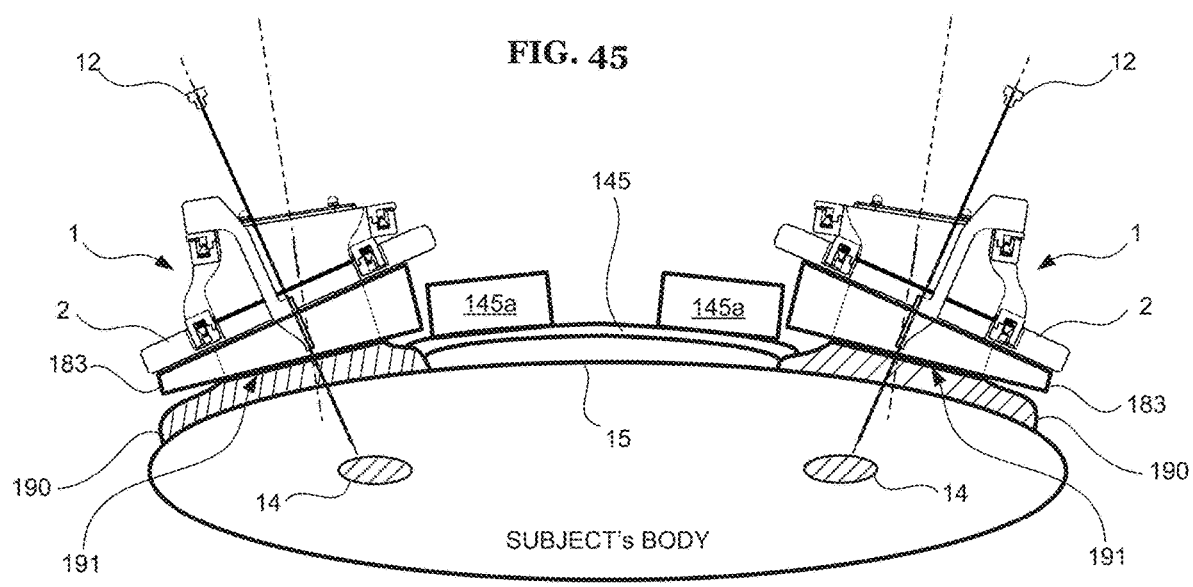
FIG. 45 illustrates an example of using a curved base to mount one ore more attachments having an inclined surface onto a subject's body such that a needle placement manipulator will avoid interference with parts of a phased array RF-coil.
Figure 46A:
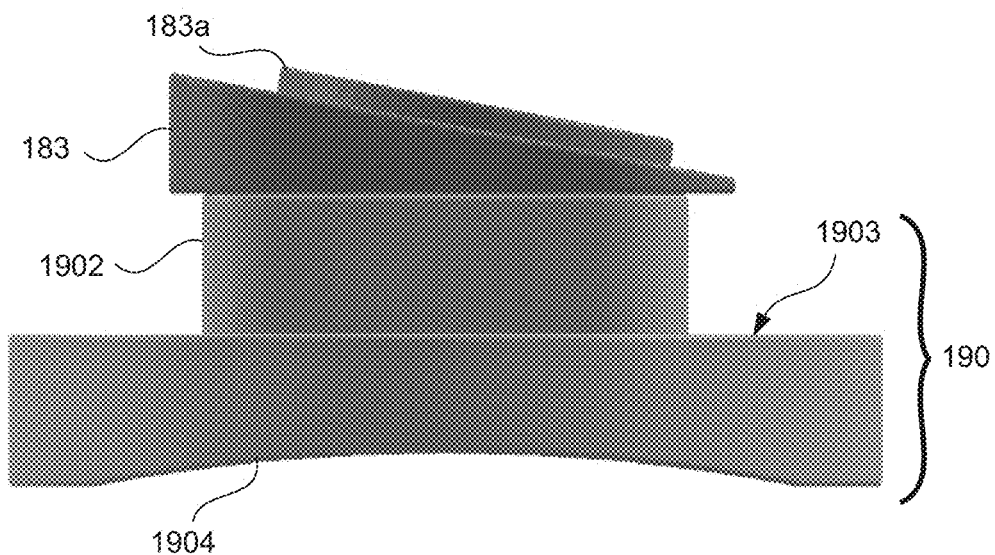
FIGS. 46A and 46B show side view arrangements of a base having a curved mounting surface configured to fit the contour shape of a patient's body.

FIG. 45 illustrates an example of attachment 183 mounted onto a subject's body with a phased array coil 145 therebetween. As shown in FIG. 45, the phased array coil 145 wraps around the skin 15 of the subject's body. When a region of interest, e.g., target tissue 14, is located below a surface where the attachment 183 does not sit flush in its intended position, a base 190 can be designed for mounting the coil 145 onto the subject's body, and a mounting surface of the base (the surface in direct contact with the subject's body) can be also designed according to the contour shape of the subject's body. FIG. 46 shows a side view arrangement of the base 190 and the attachment 183. As shown in FIG. 46, the base 190 includes an upper protruding portion 1902, a setting potion 1903 on which the RF-coil is set, and a curved mounting surface 1904 configured to fit the contour shape of a patient's body.

In this embodiment, the base 190 configured to be placed on the patient's torso may be designed containing registration fiducials 16. The phased array RF-coil 145 is then placed over the base 190 by aligning one of the openings 145c with the upward protruding portion 1902 of the base 190. To facilitate a better fit of the attachment 183 onto the base 190, the upward protruding portion can be designed with an inclined surface 191. The attachment 183 having one or more wedge-shaped adapters (1831, 1832) is then placed atop this upward protrusion 1902, securing the RF-coil 145 in place between the base 190 and the wedge-shaped adapter. A key on the attachment can be used to align with a keyway along the protrusion 1902 to ensure the adapter is assembled in the correct orientation with respect to the subject's body. The apparatus main body 1 of manipulator then sits atop the inclined surface 183c of attachment 183 using another key/keyway for alignment. This inclined adapter is at a fixed angle to ensure the manipulator will avoid an amplifier enclosure (processing unit 145a) which sits adjacent to the opening on the coil.

In one experiment conducted by the inventors herein, a wedge-shaped adapter having an angle of 8 degrees was selected for a number of reasons. First, it is the minimum angle necessary to avoid collision with the amplifier enclosure. Second, it is necessary to minimize the loss of accessible area of the manipulator. Specifically, since the manipulator is angled, the base begins to encroach upon the conical range of accessible area of the manipulator, the angle of the wedged adapter is necessary to minimize the loss of accessible area. Lastly, it is preferable that the RCM of the manipulator be as close to the original location as possible. Due to the fact that the adapter has to sit atop the fixed protrusion of the base, the angulation cannot rotate about the RCM of the manipulator. Therefore, RCM is raised away from the non-angled position as the angulation increases. This is undesired as it decreases the depth that the manipulator can reach and increases the size of the potential needle insertion area upon the skin surface.

For example, as shown in FIG. 19, the amplifier boxes (signal processing units 145*a*) lay medially from the openings 145*c*, therefore there are only two different ways the assembly can sit within the phased array coil 145. Knowing that the phased array coil 145 typically wraps around the patient torso along the transverse direction of the patient, the base 190 can be designed with a curved bottom surface (mounting surface 1904) to align with the curved shape of the torso for a better fit. The radius of this curve can vary so different bases can be used for different body shapes and sizes.

Figure 46B:
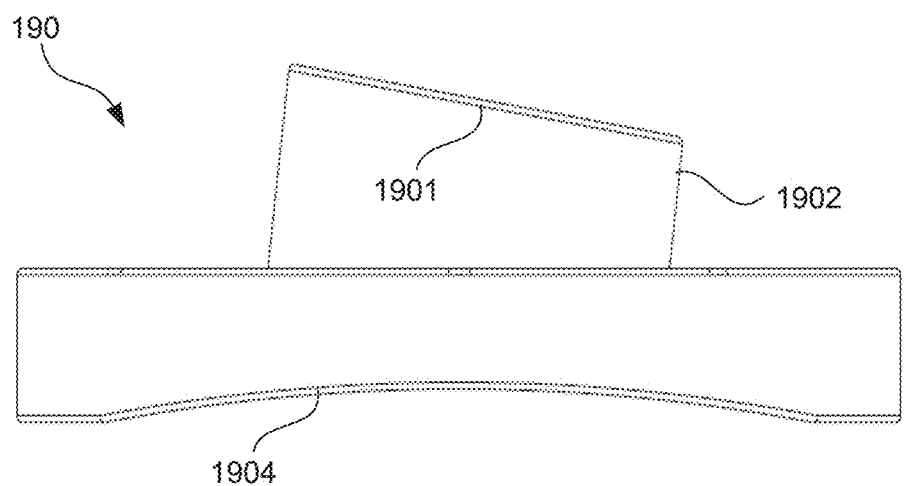

FIG. 46B illustrates a base 190 having a curved mounting surface 1904 adapted to fit the contour shape of a patient. In FIG. 46B, the base 190 is designed with a protrusion 192 where angulation can integrated into the protrusion, and an inclined surface 1901 replaces the attachment 183 thereby removing the need of an additional wedge-shaped adapter to sit atop the base. That is, the attachment 183 having an inclined surface 183*c* can be combined with the base 190 into a single piece, as shown in FIG. 46B. This can be done by angling the upward protrusion 1902 by the desired angle (e.g., 8 degrees as mentioned above). The needle placement manipulator then sits atop this base with an angled protrusion, and is aligned and rotationally locked with a key/keyway combination, and vertically locked with a removable pin/pinhole combination, as explained above.

One benefit of this design is the removal of the base encroaching upon the reachable area of the manipulator. Since the protrusion will run perpendicular to the bottom surface of the manipulator, the reachable area will be untouched by the base as long as the height of the protrusion is within the desired range. An additional benefit of this design is the fact that the angle of the manipulator can be adjusted without changing the position of the remote center of motion. Since this angulation is integrated into the base, the rotation can occur about the remote center of motion, and the height of the remote center of motion can be controlled by controlling the height of the protrusion. In this embodiment, a base containing registration fiducials can be placed on the patient's torso.

Ninth Embodiment

Figure 47A:
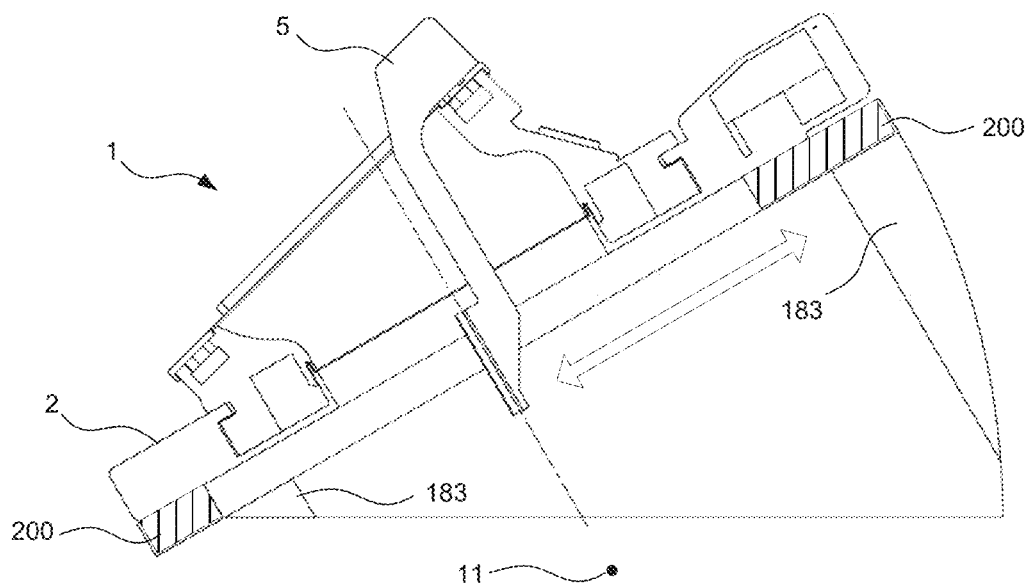
FIGS. 47A, 47B, and 47C show perspective and cross-sectional views of an embodiment of an attachment mounted onto one or more linear guides which are configured as fixed distance translational adapters.
Figure 47B:
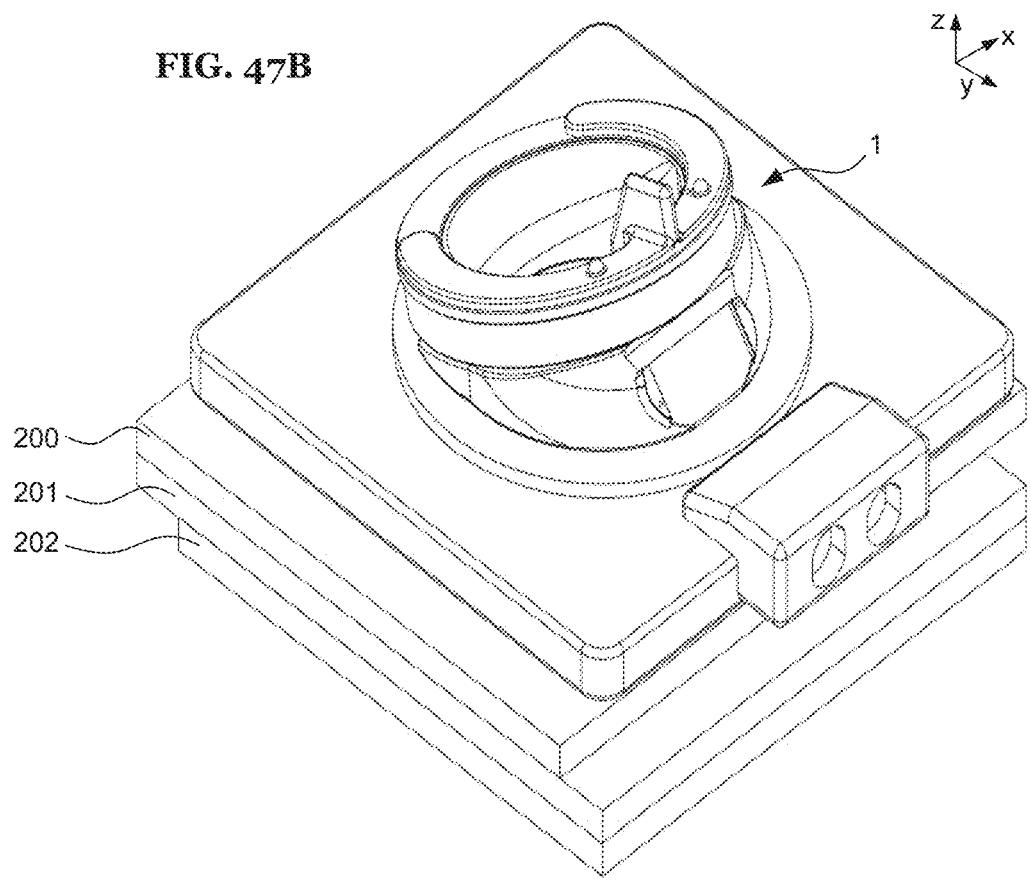
Figure 47C:
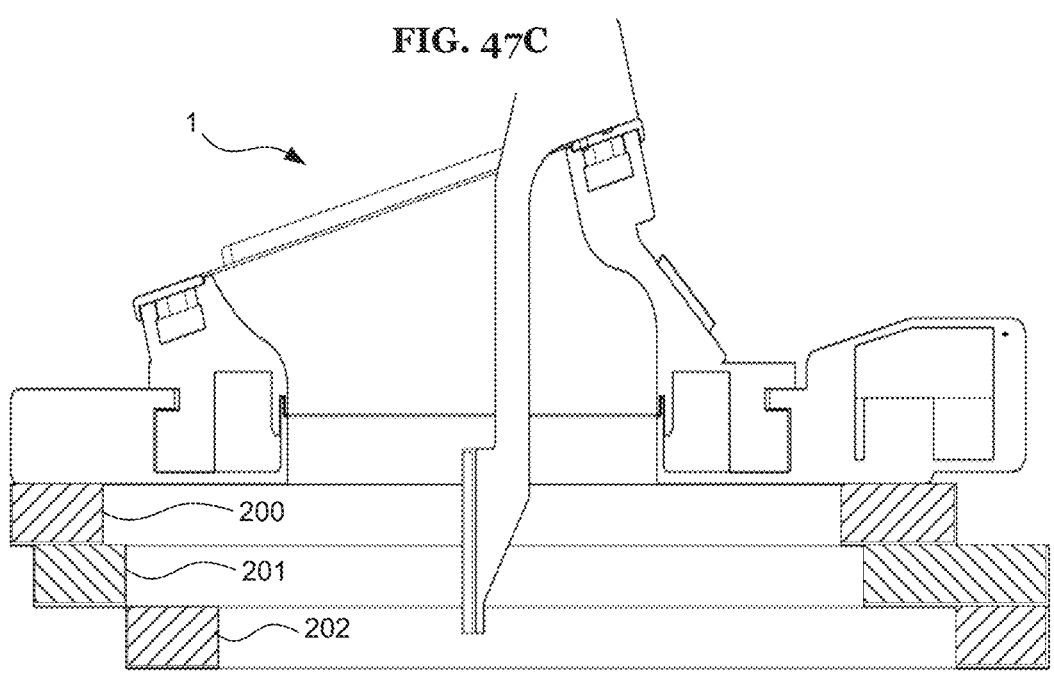

FIGS. 47A, 47B, and 47C show an embodiment of an attachment 183 mounted on one or more linear guides 200, 201, and 202. As shown in FIG. 47A, the attachment 183 having an inclined surface of a predetermined angle can be combined with a fixed distance translation adapter (a linear guide), which can be used to move the apparatus main body 1 of needle placement manipulator a specific distance away from its original position. For example, after placing the needle placement manipulator on the patient and performing medical imaging, the clinician may determine that the device needs to be shifted a predetermined distance (e.g., 20 mm) to be able to reach the target tissue 14. Therefore, a fixed distance translation adapter can be placed between the apparatus main body 1 and the attachment to shift the device by the specific amount (e.g. a distance of 20 mm). If a different displacement is needed, additional translation adapters may be stacked to create a specific distance. For example, a 5 mm or −5 mm displacement adapter can be used in addition to the 20 mm adapter to create a 25 mm or 15 mm displacement. In this manner, a fixed translation adapter can be used in conjunction with a fixed angled adapter to move the RCM to another location along the inclined plane of the inclined surface. For example, a fixed translation adapter designed specifically for a 30 degree angled adapter can be used to move the device in such a manner than the zero/initial trajectory lines up with the position of the RCM before the angled adapter was placed. FIG. 47B shows a perspective view and FIG. 47C shows a cross sectional view of an apparatus main body 1 mounted onto a plurality of linear guides 200, 201 and 202 which can be used to linearly move the needle placement manipulator along the inclined surface 183*c* of the attachment 183 in one or more directions. For example, as shown in FIG. 47B, a first linear guide 200 can move the apparatus maim body 1 a fixed distance in the x-direction, and a second liner guide 201 can move the apparatus maim body 1 a fixed distance in the y-direction, while a third linear guide 202 is fixed onto the inclined surface 183*c* of the attachment 183. Accordingly, with the use of one or more linear guides combined with the inclined surface of the wedge-shaped adapter, as described in the present embodiment, it is not only possible to adjust the conical region of coverage, but it is also possible to move the conical region of coverage so that a target tissue outside of the conical region of coverage can be reached by the needle of the needle placement manipulator.

As a result, even if it is found that the target tissue is outside of the coverage of a needle placement manipulator after the needle placement manipulator is placed on a patient's body, the coverage can be corrected by adjustment using the attachment and one or more linear guides so that the target issue falls within the coverage.

As it will be appreciated by those skilled in the art, if the inclined surface 183*c* is visible in the medical images acquired by the imaging modality, the posture of the needle guide device can be known in advance, before the needle placement manipulator is even mounted on the patient. Note that without this type of inclined surface, the posture of the needle guide device is unknown when it is mounted because the patient skin has curved shape and can deform. Therefore, the use of an attachment having an inclined surface can reflect that posture information to the plan before the device is actually mounted.

In addition, when the base 190 is designed according to the contour shape of the subject's body, the base 190 can be made by 3D printing or any other rapid prototyping technique based on the actual individual patient contour shape data from the medial image. Accordingly, with those pre-designed patient contour, it can become much easier reflect/design the posture and even the position of the needle guide device before even planning the trajectory of the percutaneous puncture. Therefore, the use of an attachment having a predefined inclined surface in particular when fiducial markers are included in the base of the attachment is considered a unique advantage of the present disclosure.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions. To that end, it should be understood that the singular forms "a", "an", and "the" are intended to include the plural forms as well, unless the context clearly indicates otherwise. It should be further understood that the terms "includes" and/or "including", "comprises" and/or "comprising" when used in the present specification and claims, specify the presence of stated features, integers, steps, operations, elements, and/or components, but do not preclude the presence or addition of one or more other features, integers, steps, operations, elements, components, and/or groups thereof not explicitly stated. The terms "consists of" and/or "consisting of" when used in the present specification and claims, specify the presence of a closed group of stated features, integers, steps, operations, elements, and/or components, and excludes the presence or addition of one or more other features, integers, steps, operations, elements, components, and/or groups thereof not explicitly stated.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without departing from structural or functional meaning.

It should be further understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Lastly, spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

LIST OF EXEMPLARY REFERENCES

The following non-patent literature (NPL) and patent publications, which are considered "nonessential material", are hereby incorporated by reference herein in their entirety:
1. Liu S, Xia Z, Liu J, Xu J, Ren H, Lu T, et al., "Automatic Multiple-Needle Surgical Planning of Robotic-Assisted Microwave Coagulation in Large Liver Tumor Therapy", the public library of science (PLoS) ONE11(3): e0149482. Published: Mar. 16, 2016, https://doi.org/10.1371/journal.pone.0149482;
2. Ken Masamune, Etsuko Kobayashi, Yoshitaka Masutani, Makoto Suzuki, Takeyoshi Dohi, Hiroshi Iseki & Kintomo Takakura, "Development of an MRI-Compatible Needle Insertion Manipulator for Stereotactic Neurosurgery", Journal of Image Guided Surgery Vol. 1, Iss. 4, 1995;
3. Patent publications include: US20040260312, US20060229641, US20080200798, US20100082040, US20110190787, US20120022368, US2013028022, US 20140121675, US20140128881, US20140128883, and US20140275978

What is claimed is:

1. An apparatus, comprising:
a needle holder having an axis and configured to hold a needle-like instrument aligned relative to a subject of needle placement;
a rotary mechanism having a remote center of motion and configured to rotate the needle holder such that the axis of the needle holder passes through the remote center of motion and traces a first conical region of coverage on the subject of needle placement;
a base body rigidly fixed to the rotary mechanism; and
an attachment that supports the base body and is configured to be mounted onto the subject of needle placement,
wherein the attachment changes an inclination of the base body with respect to the subject of needle placement and shifts the first conical region of coverage by an angle proportional to the change in inclination such that the axis of the needle holder intersects an insertion target located outside of the first conical region of coverage.

2. The apparatus according to claim 1,
wherein the base body comprises a cylindrical portion and the attachment comprises an axial fitting portion configured to be fitted with the cylindrical portion of the base body.

3. The apparatus according to claim 1,
wherein the attachment comprises:
a movable portion and a fixed portion; and
a brake unit configured to inhibit movement of the movable portion relative to the fixed portion.

4. The apparatus according to claim 3,
wherein the fixed portion includes a mount surface configured to be disposed on a surface of the subject of needle placement,
wherein the rotary mechanism comprises a rotary guide having a rotational axis that intersects the remote center of motion at an angle, and
wherein the rotary guide is configured to move the needle holder so as to position the axis of the needle holder to any position within the first conical region of coverage.

5. The apparatus according to claim 4,
wherein the mount surface includes a curved surface that adapts to a shape of the subject of needle placement, and
wherein the remote center of motion is located on a point along the curved surface.

6. The apparatus according to claim 3,
wherein each of the movable portion and the fixed portion includes a spherical surface which form a spherical guide extending along a spherical locus, and
wherein the spherical guide guides the movable portion relative to the fixed portion about a center point of the spherical locus.

7. The apparatus according to claim 6,
wherein the rotary mechanism includes a rotary guide having a rotational axis that intersects the remote center of motion at an angle, and
wherein the center point of the spherical locus coincides with the remote center of motion.

8. The apparatus according to claim 3,
wherein each of the movable portion and the fixed portion comprises a cylindrical surface which form a cylindrical guide, and
wherein the movable portion moves along the cylindrical guide relative to the fixed portion about a central axis which is common to both cylindrical surfaces.

9. The apparatus according to claim 8, wherein the remote center of motion of the rotary mechanism intersects with the central axis of the cylindrical surfaces.

10. The apparatus according to claim 3,
wherein the attachment further comprises a rotatable bearing configured to rotate the movable portion relative to the fixed portion more than 360 degrees about an axis.

11. The apparatus according to claim 3, wherein the attachment is disposed between the base body and an RF (radio frequency) coil disposed on a surface of the subject of needle placement.

12. The apparatus according to claim 11,
wherein the attachment further comprises a mount portion for determining a position of the attachment relative to the RF coil, and for maintaining the position of the RF coil in place.

13. The apparatus according to claim 12,
wherein an adhesive material is disposed on part of the mounting portion to temporarily bond the RF coil to the fixed portion of the attachment, and
wherein a position of the attachment relative to the RF coil is maintained by an adhesive force of the adhesive material.

14. The apparatus according to claim 3,
wherein the brake unit comprises a pressing unit that presses a contact portion provided at the fixed portion against the movable portion,
wherein a position or posture of the movable portion is fixed by the pressing unit, and
wherein the fixed position or posture of the movable portion is released by attenuating a pushing force of the pressing unit or by temporarily changing a direction of the pushing force.

15. The apparatus according to claim 14,
wherein the brake unit comprises a piezoelectric element provided at the fixed portion, a contact portion disposed at an end of the piezoelectric element, and an elastic member that presses the contact portion against the movable portion, and
wherein the fixed position or posture of the movable portion is released by applying an alternating voltage to the piezoelectric element.

16. The apparatus according to claim 1,
wherein the attachment comprises:
a fixed portion,
a first movable portion configured to move relative to the fixed portion; and
a second movable portion configured to move relative to the first movable portion,
wherein a first guide is formed between the fixed portion and the first movable portion, and a second guide is formed between the first movable portion and the second movable portion, the second guide being configured to support and guide the second movable portion with respect to the first movable portion.

17. The apparatus according to claim 16,
wherein the fixed portion includes a mount surface configured to be disposed on a surface of the subject of needle placement,
wherein the mount surface includes a curved surface that adapts to a shape of the subject of needle placement, and
wherein one or more of a distance from the first guide to the curved surface and a distance from the second guide to the curved surface are constant.

18. The apparatus according to claim 16, wherein at least one of the first guide and the second guide comprises a linear guide that supports and linearly guides the first movable portion or the second movable portion.

19. The apparatus according to claim 16, wherein at least one of the first guide and the second guide comprises a cylindrical guide that supports and guides the first movable portion or the second movable portion on a cylindrical surface.

20. The apparatus according to claim 19,
wherein the fixed portion includes a mount surface configured to be disposed on a surface of the subject of needle placement,
wherein the mount surface includes a curved surface that adapts to a shape of the subject of needle placement,
wherein the mount surface of the fixed portion comprises a spherical surface, and
wherein a center of the spherical surface including the mount surface of the fixed portion intersects a central axis of the cylindrical guide.

21. The apparatus according to claim 16, wherein at least one of the first guide and the second guide comprises a spherical guide that supports and guides the first movable portion or the second movable portion along a spherical locus.

22. The apparatus according to claim 21,
wherein the first guide and the second guide comprises a spherical guide that supports and guides the first movable portion or the second movable portion along the spherical locus, and
wherein a center of the spherical locus including the mount surface coincides with a center of the first and second spherical guides.

23. The apparatus according to claim 1,
wherein the attachment comprises one or more wedge-shaped adapters configured to change the inclination of the rotary mechanism with respect to the subject of needle placement by a predetermined angle.

24. The apparatus according to claim 23,
wherein at least one of the one or more wedge-shaped adapters has an inclined surface having a predetermined angle, and
wherein the inclined surface shifts the first conical region of coverage by the predetermined angle so that the axis of the needle holder intersects the insertion target that was located outside the first conical region of coverage before the shift.

25. The apparatus according to claim 23,
wherein the attachment further comprises a mounting base shaped according to a contour shape of the subject of needle placement,
wherein the mounting base includes a curved surface configured to fit the contour shape of the subject of needle placement, a setting portion on which an RF-coil array is set and a protruding portion having an inclined surface, wherein the protruding portion is configured to align with an opening among plural openings in the RF-coil array, and wherein the one or more wedge-shaped adapters are arranged on the inclined surface of the mounting base between the attachment and the base body so as to change the inclination of the rotary mechanism with respect to the subject of needle placement.

26. The apparatus according to claim 25, wherein the predetermined angle is configured to ensure the rotary mechanism does not interfere with an amplifier enclosure which is adjacent to the opening of the RF-coil array aligned with the protruding portion.

27. The apparatus according to claim 23,
wherein the attachment further comprises a mounting base shaped according to a contour shape of the subject of needle placement,
wherein the mounting base includes a curved surface configured to fit the contour shape of the subject of needle placement, a setting portion on which an RF-coil array is set and a protruding portion configured to be aligned with an opening among plural openings in the RF-coil array,
wherein one of the one or more wedge-shaped adapters has an inclined surface and is integrated with the protruding portion of the mounting base as a single piece such that the inclined surface changes the inclination of the rotary mechanism with respect to the subject of needle placement.

28. The apparatus according to claim 23,
wherein the attachment further comprises one or more linear guides integrated with the one or more wedge-shaped adapters, and
wherein the linear guides and the one or more wedge-shaped adapters are arranged between the subject of needle placement and the base body of the rotary mechanism.

29. The apparatus according to claim 28, wherein at least one of the one or more linear guides is a fixed distance translation adapter configured to move the remote center of motion either along an inclined surface or along a direction orthogonal to the inclined surface of the one or more wedge-shaped adapters.

30. An attachment for use with a radio frequency (RF) coil when an image of a subject of needle placement is captured by a magnetic resonance imaging (MRI) modality, the attachment comprising:
a protruding portion configured to be fitted into an opening of the RF coil; and
a guide portion having an inclined surface configured to support a needle placement manipulator in an inclined manner above the RF coil;
the needle placement manipulator comprising a rotary mechanism having a remote center of motion and configured to rotate a needle holder such that an axis of the needle holder passes through the remote center of motion and traces a first conical region of coverage on the subject of needle placement,
wherein the guide portion is wedge-shaped and configured to change an inclination of the needle placement manipulator with respect to the subject of needle placement and to shift the first conical region of coverage by an angle proportional to the change in inclination such that the axis of the needle holder intersects an insertion target located outside of the first conical region of coverage.

31. The attachment according to claim 30, further comprising a locking mechanism that maintains a relative positional relationship between the needle placement manipulator and the attachment on an inclined surface side of the attachment.

32. The attachment according to claim 30,
wherein the RF coil is a phased-array coil, and
wherein the inclined surface of the guide portion has an inclination angle that enables the guide portion to avoid physical contact with a signal processing member that the phased-array coil includes near the opening into which the protruding portion is fitted.

33. The attachment according to claim 30,
wherein the inclined surface of the guide portion has an inclination angle $\delta$ in a range of 5 to 30 degrees.

34. The attachment according to claim 30,
wherein the first conical region of coverage has the remote center of motion as a vertex and the base of the first conical region of coverage extends in a direction towards the subject of needle placement, where $\theta$ is an angle formed by axes of a first rotation guide and a second rotation guide of the rotary mechanism to satisfy $0° < \theta < 90°$.

35. The attachment according to claim 30,
wherein the first conical region of coverage has an apical angle $4\theta$ and the inclined surface of the guide portion has an inclination angle $\delta$, and
wherein the guide portion is configured to change an inclination of the needle placement manipulator with respect to the subject of needle placement such that the first conical region of coverage is shifted by the inclination angle $\delta$ and the first conical region of coverage increases to a second conical region of coverage having an apical angle of $4\theta + 2\delta$ and with the remote center of motion at the vertex.

* * * * *